US010369218B2

(12) United States Patent
Handa et al.

(10) Patent No.: US 10,369,218 B2
(45) Date of Patent: Aug. 6, 2019

(54) IMMUNOSTIMULATOR AND METHOD FOR PRODUCING THE SAME

(71) Applicants: Saitama Medical University, Iruma-gun, Saitama (JP); SYSMEX CORPORATION, Kobe-shi, Hyogo (JP)

(72) Inventors: Hiroshi Handa, Tokyo (JP); Masaaki Kawano, Saitama (JP); Masahiko Kato, Hyogo (JP)

(73) Assignees: Hiroshi Handa, Tokyo (JP); Saitama Medical University, Iruma-gun, Saitama (JP); SYSMEX CORPORATION, Kobe-shi, Hyogo (JP)

( * ) Notice: Subject to any disclaimer, the term of this patent is extended or adjusted under 35 U.S.C. 154(b) by 0 days.

(21) Appl. No.: 15/387,951

(22) Filed: Dec. 22, 2016

(65) Prior Publication Data

US 2017/0182157 A1 Jun. 29, 2017

(30) Foreign Application Priority Data

Dec. 25, 2015 (JP) ................................ 2015-255012

(51) Int. Cl.
*A61K 39/00* (2006.01)
*A61K 39/39* (2006.01)

(52) U.S. Cl.
CPC .............. *A61K 39/39* (2013.01); *A61K 39/00* (2013.01); *A61K 2039/5258* (2013.01); *A61K 2039/555* (2013.01); *C12N 2710/14043* (2013.01); *C12N 2710/22023* (2013.01)

(58) Field of Classification Search
None
See application file for complete search history.

(56) References Cited

U.S. PATENT DOCUMENTS

2008/0131928 A1 6/2008 Handa et al.
2009/0298955 A1 12/2009 Handa et al.
2015/0174223 A1 6/2015 Tsunoda et al.

FOREIGN PATENT DOCUMENTS

WO 2006/004173 A1 1/2006
WO 2006/088229 A1 8/2006
WO 2014/041784 A1 3/2014

OTHER PUBLICATIONS

UniProtKB-Q910R7 SV40 Capsid protein VP1, 2001.*
Bulavaite et al. Construction of recombinant chimeric proteins on the basis of SV40 virus major capsid protein VP1. Biologija. 2002. Nr. 3. p. 10-12.*

(Continued)

*Primary Examiner* — Michelle S Horning
(74) *Attorney, Agent, or Firm* — Sughrue Mion, PLLC

(57) ABSTRACT

Disclosed is an immunostimulator containing virus-like particles, in which the virus-like particles contain an outer coat protein containing an amino acid sequence selected from the group consisting of SEQ ID No. 1, SEQ ID No. 26, SEQ ID No. 33, SEQ ID No. 35, SEQ ID No. 37, SEQ ID No. 39, SEQ ID No. 41, SEQ ID No. 43 and SEQ ID No. 45; the outer coat protein constitutes an outer coat of the virus-like particles; and the virus-like particles do not substantially contain a genome DNA of SV40.

4 Claims, 18 Drawing Sheets

Specification includes a Sequence Listing.

(56) References Cited

OTHER PUBLICATIONS

Teunissen et al. Production and biomedical applications of virus-like particles derived from polyomaviruses. J Control Release. Nov. 28, 2013;172(1):305-21.*
Kosukegawa et al. Purification and characterization of virus-like particles and pentamers produced by the expression of SV40 capsid proteins in insect cells. Biochim Biophys Acta. May 21, 1996;1290(1):37-45. (Year: 1996).*
Baker et al., Protein Structure Predication and Structural Genomics, Science (2001) vol. 294, No. 5540, pp. 93-96 (Year: 2001).*
Attwood, T. The Babel of Bioinformatics, Science (2000) vol. 290, No. 5491, pp. 471-473 (Year: 2000).*
Kawano et al. SV40 virus-like particles as an effective delivery system and its application to a vaccine carrier. Expert Rev. Vaccines 12(2), 199-210 (2013) (Year: 2013).*
Takamasa Inoue et al., "Engineering of SV40-based nano-capsules for delivery of heterologous proteins as fusions with the minor capsid proteins VP2/3," Journal of Biotechnology, 2008, pp. 181-192, vol. 134.
Ryou-U Takahashi et al., "Presentation of functional foreign peptides on the surface of SV40 virus-like particles," Journal of Biotechnology, 2008, pp. 385-392, vol. 135.
Masaaki Kawano et al., "Chimeric SV40 virus-like particles induce specific cytotoxicity and protective immunity against influenza A virus without the need of adjuvants," Virology, 2014, pp. 159-167, vol. 448.

* cited by examiner

SEQUENCE LISTING

```
<160> NUMBER OF SEQ ID NOS: 48

<210> SEQ ID NO 1
<211> LENGTH: 364
<212> TYPE: PRT
<213> ORGANISM: Polyomavirus SV40

<400> SEQUENCE: 1

Met Lys Met Ala Pro Thr Lys Arg Lys Gly Ser Cys Pro Gly Ala Ala
1               5                   10                  15

Pro Lys Lys Pro Lys Glu Pro Val Gln Val Pro Lys Leu Val Ile Lys
            20                  25                  30

Gly Gly Ile Glu Val Leu Gly Val Lys Thr Gly Val Asp Ser Phe Thr
        35                  40                  45

Glu Val Glu Cys Phe Leu Asn Pro Gln Met Gly Asn Pro Asp Glu His
    50                  55                  60

Gln Lys Gly Leu Ser Lys Ser Leu Ala Ala Glu Lys Gln Phe Thr Asp
65                  70                  75                  80

Asp Ser Pro Asp Lys Glu Gln Leu Pro Cys Tyr Ser Val Ala Arg Ile
                85                  90                  95

Pro Leu Pro Asn Leu Asn Glu Asp Leu Thr Cys Gly Asn Ile Leu Met
            100                 105                 110

Trp Glu Ala Val Thr Val Lys Thr Glu Val Ile Gly Val Thr Ala Met
        115                 120                 125

Leu Asn Leu His Ser Gly Thr Gln Lys Thr His Glu Asn Gly Ala Gly
    130                 135                 140
```

-continued

```
Lys Pro Ile Gln Gly Ser Asn Phe His Phe Phe Ala Val Gly Gly Glu
145                 150                 155                 160

Pro Leu Glu Leu Gln Gly Val Leu Ala Asn Tyr Arg Thr Lys Tyr Pro
                165                 170                 175

Ala Gln Thr Val Thr Pro Lys Asn Ala Thr Val Asp Ser Gln Gln Met
            180                 185                 190

Asn Thr Asp His Lys Ala Val Leu Asp Lys Asp Asn Ala Tyr Pro Val
        195                 200                 205

Glu Cys Trp Val Pro Asp Pro Ser Lys Asn Glu Asn Thr Arg Tyr Phe
    210                 215                 220

Gly Thr Tyr Thr Gly Gly Glu Asn Val Pro Pro Val Leu His Ile Thr
225                 230                 235                 240

Asn Thr Ala Thr Thr Val Leu Leu Asp Glu Gln Gly Val Gly Pro Leu
                245                 250                 255

Cys Lys Ala Asp Ser Leu Tyr Val Ser Ala Val Asp Ile Cys Gly Leu
            260                 265                 270

Phe Thr Asn Thr Ser Gly Thr Gln Gln Trp Lys Gly Leu Pro Arg Tyr
        275                 280                 285

Phe Lys Ile Thr Leu Arg Lys Arg Ser Val Lys Asn Pro Tyr Pro Ile
    290                 295                 300

Ser Phe Leu Leu Ser Asp Leu Ile Asn Arg Arg Thr Gln Arg Val Asp
305                 310                 315                 320

Gly Gln Pro Met Ile Gly Met Ser Ser Gln Val Glu Glu Val Arg Val
                325                 330                 335

Tyr Glu Asp Thr Glu Glu Leu Pro Gly Asp Pro Asp Met Ile Arg Tyr
            340                 345                 350

Ile Asp Glu Phe Gly Gln Thr Thr Thr Arg Met Gln
        355                 360
```

<210> SEQ ID NO 2
<211> LENGTH: 1095
<212> TYPE: DNA
<213> ORGANISM: Polyomavirus SV40

<400> SEQUENCE: 2

```
atgaagatgg ccccaacaaa aagaaaagga agttgtccag gggcagctcc caaaaaacca     60

aaggaaccag tgcaagtgcc aaagctcgtc ataaaaggag gaatagaagt tctaggagtt    120

aaaactggag tagacagctt cactgaggtg gagtgctttt taaatcctca aatgggcaat    180

cctgatgaac atcaaaaagg cttaagtaaa agcttagcag ctgaaaaaca gtttacagat    240

gactctccag acaaagaaca actgccttgc tacagtgtgg ctagaattcc tttgcctaat    300

ttaaatgagg acttaacctg tggaaatatt ttgatgtggg aagctgttac tgttaaaact    360

gaggttattg gggtaactgc tatgttaaac ttgcattcag ggacacaaaa aactcatgaa    420

aatggtgctg gaaaacccat tcaagggtca aattttcatt tttttgctgt tggtggggaa    480

cctttggagc tgcagggtgt gttagcaaac tacaggacca aatatcctgc tcaaactgta    540

accccaaaaa atgctacagt tgacagtcag cagatgaaca ctgaccacaa ggctgttttg    600

gataaggata atgcttatcc agtggagtgc tgggttcctg atccaagtaa aaatgaaaac    660

actagatatt ttggaaccta cacaggtggg gaaaatgtgc ctcctgtttt gcacattact    720

aacacagcaa ccacagtgct tcttgatgag cagggtgttg ggcccttgtg caaagctgac    780

agcttgtatg tttctgctgt tgacatttgt gggctgttta ccaacacttc tggaacacag    840

cagtggaagg gacttcccag atattttaaa attaccctta gaaagcggtc tgtgaaaaac    900
```

-continued ccctacccaa tttccttttt gttaagtgac ctaattaaca ggaggacaca gagggtggat 960
gggcagccta tgattggaat gtcctctcaa gtagaggagg ttagggttta tgaggacaca 1020
gaggagcttc ctggggatcc agacatgata agatacattg atgagtttgg acaaaccaca 1080
actagaatgc agtga 1095

<210> SEQ ID NO 3
<211> LENGTH: 9
<212> TYPE: PRT
<213> ORGANISM: Influenza virus

<400> SEQUENCE: 3

Gly Ile Leu Gly Phe Val Phe Thr Leu
1 5

<210> SEQ ID NO 4
<211> LENGTH: 36
<212> TYPE: DNA
<213> ORGANISM: Artificial Sequence
<220> FEATURE:
<223> OTHER INFORMATION: Synthetic sequence, Overhang PCR primer 1 for FMP-DE-VLP

<400> SEQUENCE: 4
aaaagtcgac accatgaaga tggccccaac aaaaag 36

<210> SEQ ID NO 5
<211> LENGTH: 57
<212> TYPE: DNA
<213> ORGANISM: Artificial Sequence
<220> FEATURE:
<223> OTHER INFORMATION: Synthetic sequence, Overhang PCR primer 2 for FMP-DE-VLP

<400> SEQUENCE: 5
cgtgaacaca aagcccaaaa tgccgccacc gccatgagtt ttttgtgtcc ctgaatg 57

<210> SEQ ID NO 6
<211> LENGTH: 56
<212> TYPE: DNA
<213> ORGANISM: Artificial Sequence
<220> FEATURE:
<223> OTHER INFORMATION: Synthetic sequence, Overhang PCR primer for FMP-DE-VLP

<400> SEQUENCE: 6
cattttgggc tttgtgttca cgttgggcgg cggtggtgct ggaaaaccca ttcaag 56

<210> SEQ ID NO 7
<211> LENGTH: 34
<212> TYPE: DNA
<213> ORGANISM: Artificial Sequence
<220> FEATURE:
<223> OTHER INFORMATION: Synthetic sequence, Overhang PCR primer 4 for FMP-DE-VLP

<400> SEQUENCE: 7
aaaaggtacc tcactgcatt ctagttgtgg tttg 34

<210> SEQ ID NO 8
<211> LENGTH: 55
<212> TYPE: DNA
<213> ORGANISM: Artificial Sequence
<220> FEATURE:
<223> OTHER INFORMATION: Synthetic sequence, Overhang PCR primer 1 for

FMP-HI-VLP

<400> SEQUENCE: 8
cgtgaacaca aagcccaaaa tgccgccacc gccgttggta aacagcccac aaatg 55

<210> SEQ ID NO 9
<211> LENGTH: 54
<212> TYPE: DNA
<213> ORGANISM: Artificial Sequence
<220> FEATURE:
<223> OTHER INFORMATION: Synthetic sequence, Overhang PCR primer 2 for FMP-HI-VLP

<400> SEQUENCE: 9
cattttgggc tttgtgttca cgttgggcgg cggtggaaca cagcagtgga aggg 54

<210> SEQ ID NO 10
<211> LENGTH: 36
<212> TYPE: DNA
<213> ORGANISM: Artificial Sequence
<220> FEATURE:
<223> OTHER INFORMATION: Synthetic sequence, Overhang PCR primer 1 for DE-FLAG-VP1

<400> SEQUENCE: 10
aaaagtcgac accatgaaga tggccccaac aaaaag 36

<210> SEQ ID NO 11
<211> LENGTH: 57
<212> TYPE: DNA
<213> ORGANISM: Artificial Sequence
<220> FEATURE:
<223> OTHER INFORMATION: Synthetic sequence, Overhang PCR primer 2 for DE-FLAG-VP1

<400> SEQUENCE: 11
cttgtcatcg tcgtccttgt agtctcctcc tccatgagtt ttttgtgtcc ctgaatg 57

<210> SEQ ID NO 12
<211> LENGTH: 53
<212> TYPE: DNA
<213> ORGANISM: Artificial Sequence
<220> FEATURE:
<223> OTHER INFORMATION: Synthetic sequence, Overhang PCR primer 4 for DE-FLAG-VP1

<400> SEQUENCE: 12
ctacaaggac gacgatgaca agggaggagg aggtgctgga aaacccattc aag 53

<210> SEQ ID NO 13
<211> LENGTH: 34
<212> TYPE: DNA
<213> ORGANISM: Artificial Sequence
<220> FEATURE:
<223> OTHER INFORMATION: Synthetic sequence, Overhang PCR primer 4 for DE-FLAG-VP1

<400> SEQUENCE: 13
aaaaggtacc tcactgcatt ctagttgtgg tttg 34

<210> SEQ ID NO 14
<211> LENGTH: 57
<212> TYPE: DNA
<213> ORGANISM: Artificial Sequence
<220> FEATURE:
<223> OTHER INFORMATION: Synthetic sequence, Overhang PCR primer 1 for DE-3xRGD-VP1

<400> SEQUENCE: 14
gcctctatcg cccctgtctc ctctgcctcc tccatgagtt ttttgtgtcc ctgaatg 57

<210> SEQ ID NO 15
<211> LENGTH: 54
<212> TYPE: DNA
<213> ORGANISM: Artificial Sequence
<220> FEATURE:
<223> OTHER INFORMATION: Synthetic sequence, Overhang PCR primer 2 for DE-3xRGD-VP1

<400> SEQUENCE: 15
gagacagggg cgatagaggc gacgggggag gaggtgctgg aaaacccatt caag 54

<210> SEQ ID NO 16
<211> LENGTH: 352
<212> TYPE: PRT
<213> ORGANISM: Polyomavirus SV40

<400> SEQUENCE: 16

```
Met Gly Ala Ala Leu Thr Leu Leu Gly Asp Leu Ile Ala Thr Val Ser
1               5                   10                  15

Glu Ala Ala Ala Ala Thr Gly Phe Ser Val Ala Glu Ile Ala Ala Gly
            20                  25                  30

Glu Ala Ala Ala Ala Ile Glu Val Gln Leu Ala Ser Val Ala Thr Val
        35                  40                  45

Glu Gly Leu Thr Thr Ser Glu Ala Ile Ala Ala Ile Gly Leu Thr Pro
    50                  55                  60

Gln Ala Tyr Ala Val Ile Ser Gly Ala Pro Ala Ala Ile Ala Gly Phe
65                  70                  75                  80

Ala Ala Leu Leu Gln Thr Val Thr Gly Val Ser Ala Val Ala Gln Val
                85                  90                  95

Gly Tyr Arg Phe Phe Ser Asp Trp Asp His Lys Val Ser Thr Val Gly
            100                 105                 110

Leu Tyr Gln Gln Pro Gly Met Ala Val Asp Leu Tyr Arg Pro Asp Asp
        115                 120                 125

Tyr Tyr Asp Ile Leu Phe Pro Gly Val Gln Thr Phe Val His Ser Val
    130                 135                 140

Gln Tyr Leu Asp Pro Arg His Trp Gly Pro Thr Leu Phe Asn Ala Ile
145                 150                 155                 160

Ser Gln Ala Phe Trp Arg Val Ile Gln Asn Asp Ile Pro Arg Leu Thr
                165                 170                 175

Ser Gln Glu Leu Glu Arg Arg Thr Gln Arg Tyr Leu Arg Asp Ser Leu
            180                 185                 190

Ala Arg Phe Leu Glu Glu Thr Thr Trp Thr Val Ile Asn Ala Pro Val
        195                 200                 205

Asn Trp Tyr Asn Ser Leu Gln Asp Tyr Tyr Ser Thr Leu Ser Pro Ile
    210                 215                 220

Arg Pro Thr Met Val Arg Gln Val Ala Asn Arg Glu Gly Leu Gln Ile
225                 230                 235                 240

Ser Phe Gly His Thr Tyr Asp Asn Ile Asp Glu Ala Asp Ser Ile Gln
                245                 250                 255

Gln Val Thr Glu Arg Trp Glu Ala Gln Ser Gln Ser Pro Asn Val Gln
            260                 265                 270

Ser Gly Glu Phe Ile Glu Lys Phe Glu Ala Pro Gly Gly Ala Asn Gln
        275                 280                 285
```

-continued

Arg Thr Ala Pro Gln Trp Met Leu Pro Leu Leu Leu Gly Leu Tyr Gly
    290                 295                 300

Ser Val Thr Ser Ala Leu Lys Ala Tyr Glu Asp Gly Pro Asn Lys Lys
305                 310                 315                 320

Lys Arg Lys Leu Ser Arg Gly Ser Ser Gln Lys Thr Lys Gly Thr Ser
                325                 330                 335

Ala Ser Ala Lys Ala Arg His Lys Arg Arg Asn Arg Ser Ser Arg Ser
            340                 345                 350

<210> SEQ ID NO 17
<211> LENGTH: 1059
<212> TYPE: DNA
<213> ORGANISM: Polyomavirus SV40

<400> SEQUENCE: 17
atgggtgctg ctttaacact gttgggggac ctaattgcta ctgtgtctga agctgctgct 60
gctactggat tttcagtagc tgaaattgct gctggagagg ccgctgctgc aattgaagtg 120
caacttgcat ctgttgctac tgttgaaggc ctaacaacct ctgaggcaat tgctgctata 180
ggcctcactc cacaggccta tgctgtgata tctggggctc ctgctgctat agctggattt 240
gcagctttac tgcaaactgt gactggtgtg agcgctgttg ctcaagtggg gtatagattt 300
tttagtgact gggatcacaa agtttctact gttggtttat atcaacaacc aggaatggct 360
gtagatttgt ataggccaga tgattactat gatattttat ttcctggagt acaaaccttt 420
gttcacagtg ttcagtatct tgaccccaga cattggggtc caacactttt taatgccatt 480
tctcaagctt tttggcgtgt aatacaaaat gacattccta ggctcacctc acaggagctt 540
gaaagaagaa cccaaagata tttaagggac agtttggcaa ggtttttaga ggaaactact 600
tggacagtaa ttaatgctcc tgttaattgg tataactctt tacaagatta ctactctact 660
ttgtctccca ttaggcctac aatggtgaga caagtagcca acagggaagg gttgcaaata 720
tcatttgggc acacctatga taatattgat gaagcagaca gtattcagca agtaactgag 780
aggtgggaag ctcaaagcca aagtcctaat gtgcagtcag gtgaatttat tgaaaaattt 840
gaggctcctg gtggtgcaaa tcaaagaact gctcctcagt ggatgttgcc tttacttcta 900
ggcctgtacg gaagtgttac ttctgctcta aaagcttatg aagatggccc caacaaaaag 960
aaaaggaagt tgtccagggg cagctcccaa aaaaccaaag gaaccagtgc aagtgccaaa 1020
gctcgtcata aaaggaggaa tagaagttct aggagttaa 1059

<210> SEQ ID NO 18
<211> LENGTH: 24
<212> TYPE: DNA
<213> ORGANISM: Artificial Sequence
<220> FEATURE:
<223> OTHER INFORMATION: Synthetic sequence, FLAG tag encoding sequence

<400> SEQUENCE: 18
gactacaagg acgacgatga caag 24

<210> SEQ ID NO 19
<211> LENGTH: 15
<212> TYPE: PRT
<213> ORGANISM: Artificial Sequence
<220> FEATURE:
<223> OTHER INFORMATION: Synthetic sequence, GS linker

<400> SEQUENCE: 19

-continued

```
Gly Gly Gly Gly Ser Gly Gly Gly Gly Ser Gly Gly Gly Gly Ser
1               5                   10                  15


<210> SEQ ID NO 20
<211> LENGTH: 45
<212> TYPE: DNA
<213> ORGANISM: Artificial Sequence
<220> FEATURE:
<223> OTHER INFORMATION: Synthetic sequence, GS linker encoding sequence

<400> SEQUENCE: 20

ggtggtggtg gaagtggtgg tggtggaagt ggtggtggtg gaagt                     45


<210> SEQ ID NO 21
<211> LENGTH: 638
<212> TYPE: PRT
<213> ORGANISM: Artificial Sequence
<220> FEATURE:
<223> OTHER INFORMATION: Synthetic sequence, VP2 protein fused with M1
      via a GS linker

<400> SEQUENCE: 21

Met Gly Ser Ser Asp Tyr Lys Asp Asp Asp Asp Lys Ser Ser Gly Thr
1               5                   10                  15

Arg Met Gly Ala Ala Leu Thr Leu Leu Gly Asp Leu Ile Ala Thr Val
            20                  25                  30

Ser Glu Ala Ala Ala Ala Thr Gly Phe Ser Val Ala Glu Ile Ala Ala
        35                  40                  45

Gly Glu Ala Ala Ala Ala Ile Glu Val Gln Leu Ala Ser Val Ala Thr
    50                  55                  60

Val Glu Gly Leu Thr Thr Ser Glu Ala Ile Ala Ala Ile Gly Leu Thr
65                  70                  75                  80

Pro Gln Ala Tyr Ala Val Ile Ser Gly Ala Pro Ala Ala Ile Ala Gly
                85                  90                  95

Phe Ala Ala Leu Leu Gln Thr Val Thr Gly Val Ser Ala Val Ala Gln
            100                 105                 110

Val Gly Tyr Arg Phe Phe Ser Asp Trp Asp His Lys Val Ser Thr Val
        115                 120                 125

Gly Leu Tyr Gln Gln Pro Gly Met Ala Val Asp Leu Tyr Arg Pro Asp
    130                 135                 140

Asp Tyr Tyr Asp Ile Leu Phe Pro Gly Val Gln Thr Phe Val His Ser
145                 150                 155                 160

Val Gln Tyr Leu Asp Pro Arg His Trp Gly Pro Thr Leu Phe Asn Ala
                165                 170                 175

Ile Ser Gln Ala Phe Trp Arg Val Ile Gln Asn Asp Ile Pro Arg Leu
            180                 185                 190

Thr Ser Gln Glu Leu Glu Arg Arg Thr Gln Arg Tyr Leu Arg Asp Ser
        195                 200                 205

Leu Ala Arg Phe Leu Glu Glu Thr Thr Trp Thr Val Ile Asn Ala Pro
    210                 215                 220

Val Asn Trp Tyr Asn Ser Leu Gln Asp Tyr Tyr Ser Thr Leu Ser Pro
225                 230                 235                 240

Ile Arg Pro Thr Met Val Arg Gln Val Ala Asn Arg Glu Gly Leu Gln
                245                 250                 255

Ile Ser Phe Gly His Thr Tyr Asp Asn Ile Asp Glu Ala Asp Ser Ile
            260                 265                 270

Gln Gln Val Thr Glu Arg Trp Glu Ala Gln Ser Gln Ser Pro Asn Val
        275                 280                 285
```

```
Gln Ser Gly Glu Phe Ile Glu Lys Phe Glu Ala Pro Gly Gly Ala Asn
    290                 295                 300

Gln Arg Thr Ala Pro Gln Trp Met Leu Pro Leu Leu Leu Gly Leu Tyr
305                 310                 315                 320

Gly Ser Val Thr Ser Ala Leu Lys Ala Tyr Glu Asp Gly Pro Asn Lys
                325                 330                 335

Lys Lys Arg Lys Leu Ser Arg Gly Ser Ser Gln Lys Thr Lys Gly Thr
            340                 345                 350

Ser Ala Ser Ala Lys Ala Arg His Lys Arg Arg Asn Arg Ser Ser Arg
        355                 360                 365

Ser Glu Phe Gly Gly Gly Gly Ser Gly Gly Gly Gly Ser Gly Gly Gly
    370                 375                 380

Gly Ser Met Ser Leu Leu Thr Glu Val Glu Thr Tyr Val Leu Ser Ile
385                 390                 395                 400

Ile Pro Ser Gly Pro Leu Lys Ala Glu Ile Ala Gln Arg Leu Glu Asp
                405                 410                 415

Val Phe Ala Gly Lys Asn Thr Asp Leu Glu Val Leu Met Glu Trp Leu
            420                 425                 430

Lys Thr Arg Pro Ile Leu Ser Pro Leu Thr Lys Gly Ile Leu Gly Phe
        435                 440                 445

Val Phe Thr Leu Thr Val Pro Ser Glu Arg Gly Leu Gln Arg Arg Arg
    450                 455                 460

Phe Val Gln Asn Ala Leu Asn Gly Asn Gly Asp Pro Asn Asn Met Asp
465                 470                 475                 480

Lys Ala Val Lys Leu Tyr Arg Lys Leu Lys Arg Glu Ile Thr Phe His
                485                 490                 495

Gly Ala Lys Glu Ile Ser Leu Ser Tyr Ser Ala Gly Ala Leu Ala Ser
            500                 505                 510

Cys Met Gly Leu Ile Tyr Asn Arg Met Gly Ala Val Thr Thr Glu Val
        515                 520                 525

Ala Phe Gly Leu Val Cys Ala Thr Cys Glu Gln Ile Ala Asp Ser Gln
    530                 535                 540

His Arg Ser His Arg Gln Met Val Thr Thr Thr Asn Pro Leu Ile Arg
545                 550                 555                 560

His Glu Asn Arg Met Val Leu Ala Ser Thr Thr Ala Lys Ala Met Glu
                565                 570                 575

Gln Met Ala Gly Ser Ser Glu Gln Ala Ala Glu Ala Met Glu Val Ala
            580                 585                 590

Ser Gln Ala Arg Gln Met Val Gln Ala Met Arg Thr Ile Gly Thr His
        595                 600                 605

Pro Ser Ser Ser Ala Gly Leu Lys Asn Asp Leu Leu Glu Asn Leu Gln
    610                 615                 620

Ala Tyr Gln Lys Arg Met Gly Val Gln Met Gln Arg Phe Lys
625                 630                 635
```

<210> SEQ ID NO 22
<211> LENGTH: 1917
<212> TYPE: DNA
<213> ORGANISM: Artificial Sequence
<220> FEATURE:
<223> OTHER INFORMATION: Synthetic sequence, a gene encoding VP2 fused with M1 via a GS linker

<400> SEQUENCE: 22

```
atgggcagca gcgactacaa ggacgacgat gacaagagca gcggcacgcg tatgggtgct     60
```

gctttaacac tgttggggga cctaattgct actgtgtctg aagctgctgc tgctactgga 120
ttttcagtag ctgaaattgc tgctggagag gccgctgctg caattgaagt gcaacttgca 180
tctgttgcta ctgttgaagg cctaacaacc tctgaggcaa ttgctgctat aggcctcact 240
ccacaggcct atgctgtgat atctggggct cctgctgcta tagctggatt tgcagcttta 300
ctgcaaactg tgactggtgt gagcgctgtt gctcaagtgg ggtatagatt ttttagtgac 360
tgggatcaca aagtttctac tgttggttta tatcaacaac caggaatggc tgtagatttg 420
tataggccag atgattacta tgatatttta tttcctggag tacaaacctt tgttcacagt 480
gttcagtatc ttgaccccag acattggggt ccaacacttt ttaatgccat ttctcaagct 540
ttttggcgtg taatacaaaa tgacattcct aggctcacct cacaggagct tgaaagaaga 600
acccaaagat atttaaggga cagtttggca aggtttttag aggaaactac ttggacagta 660
attaatgctc ctgttaattg gtataactct ttacaagatt actactctac tttgtctccc 720
attaggccta caatggtgag acaagtagcc aacagggaag ggttgcaaat atcatttggg 780
cacacctatg ataatattga tgaagcagac agtattcagc aagtaactga gaggtgggaa 840
gctcaaagcc aaagtcctaa tgtgcagtca ggtgaattta ttgaaaaatt tgaggctcct 900
ggtggtgcaa atcaaagaac tgctcctcag tggatgttgc ctttacttct aggcctgtac 960
ggaagtgtta cttctgctct aaaagcttat gaagatggcc ccaacaaaaa gaaaaggaag 1020
ttgtccaggg gcagctccca aaaaaccaaa ggaaccagtg caagtgccaa agctcgtcat 1080
aaaaggagga atagaagttc taggagtgaa ttcggtggtg gtggaagtgg tggtggtgga 1140
agtggtggtg gtggaagtat gtcactccta accgaagtcg agacttatgt cctgagcatt 1200
ataccgtcag gtcctctaaa agccgaaatt gcccagcgtt tagaggatgt gttcgcaggg 1260
aagaacactg accttgaggt gctgatggag tggctgaaaa cccgacccat tcttagccca 1320
cttaccaaag gcatcctggg attcgtgttc acactgactg ttccatctga gagaggcttg 1380
cagaggagac gatttgttca gaatgccctc aatgggaatg gtgatcccaa caacatggac 1440
aaagccgtga agctttatcg caagctcaaa cgggagataa ccttccatgg agcgaaggaa 1500
atctccctca gttactctgc aggtgccttg gcgagctgta tgggcctgat ctacaatcgg 1560
atgggagccg tgacaacgga agtggctttt ggcctggtat gcgctacttg cgaacagatc 1620
gcagatagcc aacacaggtc ccacaggcag atggtcacca caaccaaccc tctgattcgg 1680
cacgagaaca gaatggtgtt agcgtccaca acggcaaaag ccatggaaca gatggccggc 1740
tcaagcgaac aagccgctga ggcaatggag gtagctagtc aggcaagaca gatggttcag 1800
gctatgagga ctatcgggac acatccctct tccagtgctg ggctgaagaa cgacctgttg 1860
gagaatctcc aagcctacca aaagcgcatg ggagtccaga tgcagcgctt taagtga 1917

<210> SEQ ID NO 23
<211> LENGTH: 5243
<212> TYPE: DNA
<213> ORGANISM: Polyomavirus SV40

<400> SEQUENCE: 23
gcctcggcct ctgcataaat aaaaaaaatt agtcagccat ggggcggaga atgggcggaa 60
ctgggcggag ttaggggcgg gatgggcgga gttaggggcg ggactatggt tgctgactaa 120
ttgagatgca tgctttgcat acttctgcct gctggggagc ctggggactt tccacacctg 180
gttgctgact aattgagatg catgctttgc atacttctgc ctgctgggga gcctggggac 240

-continued

```
tttccacacc ctaactgaca cacattccac agctggttct ttccgcctca gaaggtacct    300

aaccaagttc ctctttcaga ggttatttca ggccatggtg ctgcgccggc tgtcacgcca    360

ggcctccgtt aaggttcgta ggtcatggac tgaaagtaaa aaaacagctc aacgcctttt    420

tgtgtttgtt ttagagcttt tgctgcaatt ttgtgaaggg gaagatactg ttgacgggaa    480

acgcaaaaaa ccagaaaggt taactgaaaa accagaaagt taactggtaa gtttagtctt    540

tttgtctttt atttcaggtc catgggtgct gctttaacac tgttggggga cctaattgct    600

actgtgtctg aagctgctgc tgctactgga ttttcagtag ctgaaattgc tgctggagag    660

gccgctgctg caattgaagt gcaacttgca tctgttgcta ctgttgaagg cctaacaacc    720

tctgaggcaa ttgctgctat aggcctcact ccacaggcct atgctgtgat atctggggct    780

cctgctgcta tagctggatt tgcagcttta ctgcaaactg tgactggtgt gagcgctgtt    840

gctcaagtgg ggtatagatt ttttagtgac tgggatcaca aagtttctac tgttggttta    900

tatcaacaac caggaatggc tgtagatttg tataggccag atgattacta tgatatttta    960

tttcctggag tacaaacctt tgttcacagt gttcagtatc ttgaccccag acattggggt   1020

ccaacacttt ttaatgccat ttctcaagct ttttggcgtg taatacaaaa tgacattcct   1080

aggctcacct cacaggagct tgaaagaaga acccaaagat atttaaggga cagtttggca   1140

aggtttttag aggaaactac ttggacagta attaatgctc ctgttaattg gtataactct   1200

ttacaagatt actactctac tttgtctccc attaggccta caatggtgag acaagtagcc   1260

aacagggaag ggttgcaaat atcatttggg cacacctatg ataatattga tgaagcagac   1320

agtattcagc aagtaactga gaggtgggaa gctcaaagcc aaagtcctaa tgtgcagtca   1380

ggtgaattta ttgaaaaatt tgaggctcct ggtggtgcaa atcaaagaac tgctcctcag   1440

tggatgttgc ctttacttct aggcctgtac ggaagtgtta cttctgctct aaaagcttat   1500

gaagatggcc ccaacaaaaa gaaaaggaag ttgtccaggg gcagctccca aaaaaccaaa   1560

ggaaccagtg caagtgccaa agctcgtcat aaaaggagga atagaagttc taggagttaa   1620

aactggagta gacagcttca ctgaggtgga gtgcttttta aatcctcaaa tgggcaatcc   1680

tgatgaacat caaaaaggct taagtaaaag cttagcagct gaaaaacagt ttacagatga   1740

ctctccagac aaagaacaac tgccttgcta cagtgtggct agaattcctt tgcctaattt   1800

aaatgaggac ttaacctgtg gaaatatttt gatgtgggaa gctgttactg ttaaaactga   1860

ggttattggg gtaactgcta tgttaaactt gcattcaggg acacaaaaaa ctcatgaaaa   1920

tggtgctgga aaacccattc aagggtcaaa ttttcatttt tttgctgttg gtggggaacc   1980

tttggagctg cagggtgtgt tagcaaacta caggaccaaa tatcctgctc aaactgtaac   2040

cccaaaaaat gctacagttg acagtcagca gatgaacact gaccacaagg ctgttttgga   2100

taaggataat gcttatccag tggagtgctg ggttcctgat ccaagtaaaa atgaaaacac   2160

tagatatttt ggaacctaca caggtgggga aaatgtgcct cctgttttgc acattactaa   2220

cacagcaacc acagtgcttc ttgatgagca gggtgttggg cccttgtgca aagctgacag   2280

cttgtatgtt tctgctgttg acatttgtgg gctgtttacc aacacttctg gaacacagca   2340

gtggaaggga cttcccagat attttaaaat taccottaga aagcggtctg tgaaaaaccc   2400

ctacccaatt tcctttttgt taagtgacct aattaacagg aggacacaga gggtggatgg   2460

gcagcctatg attggaatgt cctctcaagt agaggaggtt agggtttatg aggacacaga   2520

ggagcttcct ggggatccag acatgataag atacattgat gagtttggac aaaccacaac   2580

tagaatgcag tgaaaaaaat gctttatttg tgaaatttgt gatgctattg ctttatttgt   2640
```

-continued

```
aaccattata agctgcaata aacaagttaa caacaacaat tgcattcatt ttatgtttca   2700
ggttcagggg gaggtgtggg aggtttttta aagcaagtaa aacctctaca aatgtggtat   2760
ggctgattat gatcatgaac agactgtgag gactgagggg cctgaaatga gccttgggac   2820
tgtgaatcaa tgcctgtttc atgccctgag tcttccatgt tcttctcccc accatcttca   2880
tttttatcag cattttcctg gctgtcttca tcatcatcat cactgtttct tagccaatct   2940
aaaactccaa ttcccatagc cacattaaac ttcatttttt gatacactga caaactaaac   3000
tctttgtcca atctctcttt ccactccaca attctgctct gaatactttg agcaaactca   3060
gccacaggtc tgtaccaaat taacataaga agcaaagcaa tgccactttg aattattctc   3120
ttttctaaca aaaactcact gcgttccagg caatgcttta aataatcttt gggcctaaaa   3180
tctatttgtt ttacaaatct ggcctgcagt gttttaggca cactgtactc attcatggtg   3240
actattccag gggaaatat ttgagttctt ttatttaggt gtttcttttc taagtttacc    3300
ttaacactgc catccaaata atcccttaaa ttgtccaggt tattaattcc ctgacctgaa   3360
ggcaaatctc tggactcccc tccagtgccc tttacatcct caaaaactac taaaaactgg   3420
tcaatagcta ctcctagctc aaagttcagc ctgtccaagg gcaaattaac atttaaagct   3480
ttccccccac ataattcaag caaagcagct gctaatgtag ttttaccact atcaattggt   3540
cctttaaaca gccagtatct ttttttagga atgttgtaca ccatgcattt taaaaagtca   3600
tacaccactg aatccatttt gggcaacaaa cagtgtagcc aagcaactcc agccatccat   3660
tcttctatgt cagcagagcc tgtagaacca aacattatat ccatcctatc caaaagatca   3720
ttaaatctgt ttgttaacat ttgttctcta gttaattgta ggctatcaac ccgcttttta   3780
gctaaaacag tatcaacagc ctgttggcat atggtttttt ggtttttgct gtcagcaaat   3840
atagcagcat ttgcataatg cttttcatgg tacttatagt ggctgggctg ttcttttta    3900
atacatttta aacacatttc aaaactgtac tgaaattcca agtacatccc aagcaataac   3960
aacacatcat cacattttgt ttccattgca tactctgtta caagcttcca ggacacttgt   4020
ttagtttcct ctgcttcttc tggattaaaa tcatgctcct ttaacccacc tggcaaactt   4080
tcctcaataa cagaaaatgg atctctagtc aaggcactat acatcaaata ttccttatta   4140
acccctttac aaattaaaaa gctaaaggta cacaattttt gagcatagtt attaatagca   4200
gacactctat gcctgtgtgg agtaagaaaa aacagtatgt tatgattata actgttatgc   4260
ctacttataa aggttacaga atatttttcc ataattttct tgtatagcag tgcagctttt   4320
tcctttgtgg tgtaaatagc aaagcaagca agagttctat tactaaacac agcatgactc   4380
aaaaaactta gcaattctga aggaaagtcc ttggggtctt ctacctttct cttcttttt    4440
ggaggagtag aatgttgaga gtcagcagta gcctcatcat cactagatgg catttcttct   4500
gagcaaaaca ggttttcctc attaaaggca ttccaccact gctcccattc atcagttcca   4560
taggttggaa tctaaaatac acaaacaatt agaatcagta gtttaacaca ttatacactt   4620
aaaaatttta tatttacctt agagctttaa atctctgtag gtagtttgtc caattatgtc   4680
acaccacaga agtaaggttc cttcacaaag atcaagtcca aaccacattc taaagcaatc   4740
gaagcagtag caatcaaccc acacaagtgg atctttcctg tataattttc tattttcatg   4800
cttcatcctc agtaagcaca gcaagcatat gcagttagca gacattttct ttgcacactc   4860
aggccattgt ttgcagtaca ttgcatcaac accaggattt aaggaagaag caaatacctc   4920
agttgcatcc cagaagcctc caaagtcagg ttgatgagca tattttactc catcttccat   4980
```

-continued tttcttgtac agagtattca ttttcttcat tttttcttca tctcctcctt tatcaggatg 5040
aaactccttg cattttttta aatatgcctt tctcatcaga ggaatattcc cccaggcact 5100
cctttcaaga cctagaaggt ccattagctg caaagattcc tctctgttta aaactttatc 5160
catctttgca aagctttttg caaaagccta ggcctccaaa aaagcctcct cactacttct 5220
ggaatagctc agaggccgag gcg 5243

<210> SEQ ID NO 24
<211> LENGTH: 8405
<212> TYPE: DNA
<213> ORGANISM: Artificial Sequence
<220> FEATURE:
<223> OTHER INFORMATION: Synthetic sequence, pUC-SV40

<400> SEQUENCE: 24
agcgcccaat acgcaaaccg cctctccccg cgcgttggcc gattcattaa tgcagctggc 60
acgacaggtt tcccgactgg aaagcgggca gtgagcgcaa cgcaattaat gtgagttagc 120
tcactcatta ggcaccccag gctttacact ttatgcttcc ggctcgtatg ttgtgtggaa 180
ttgtgagcgg ataacaattt cacacaggaa acagctatga ccatgattac gccaagcttg 240
catgcctgca ggtcgactct agaggatccc caggaagctc ctctgtgtcc tcataaaccc 300
taacctcctc tacttgagag gacattccaa tcataggctg cccatccacc ctctgtgtcc 360
tcctgttaat taggtcactt aacaaaaagg aaattgggta ggggttttc acagaccgct 420 ttctaagggt aattttaaaa tatctgggaa gtcccttcca ctgctgtgtt ccagaagtgt 480
tggtaaacag cccacaaatg tcaacagcag aaacatacaa gctgtcagct ttgcacaagg 540
gcccaacacc ctgctcatca agaagcactg tggttgctgt gttagtaatg tgcaaaacag 600
gaggcacatt ttccccacct gtgtaggttc caaaatatct agtgttttca tttttacttg 660
gatcaggaac ccagcactcc actggataag cattatcctt atccaaaaca gccttgtggt 720
cagtgttcat ctgctgactg tcaactgtag cattttttgg ggttacagtt tgagcaggat 780
atttggtcct gtagtttgct aacacaccct gcagctccaa aggttcccca ccaacagcaa 840
aaaaatgaaa atttgaccct tgaatgggtt ttccagcacc attttcatga gtttttttgtg 900 tccctgaatg caagtttaac atagcagtta ccccaataac ctcagtttta acagtaacag 960
cttcccacat caaaatattt ccacaggtta agtcctcatt taaattaggc aaaggaattc 1020
tagccacact gtagcaaggc agttgttctt tgtctggaga gtcatctgta aactgttttt 1080
cagctgctaa gcttttactt aagccttttt gatgttcatc aggattgccc atttgaggat 1140
ttaaaaagca ctccacctca gtgaagctgt ctactccagt tttaactcct agaacttcta 1200
ttcctccttt tatgacgagc tttggcactt gcactggttc ctttggtttt ttgggagctg 1260
cccctggaca acttcctttt ctttttgttg gggccatctt cataagcttt tagagcagaa 1320
gtaacacttc cgtacaggcc tagaagtaaa ggcaacatcc actgaggagc agttctttga 1380
tttgcaccac caggagcctc aaatttttca ataaattcac ctgactgcac attaggactt 1440
tggctttgag cttcccacct ctcagttact tgctgaatac tgtctgcttc atcaatatta 1500
tcataggtgt gcccaaatga tatttgcaac ccttccctgt tggctacttg tctcaccatt 1560
gtaggcctaa tgggagacaa agtagagtag taatcttgta aagagttata ccaattaaca 1620
ggagcattaa ttactgtcca agtagtttcc tctaaaaacc ttgccaaact gtcccttaaa 1680
tatctttggg ttcttctttc aagctcctgt gaggtgagcc taggaatgtc attttgtatt 1740
acacgccaaa aagcttgaga aatggcatta aaaagtgttg gaccccaatg tctggggtca 1800

```
agatactgaa cactgtgaac aaaggtttgt actccaggaa ataaaatatc atagtaatca   1860
tctggcctat acaaatctac agccattcct ggttgttgat ataaaccaac agtagaaact   1920
ttgtgatccc agtcactaaa aaatctatac cccacttgag caacagcgct cacaccagtc   1980
acagtttgca gtaaagctgc aaatccagct atagcagcag gagccccaga tatcacagca   2040
taggcctgtg gagtgaggcc tatagcagca attgcctcag aggttgttag gccttcaaca   2100
gtagcaacag atgcaagttg cacttcaatt gcagcagcgg cctctccagc agcaatttca   2160
gctactgaaa atccagtagc agcagcagct tcagacacag tagcaattag gtcccccaac   2220
agtgttaaag cagcacccat ggacctgaaa taaaagacaa aaagactaaa cttaccagtt   2280
aactttctgg tttttcagtt aacctttctg gtttttgcg tttcccgtca acagtatctt   2340
ccccttcaca aaattgcagc aaaagctcta aaacaaacac aaaaaggcgt tgagctgttt   2400
ttttactttc agtccatgac ctacgaacct taacggaggc ctggcgtgac agccggcgca   2460
gcaccatggc ctgaaataac ctctgaaaga ggaacttggt taggtacctt ctgaggcgga   2520
aagaaccagc tgtggaatgt gtgtcagtta gggtgtggaa agtccccagg ctccccagca   2580
ggcagaagta tgcaaagcat gcatctcaat tagtcagcaa ccaggtgtgg aaagtcccca   2640
ggctccccag caggcagaag tatgcaaagc atgcatctca attagtcagc aaccatagtc   2700
ccgcccctaa ctccgcccat cccgccccta actccgccca gttccgccca ttctccgccc   2760
catggctgac taattttttt tatttatgca gaggccgagg ccgcctcggc ctctgagcta   2820
ttccagaagt agtgaggagg cttttttgga ggcctaggct tttgcaaaaa gctttgcaaa   2880
gatggataaa gttttaaaca gagaggaatc tttgcagcta atggaccttc taggtcttga   2940
aaggagtgcc tgggggaata ttcctctgat gagaaaggca tatttaaaaa aatgcaagga   3000
gtttcatcct gataaaggag gagatgaaga aaaaatgaag aaaatgaata ctctgtacaa   3060
gaaaatggaa gatggagtaa aatatgctca tcaacctgac tttggaggct tctgggatgc   3120
aactgaggta tttgcttctt ccttaaatcc tggtgttgat gcaatgtact gcaaacaatg   3180
gcctgagtgt gcaaagaaaa tgtctgctaa ctgcatatgc ttgctgtgct tactgaggat   3240
gaagcatgaa aatagaaaat tatacaggaa agatccactt gtgtgggttg attgctactg   3300
cttcgattgc tttagaatgt ggtttggact tgatctttgt gaaggaacct tacttctgtg   3360
gtgtgacata attggacaaa ctacctacag agatttaaag ctctaaggta aatataaaat   3420
ttttaagtgt ataatgtgtt aaactactga ttctaattgt ttgtgtattt tagattccaa   3480
cctatggaac tgatgaatgg gagcagtggt ggaatgcctt taatgaggaa aacctgtttt   3540
gctcagaaga aatgccatct agtgatgatg aggctactgc tgactctcaa cattctactc   3600
ctccaaaaaa gaagagaaag gtagaagacc ccaaggactt tccttcagaa ttgctaagtt   3660
ttttgagtca tgctgtgttt agtaatagaa ctcttgcttg ctttgctatt tacaccacaa   3720
aggaaaaagc tgcactgcta tacaagaaaa ttatggaaaa atattctgta acctttataa   3780
gtaggcataa cagttataat cataacatac tgtttttttct tactccacac aggcatagag   3840
tgtctgctat taataactat gctcaaaaat tgtgtacctt tagcttttta atttgtaaag   3900
gggttaataa ggaatatttg atgtatagtg ccttgactag agatccattt tctgttattg   3960
aggaaagttt gccaggtggg ttaaaggagc atgattttaa tccagaagaa gcagaggaaa   4020
ctaaacaagt gtcctggaag cttgtaacag agtatgcaat ggaaacaaaa tgtgatgatg   4080
tgttgttatt gcttgggatg tacttggaat ttcagtacag ttttgaaatg tgtttaaaat   4140
```

-continued

```
gtattaaaaa agaacagccc agccactata agtaccatga aaagcattat gcaaatgctg   4200
ctatatttgc tgacagcaaa aaccaaaaaa ccatatgcca acaggctgtt gatactgttt   4260
tagctaaaaa gcgggttgat agcctacaat taactagaga acaaatgtta acaaacagat   4320
ttaatgatct tttggatagg atggatataa tgtttggttc tacaggctct gctgacatag   4380
aagaatggat ggctggagtt gcttggctac actgtttgtt gcccaaaatg gattcagtgg   4440
tgtatgactt tttaaaatgc atggtgtaca acattcctaa aaaaagatac tggctgttta   4500
aaggaccaat tgatagtggt aaaactacat tagcagctgc tttgcttgaa ttatgtgggg   4560
ggaaagcttt aaatgttaat ttgcccttgg acaggctgaa ctttgagcta ggagtagcta   4620
ttgaccagtt tttagtagtt tttgaggatg taaagggcac tggaggggag tccagagatt   4680
tgccttcagg tcagggaatt aataacctgg acaatttaag ggattatttg gatggcagtg   4740
ttaaggtaaa cttagaaaag aaacacctaa ataaaagaac tcaaatattt ccccctggaa   4800
tagtcaccat gaatgagtac agtgtgccta aaacactgca ggccagattt gtaaaacaaa   4860
tagattttag gcccaaagat tatttaaagc attgcctgga acgcagtgag tttttgttag   4920
aaaagagaat aattcaaagt ggcattgctt tgcttcttat gttaatttgg tacagacctg   4980
tggctgagtt tgctcaaagt attcagagca gaattgtgga gtggaaagag agattggaca   5040
aagagtttag tttgtcagtg tatcaaaaaa tgaagtttaa tgtggctatg ggaattggag   5100
ttttagattg gctaagaaac agtgatgatg atgatgaaga cagccaggaa aatgctgata   5160
aaaatgaaga tggtggggag aagaacatgg aagactcagg gcatgaaaca ggcattgatt   5220
cacagtccca aggctcattt caggcccctc agtcctcaca gtctgttcat gatcataatc   5280
agccatacca catttgtaga ggttttactt gctttaaaaa acctcccaca cctccccctg   5340
aacctgaaac ataaaatgaa tgcaattgtt gttgttaact tgtttattgc agcttataat   5400
ggttacaaat aaagcaatag catcacaaat ttcacaaata aagcattttt ttcactgcat   5460
tctagttgtg gtttgtccaa actcatcaat gtatcttatc atgtctggat ccccgggtac   5520
cgagctcgaa ttcactggcc gtcgttttac aacgtcgtga ctgggaaaac cctggcgtta   5580
cccaacttaa tcgccttgca gcacatcccc ctttcgccag ctggcgtaat agcgaagagg   5640
cccgcaccga tcgcccttcc caacagttgc gcagcctgaa tggcgaatgg cgcctgatgc   5700
ggtattttct ccttacgcat ctgtgcggta tttcacaccg catacgtcaa agcaaccata   5760
gtacgcgccc tgtagcggcg cattaagcgc ggcgggtgtg gtggttacgc gcagcgtgac   5820
cgctacactt gccagcgccc tagcgcccgc tcctttcgct ttcttccctt cctttctcgc   5880
cacgttcgcc ggctttcccc gtcaagctct aaatcggggg ctccctttag ggttccgatt   5940
tagtgcttta cggcacctcg accccaaaaa acttgatttg ggtgatggtt cacgtagtgg   6000
gccatcgccc tgatagacgg tttttcgccc tttgacgttg gagtccacgt tctttaatag   6060
tggactcttg ttccaaactg gaacaacact caaccctatc tcgggctatt cttttgattt   6120
ataagggatt ttgccgattt cggcctattg gttaaaaaat gagctgattt aacaaaaatt   6180
taacgcgaat tttaacaaaa tattaacgtt tacaatttta tggtgcactc tcagtacaat   6240
ctgctctgat gccgcatagt taagccagcc ccgacacccg ccaacacccg ctgacgcgcc   6300
ctgacgggct tgtctgctcc cggcatccgc ttacagacaa gctgtgaccg tctccgggag   6360
ctgcatgtgt cagaggtttt caccgtcatc accgaaacgc gcgagacgaa agggcctcgt   6420
gatacgccta tttttatagg ttaatgtcat gataataatg gtttcttaga cgtcaggtgg   6480
cacttttcgg ggaaatgtgc gcggaacccc tatttgttta tttttctaaa tacattcaaa   6540
```

-continued

```
tatgtatccg ctcatgagac aataaccctg ataaatgctt caataatatt gaaaaaggaa   6600
gagtatgagt attcaacatt tccgtgtcgc ccttattccc ttttttgcgg cattttgcct   6660
tcctgttttt gctcacccag aaacgctggt gaaagtaaaa gatgctgaag atcagttggg   6720
tgcacgagtg ggttacatcg aactggatct caacagcggt aagatccttg agagttttcg   6780
ccccgaagaa cgttttccaa tgatgagcac ttttaaagtt ctgctatgtg gcgcggtatt   6840
atcccgtatt gacgccgggc aagagcaact cggtcgccgc atacactatt ctcagaatga   6900
cttggttgag tactcaccag tcacagaaaa gcatcttacg gatggcatga cagtaagaga   6960
attatgcagt gctgccataa ccatgagtga taacactgcg gccaacttac ttctgacaac   7020
gatcggagga ccgaaggagc taaccgcttt tttgcacaac atgggggatc atgtaactcg   7080
ccttgatcgt tgggaaccgg agctgaatga agccatacca aacgacgagc gtgacaccac   7140
gatgcctgta gcaatggcaa caacgttgcg caaactatta actggcgaac tacttactct   7200
agcttcccgg caacaattaa tagactggat ggaggcggat aaagttgcag gaccacttct   7260
gcgctcggcc cttccggctg gctggtttat tgctgataaa tctggagccg gtgagcgtgg   7320
gtctcgcggt atcattgcag cactggggcc agatggtaag ccctcccgta tcgtagttat   7380
ctacacgacg gggagtcagg caactatgga tgaacgaaat agacagatcg ctgagatagg   7440
tgcctcactg attaagcatt ggtaactgtc agaccaagtt tactcatata tactttagat   7500
tgatttaaaa cttcattttt aatttaaaag gatctaggtg aagatccttt ttgataatct   7560
catgaccaaa atcccttaac gtgagttttc gttccactga gcgtcagacc ccgtagaaaa   7620
gatcaaagga tcttcttgag atcctttttt tctgcgcgta atctgctgct tgcaaacaaa   7680
aaaaccaccg ctaccagcgg tggtttgttt gccggatcaa gagctaccaa ctctttttcc   7740
gaaggtaact ggcttcagca gagcgcagat accaaatact gtccttctag tgtagccgta   7800
gttaggccac cacttcaaga actctgtagc accgcctaca tacctcgctc tgctaatcct   7860
gttaccagtg gctgctgcca gtggcgataa gtcgtgtctt accgggttgg actcaagacg   7920
atagttaccg gataaggcgc agcggtcggg ctgaacgggg ggttcgtgca cacagcccag   7980
cttggagcga acgacctaca ccgaactgag atacctacag cgtgagctat gagaaagcgc   8040
cacgcttccc gaagggagaa aggcggacag gtatccggta agcggcaggg tcggaacagg   8100
agagcgcacg agggagcttc cagggggaaa cgcctggtat ctttatagtc ctgtcgggtt   8160
tcgccacctc tgacttgagc gtcgattttt gtgatgctcg tcaggggggc ggagcctatg   8220
gaaaaacgcc agcaacgcgg cctttttacg gttcctggcc ttttgctggc cttttgctca   8280
catgttcttt cctgcgttat cccctgattc tgtggataac cgtattaccg cctttgagtg   8340
agctgatacc gctcgccgca gccgaacgac cgagcgcagc gagtcagtga gcgaggaagc   8400
ggaag                                                               8405
```

<210> SEQ ID NO 25
<211> LENGTH: 1095
<212> TYPE: DNA
<213> ORGANISM: Polyomavirus SV40

<400> SEQUENCE: 25

```
atgaagatgg ccccaacaaa aagaaaagga agttgtccag gggcagctcc caaaaaacca     60
aaggaaccag tgcaagtgcc aaagctcgtc ataaaaggag gaatagaagt tctaggagtt    120
aaaactggag tagacagctt cactgaggtg gagtgctttt taaatcctca aatgggcaat    180
```

-continued

```
cctgatgaac atcaaaaagg cttaagtaaa agcttagcag ctgaaaaaca gtttacagat    240

gactctccag acaaagaaca actgccttgc tacagtgtgg ctagaattcc tttgcctaat    300

ttaaatgagg acttaacctg tggaaatatt ttgatgtggg aagctgttac tgttaaaact    360

gaggttattg gggtaactgc tatgttaaac ttgcattcag ggacacaaaa aactcatgaa    420

aatggtgctg gaaaacccat tcaagggtca aattttcatt tttttgctgt tggtggggaa    480

cctttggagc tgcagggtgt gttagcaaac tacaggacca aatatcctgc tcaaactgta    540

accccaaaaa atgctacagt tgacagtcag cagatgaaca ctgaccacaa ggctgttttg    600

gataaggata atgcttatcc agtggagtgc tgggttcctg atccaagtaa aaatgaaaac    660

actagatatt ttggaaccta cacaggtggg gaaaatgtgc ctcctgtttt gcacatcact    720

aacacagcaa ccacagtgct tcttgatgag cagggtgttg ggcccttgtg caaagctgac    780

agcttgtatg tttctgctgt tgacatttgt gggctgttta ccaacacttc tggaacacag    840

cagtggaagg gacttcccag atattttaaa attaccctta gaaagcggtc tgtgaaaaac    900

ccctacccaa tttccttttt gttaagtgac ctaattaaca ggaggacaca gagggtggat    960

gggcagccta tgattggaat gtcctctcaa gtagaggagg ttagggttta tgaggacaca   1020

gaggagcttc ctggggatcc agacatgata agatacattg atgagtttgg acaaaccaca   1080

actagaatgc agtga                                                    1095
```

<210> SEQ ID NO 26
<211> LENGTH: 364
<212> TYPE: PRT
<213> ORGANISM: Polyomavirus SV40

<400> SEQUENCE: 26

```
Met Lys Met Ala Pro Thr Lys Arg Lys Gly Ser Cys Pro Gly Ala Ala
1               5                   10                  15

Pro Lys Lys Pro Lys Glu Pro Val Gln Val Pro Lys Leu Val Ile Lys
            20                  25                  30

Gly Gly Ile Glu Val Leu Gly Val Lys Thr Gly Val Asp Ser Phe Thr
        35                  40                  45

Glu Val Glu Cys Phe Leu Asn Pro Gln Met Gly Asn Pro Asp Glu His
    50                  55                  60

Gln Lys Gly Leu Ser Lys Ser Leu Ala Ala Glu Lys Gln Phe Thr Asp
65                  70                  75                  80

Asp Ser Pro Asp Lys Asp Gln Leu Pro Cys Tyr Ser Val Ala Arg Ile
                85                  90                  95

Pro Leu Pro Asn Leu Asn Glu Asp Leu Thr Cys Gly Asn Ile Leu Met
            100                 105                 110

Trp Glu Ala Val Thr Val Lys Thr Glu Val Ile Gly Val Thr Ala Met
        115                 120                 125

Leu Asn Leu His Ser Gly Thr Gln Lys Thr His Glu Asn Gly Ala Gly
    130                 135                 140

Lys Pro Ile Gln Gly Ser Asn Phe His Phe Phe Ala Val Gly Gly Glu
145                 150                 155                 160

Pro Leu Glu Leu Gln Gly Val Leu Ala Asn Tyr Arg Thr Lys Tyr Pro
                165                 170                 175

Ala Gln Thr Val Thr Pro Lys Asn Ala Thr Val Asp Ser Gln Gln Met
            180                 185                 190

Asn Thr Asp His Lys Ala Val Leu Asp Lys Asp Asn Ala Tyr Pro Val
        195                 200                 205
```

-continued

```
Glu Cys Trp Val Pro Asp Pro Ser Lys Asn Glu Asn Thr Arg Tyr Phe
    210                 215                 220

Gly Thr Tyr Thr Gly Gly Glu Asn Val Pro Pro Val Leu His Ile Thr
225                 230                 235                 240

Asn Thr Ala Thr Thr Val Leu Leu Asp Glu Gln Gly Val Gly Pro Leu
                245                 250                 255

Cys Lys Ala Asp Ser Leu Tyr Val Ser Ala Val Asp Ile Cys Gly Leu
            260                 265                 270

Phe Thr Asn Thr Ser Gly Thr Gln Gln Trp Lys Gly Leu Pro Arg Tyr
        275                 280                 285

Phe Lys Ile Thr Leu Arg Lys Arg Ser Val Lys Asn Pro Tyr Pro Ile
    290                 295                 300

Ser Phe Leu Leu Ser Asp Leu Ile Asn Arg Arg Thr Gln Arg Val Asp
305                 310                 315                 320

Gly Gln Pro Met Ile Gly Met Ser Ser Gln Val Glu Glu Val Arg Val
                325                 330                 335

Tyr Glu Asp Thr Glu Glu Leu Pro Gly Asp Pro Asp Met Ile Arg Tyr
            340                 345                 350

Ile Asp Glu Phe Gly Gln Thr Thr Thr Arg Met Gln
        355                 360
```

<210> SEQ ID NO 27
<211> LENGTH: 1095
<212> TYPE: DNA
<213> ORGANISM: Polyomavirus SV40

<400> SEQUENCE: 27

```
atgaagatgg ccccaacaaa aagaaaagga agttgtccag gggcagctcc caaaaaacca     60

aaggaaccag tgcaagtgcc aaagctcgtc ataaaaggag gaatagaagt tctaggagtt    120

aaaactggag tagacagctt cactgaggtg gagtgctttt taaatcctca aatgggcaat    180

cctgatgaac atcaaaaagg cttaagtaaa agcttagcag ctgaaaaaca gtttacagat    240

gactctccag acaaagacca actgccttgc tacagtgtgg ctagaattcc tttgcctaat    300

ttaaatgagg acttaacctg tggaaatatt ttaatgtggg aagctgttac tgttaaaact    360

gaggttattg gggtaactgc tatgttaaac ttgcattcag ggacacaaaa aactcatgaa    420

aatggtgctg gaaaacccat acaagggtca aactttcatt tttttgctgt tggtggggaa    480

cctttggagc tgcagggtgt gttagcaaac tacaggacca aatatcctgc tcaaactgta    540

accccaaaaa atgctacagt tgacagtcag cagatgaaca ctgaccacaa ggctgttttg    600

gataaggata atgcttatcc agtggagtgc tgggttcctg atccaagtaa aaatgaaaac    660

actagatatt ttggaaccta cacaggtggg gaaaatgtgc ctcctgtttt acacattact    720

aacacagcaa ccacagtgct gcttgatgag cagggtgttg ggcccttgtg caaagctgac    780

agcttgtatg tttctgctgt tgacatttgt gggctgttta ccaacacttc tggaacacag    840

cagtggaagg gacttcccag atattttaaa attaccctta gaaagaggtc tgtgaaaaac    900

ccctacccaa tttccttttt gttaagtgac ctaattaaca ggaggacaca gagggtggat    960

gggcagccta tgattggaat gtcctctcaa gtagaggagg ttagggttta tgaggacaca   1020

gaggagcttc ctggggatcc agacatgata agatacattg atgagtttgg acaaaccaca   1080

actagaatgc agtga                                                    1095
```

<210> SEQ ID NO 28
<211> LENGTH: 1095

-continued

<212> TYPE: DNA
<213> ORGANISM: Polyomavirus SV40

<400> SEQUENCE: 28
atgaagatgg ccccaacaaa aagaaaagga agttgtccag gggcagctcc caaaaaacca 60
aaggaaccag tgcaagtgcc aaagctcgtc ataaaaggag gaatagaagt tctaggagtt 120
aaaactggag tagacagctt cactgaggtg gagtgctttt taaatcctca aatgggcaat 180
cctgatgaac atcaaaaagg cttaagtaaa agcttagcag ctgaaaaaca gtttacagat 240
gactctccag acaaagacca actgccttgc tacagtgtgg ctagaattcc tttgcctaat 300
ttaaatgagg acttaacctg tggaaatatt ttgatgtggg aagctgttac tgttaaaact 360
gaggttattg gggtaactgc tatgttaaac ttgcattcag ggacacaaaa aactcatgaa 420
aatggtgctg gaaaacccat acaagggtca aactttcatt tttttgctgt tggtggggaa 480
cctttggagc tgcagggtgt gttagcaaac tacaggacca aatatcctgc tcaaactgta 540
accccaaaaa atgctacagt tgacagtcag cagatgaaca ctgaccacaa ggctgttttg 600
gataaggata atgcttatcc agtggagtgc tgggttcctg atccaagtaa aaatgaaaac 660
actagatatt ttggaaccta cacaggtggg gaaaatgtgc ctcctgtttt gcacattact 720
aacacagcaa ccacagtgct gcttgatgag cagggtgttg ggcccttgtg caaagctgac 780
agcttgtatg tttctgctgt tgacatttgt gggctgttta ccaacacttc tggaacacag 840
cagtggaagg gacttcccag atattttaaa attaccctta gaaagaggtc tgtgaaaaac 900
ccctacccaa tttccttttt gttaagtgac ctaattaaca ggaggacaca gagggtggat 960
gggcagccta tgattggaat gtcctctcaa gtagaggagg ttagggttta tgaggacaca 1020
gaggagcttc ctggggatcc agacatgata agatacattg atgagtttgg acaaaccaca 1080
actagaatgc agtga 1095

<210> SEQ ID NO 29
<211> LENGTH: 1095
<212> TYPE: DNA
<213> ORGANISM: Polyomavirus SV40

<400> SEQUENCE: 29
atgaagatgg ccccaacaaa aagaaaagga agttgtccag gggcagctcc caaaaaacca 60
aaggaaccag tgcaagtgcc aaagctcgtc ataaaaggag gaatagaagt tctaggagtt 120
aaaactggag tagacagctt cactgaggtg gagtgctttt taaatcctca aatgggcaat 180
cctgatgaac atcaaaaagg cttaagtaaa agcttagcag ctgaaaaaca gtttacagat 240
gactctccag acaaagacca actgccttgc tacagtgtgg ctagaattcc tttgcctaat 300
ttaaatgagg acttaacctg tggaaatatt ttgatgtggg aagctgttac tgttaaaact 360
gaggttattg gggtaactgc tatgttaaac ttgcattcag ggacacaaaa aactcatgaa 420
aatggtgctg gaaaacccat acaagggtca aactttcatt tttttgctgt tggtggggaa 480
cctttggagc tgcagggtgt gttagcaaac tacaggacca aatatcctgc tcaaactgta 540
accccaaaaa atgctacagt tgacagtcag cagatgaaca ctgaccacaa ggctgttttg 600
gataaggata atgcttatcc agtggagtgc tgggttcctg atccaagtaa aaatgaaaac 660
actagatatt ttggaaccta cacaggtggg gaaaatgtgc ctcctgtttt gcacattact 720
aacacagcaa ccacagtgct gcttgatgag cagggtgttg ggcccttgtg caaagctgac 780
agcttgtatg tttctgctgt tgacatttgt gggctgttta ccaacacttc tggaacacag 840

```
cagtggaagg gacttcccag atattttaaa attaccctta gaaagcggtc tgtgaaaaac    900

ccctacccaa tttccttttt gttaagtgac ctaattaaca ggaggacaca gagggtggat    960

gggcagccta tgattggaat gtcctctcaa gtagaggagg ttagggttta tgaggacaca   1020

gaggagcttc ctggggatcc agacatgata agatacattg atgagtttgg acaaaccaca   1080

actagaatgc agtga                                                    1095


<210> SEQ ID NO 30
<211> LENGTH: 1095
<212> TYPE: DNA
<213> ORGANISM: Polyomavirus SV40

<400> SEQUENCE: 30

atgaagatgg ccccaacaaa aagaaaagga agttgtccag gggcagctcc caaaaaacca     60

aaggaaccag tgcaagtgcc aaagctcgtc ataaaaggag gaatagaagt tctaggagtt    120

aaaactggag tagacagctt cactgaggtg gagtgctttt taaatcctca aatgggcaat    180

cctgatgaac atcaaaaagg cttaagtaaa agcttagcag ctgaaaaaca gtttacagat    240

gactctccag acaaagacca actgccttgc tacagtgtgg ctagaattcc tttgcctaat    300

ttaaatgagg acttaacctg tggaaatatt ttgatgtggg aagctgttac tgttaaaact    360

gaggttattg ggtaactgc tatgttaaac ttgcattcag ggacacaaaa aactcatgaa    420

aatggtgctg gaaaacccat acaagggtca aactttcatt tttttgctgt tggtggggaa    480

cctttggagc tgcagggtgt gttagcaaac tacaggacca aatatcctgc tcaaactgta    540

accccaaaaa atgctacagt tgacagtcag cagatgaaca ctgaccacaa ggctgttttg    600

gataaggata atgcttatcc agtggagtgc tgggttcctg atccaagtaa aaatgaaaac    660

actagatatt ttggaaccta cacaggtggg gaaaatgtgc ctcctgtttt acacattact    720

aacacagcaa ccacagtgct gcttgatgag cagggtgttg ggcccttgtg caaagctgac    780

agcttgtatg tttctgctgt tgacatttgt gggctgttta ccaacacttc tggaacacag    840

cagtggaagg gacttcccag atattttaaa attaccctta gaaagaggtc tgtgaaaaac    900

ccctacccaa tttccttttt gttaagtgac ctaattaaca ggaggacaca gagggtggat    960

gggcagccta tgattggaat gtcctctcaa gtagaggagg ttagggttta tgaggacaca   1020

gaggagcttc ctggggatcc agacatgata agatacattg atgagtttgg acaaaccaca   1080

actagaatgc agtga                                                    1095


<210> SEQ ID NO 31
<211> LENGTH: 1095
<212> TYPE: DNA
<213> ORGANISM: Polyomavirus SV40

<400> SEQUENCE: 31

atgaagatgg ccccaacaaa aagaaaagga agttgtccag gggcagctcc caaaaaacca     60

aaggaaccag tgcaagtgcc aaagctcgtc ataaaaggag gaatagaagt tctaggagtt    120

aaaactggag tagacagctt cactgaggtg gagtgctttt taaatcctca aatgggcaat    180

cctgatgaac atcaaaaagg cttaagtaaa agcttagcag ctgaaaaaca gtttacagat    240

gactctccag acaaagacca actgccttgc tacagtgtgg ctagaattcc tttgcctaat    300

ttaaatgagg acttaacctg tggaaatatt ttgatgtggg aagctgttac tgttaaaact    360

gaggttattg ggtaactgc tatgttaaac ttgcattcag ggacacaaaa aactcatgaa    420

aatggtgctg gaaaacccat acaagggtca aactttcatt tttttgctgt tggtggggaa    480
```

-continued

```
cctttggagc tgcagggtgt gttagcaaac tacaggacca aatatcctgc tcaaactgta    540

acccccaaaa atgctacagt tgacagtcag cagatgaaca ctgaccacaa ggctgttttg    600

gataaggata atgcttatcc agtggagtgc tgggttcctg atccaagtaa aaatgaaaac    660

actagatatt ttggaaccta cacaggtggg gaaaatgtgc ctcctgtttt gcacattact    720

aacacagcaa ccacagtgct gcttgatgag cagggtgttg ggcccttgtg caaagctgac    780

agcttgtatg tttctgctgt tgacatttgt gggctgttta ccaacacttc tggaacacag    840

cagtggaagg gacttcccag atattttaaa attaccctta gaaagcggtc tgtgaaaaac    900

ccctacccaa tttccttttt gttaagtgac ctaattaaca ggaggacaca gagggtggat    960

gggcagccta tgattggaat gtcctctcaa gtagaggagg ttagggttta tgaggacaca   1020

gaggagcttc ctggggatcc agacatgata agatacattg atgagtttgg acaaaccaca   1080

actagaatgc agtga                                                    1095
```

```
<210> SEQ ID NO 32
<211> LENGTH: 1095
<212> TYPE: DNA
<213> ORGANISM: Polyomavirus SV40

<400> SEQUENCE: 32

atgaagatgg ccccaacaaa aagaaaagga agttgtccag gggcagctcc caaaaaacca     60

aaggaaccag tgcaagtgcc aaagctcgtc ataaaaggag gaatagaagt tctaggagtt    120

aaaactggag tagacagctt cactgaggtg gagtgctttt taaatcctca aatgggcaat    180

cctgatgaac atcaaaaagg cttaagtaaa agcttagcag ctgaaaaaca gtttacagat    240

gactctccag acaaagacca actgccttgc tacagtgtgg ctagaattcc tttgcctaat    300

ttaaatgagg acttaacctg tggaaatatt ttgatgtggg aagctgttac tgttaaaact    360

gaggttattg gggtaactgc tatgttaaac ttgcattcag ggacacaaaa aactcatgaa    420

aatggtgctg gaaaacccat acaagggtca aactttcatt tttttgctgt tggtggggaa    480

cctttggagc tgcagggtgt gttagcaaac tacaggacca aatatcctgc tcaaactgta    540

acccccaaaa atgctacagt tgacagtcag cagatgaaca ctgaccacaa ggctgttttg    600

gataaggata atgcttatcc agtggagtgc tgggttcctg atccaagtaa aaatgaaaac    660

actagatatt ttggaaccta cacaggtggg gaaaatgtgc ctcctgtttt gcacattact    720

aacacagcaa ccacagtgct gcttgatgag cagggtgttg ggcccttgtg caaagctgac    780

agcttgtatg tttctgctgt tgacatttgt gggctgttta ccaacacttc tggaacacag    840

cagtggaagg gacttcccag atattttaaa attaccctta gaaagcggtc tgtgaaaaac    900

ccctacccaa tttccttttt gttaagtgac ctaattaaca ggaggacaca gagggtggat    960

gggcagccta tgattggaat gtcctctcaa gtagaggagg ttagggttta tgaggacaca   1020

gaggagcttc ctggggatcc agacatgata agatacattg atgagtttgg acaaaccaca   1080

acaagaatgc agtga                                                    1095
```

```
<210> SEQ ID NO 33
<211> LENGTH: 364
<212> TYPE: PRT
<213> ORGANISM: Polyomavirus SV40

<400> SEQUENCE: 33

Met Lys Met Ala Pro Thr Lys Arg Lys Gly Ser Cys Pro Gly Ala Ala
1               5                   10                  15
```

```
Pro Lys Lys Pro Lys Glu Pro Val Gln Val Pro Lys Leu Val Ile Lys
            20                  25                  30

Gly Gly Ile Glu Val Leu Gly Val Lys Thr Gly Val Asp Ser Phe Thr
        35                  40                  45

Glu Val Glu Cys Phe Leu Asn Pro Gln Met Gly Asn Pro Asp Glu His
    50                  55                  60

Gln Lys Gly Leu Ser Lys Ser Leu Ala Ala Glu Lys Gln Phe Thr Asn
65                  70                  75                  80

Asp Ser Pro Asp Lys Asp Gln Leu Pro Cys Tyr Ser Val Ala Arg Ile
                85                  90                  95

Pro Leu Pro Asn Leu Asn Glu Asp Leu Thr Cys Gly Asn Ile Leu Met
            100                 105                 110

Trp Glu Ala Val Thr Val Lys Thr Glu Val Ile Gly Val Thr Ala Met
        115                 120                 125

Leu Asn Leu His Ser Gly Thr Gln Lys Thr His Glu Asn Gly Ala Gly
    130                 135                 140

Lys Pro Ile Gln Gly Ser Asn Phe Gln Phe Phe Ala Val Gly Gly Glu
145                 150                 155                 160

Pro Leu Glu Leu Gln Gly Val Leu Ala Asn Tyr Arg Thr Lys Tyr Pro
                165                 170                 175

Ala Gln Thr Val Thr Pro Lys Asn Ala Thr Val Asp Ser Gln Gln Met
            180                 185                 190

Asn Thr Asp His Lys Ala Val Leu Asp Lys Asp Asn Ala Tyr Pro Val
        195                 200                 205

Glu Cys Trp Val Pro Asp Pro Ser Lys Asn Glu Asn Thr Arg Tyr Phe
    210                 215                 220

Gly Thr Tyr Thr Gly Gly Glu Asn Val Pro Pro Val Leu His Ile Thr
225                 230                 235                 240

Asn Thr Ala Thr Thr Val Leu Leu Asp Glu Gln Gly Val Gly Pro Leu
                245                 250                 255

Cys Lys Ala Asp Ser Leu Tyr Val Ser Ala Val Asp Ile Cys Gly Leu
            260                 265                 270

Phe Thr Asn Thr Ser Gly Thr Gln Gln Trp Lys Gly Leu Pro Arg Tyr
        275                 280                 285

Phe Lys Ile Thr Leu Arg Lys Arg Ser Val Lys Asn Pro Tyr Pro Ile
    290                 295                 300

Ser Phe Leu Leu Ser Asp Leu Ile Asn Arg Arg Thr Gln Arg Val Asp
305                 310                 315                 320

Gly Gln Pro Met Ile Gly Met Ser Ser Gln Val Glu Glu Val Arg Val
                325                 330                 335

Tyr Glu Asp Thr Glu Glu Leu Pro Gly Asp Pro Asp Met Ile Arg Tyr
            340                 345                 350

Ile Asp Glu Phe Gly Gln Thr Thr Thr Arg Met Gln
        355                 360
```

<210> SEQ ID NO 34
<211> LENGTH: 1095
<212> TYPE: DNA
<213> ORGANISM: Polyomavirus SV40

<400> SEQUENCE: 34

```
atgaagatgg ccccaacaaa aagaaaagga agttgtccag gggcagctcc caaaaaacca      60

aaggaaccag tgcaagtgcc aaagctcgtc ataaaaggag gaatagaagt tctaggagtt     120
```

-continued

```
aaaactggag tagacagctt cactgaggtg gagtgctttt taaatcctca aatgggcaat    180

cctgatgaac atcaaaaagg cttaagtaaa agcttagcag ctgaaaaaca gtttacaaat    240

gactctccag acaaagacca actgccttgc tacagtgtgg ctagaattcc tttgcctaat    300

ttaaatgagg acttaacctg tggaaatatt ttgatgtggg aagctgttac tgttaaaact    360

gaggttattg gggtaactgc tatgttaaac ttgcattcag ggacacaaaa aactcatgaa    420

aatggtgctg gaaaacccat acaagggtca aactttcagt tttttgctgt tggtggggaa    480

cctttggagc tgcagggtgt gttagcaaac tacaggacca aatatcctgc tcaaactgta    540

accccaaaaa atgctacagt tgacagtcag cagatgaaca ctgaccacaa ggctgttttg    600

gataaggata atgcttatcc agtggagtgc tgggttcctg atccaagtaa aaatgaaaac    660

actagatatt ttggaaccta cacaggtggg gaaaatgtgc ctcctgtttt gcacattact    720

aacacagcaa ccacagtgct gcttgatgag cagggtgttg ggcccttgtg caaagctgac    780

agcttgtatg tttctgctgt tgacatttgt gggctgttta ccaacacttc tggaacacag    840

cagtggaagg gacttcccag atattttaaa attaccctta gaaagaggtc tgtgaaaaac    900

ccctacccaa tttccttttt gttaagtgac ctaattaaca ggaggacaca gagggtggat    960

gggcagccta tgattggaat gtcctctcaa gtagaggagg ttagggttta tgaggacaca   1020

gaggagcttc ctggggatcc agacatgata agatacattg atgagtttgg acaaaccaca   1080

actagaatgc agtga                                                    1095


<210> SEQ ID NO 35
<211> LENGTH: 364
<212> TYPE: PRT
<213> ORGANISM: Polyomavirus SV40

<400> SEQUENCE: 35

Met Lys Met Ala Pro Thr Lys Arg Lys Gly Ser Cys Pro Gly Ala Ala
1               5                   10                  15

Pro Lys Lys Pro Lys Glu Pro Val Gln Val Pro Lys Leu Val Ile Lys
            20                  25                  30

Gly Gly Ile Glu Val Leu Gly Val Lys Thr Gly Val Asp Ser Phe Thr
        35                  40                  45

Glu Val Glu Cys Phe Leu Asn Pro Gln Met Gly Asn Pro Asp Glu His
    50                  55                  60

Gln Lys Gly Leu Ser Lys Ser Leu Ala Ala Glu Lys Lys Phe Thr Asp
65                  70                  75                  80

Asp Ser Pro Asp Lys Asp Gln Leu Pro Cys Tyr Ser Val Ala Arg Ile
                85                  90                  95

Pro Leu Pro Asn Leu Asn Glu Asp Leu Thr Cys Gly Asn Ile Leu Met
            100                 105                 110

Trp Glu Ala Val Thr Val Lys Thr Glu Val Ile Gly Val Thr Ala Met
        115                 120                 125

Leu Asn Leu His Ser Gly Thr Gln Lys Thr His Glu Asn Gly Ala Gly
    130                 135                 140

Lys Pro Ile Gln Gly Ser Asn Phe His Phe Phe Ala Val Gly Gly Glu
145                 150                 155                 160

Pro Leu Glu Leu Gln Gly Val Leu Ala Asn Tyr Arg Thr Lys Tyr Pro
                165                 170                 175

Ala Gln Thr Val Thr Pro Lys Asn Ala Thr Phe Asp Ser Gln Gln Met
            180                 185                 190

Asn Thr Asp His Lys Ala Val Leu Asp Lys Asp Asn Ala Tyr Pro Val
```

-continued

```
        195                 200                 205

Glu Cys Trp Val Pro Asp Pro Ser Lys Asn Glu Asn Thr Arg Tyr Phe
    210                 215                 220

Gly Thr Tyr Thr Gly Gly Glu Asn Val Pro Pro Val Leu His Ile Thr
225                 230                 235                 240

Asn Thr Ala Thr Thr Val Leu Leu Asp Glu Gln Gly Val Gly Pro Leu
                245                 250                 255

Cys Lys Ala Asp Ser Leu Tyr Val Ser Ala Val Asp Ile Cys Gly Leu
            260                 265                 270

Phe Thr Asn Thr Ser Gly Thr Gln Gln Trp Lys Gly Leu Pro Arg Tyr
        275                 280                 285

Phe Lys Ile Thr Leu Arg Lys Arg Ser Val Lys Asn Pro Tyr Pro Ile
    290                 295                 300

Ser Phe Leu Leu Ser Asp Leu Ile Asn Arg Arg Thr Gln Arg Val Asp
305                 310                 315                 320

Gly Gln Pro Met Ile Gly Met Ser Ser Gln Val Glu Glu Val Arg Val
                325                 330                 335

Tyr Glu Asp Thr Glu Glu Leu Pro Gly Asp Pro Asp Met Ile Arg Tyr
            340                 345                 350

Ile Asp Glu Phe Gly Gln Thr Thr Thr Arg Met Gln
        355                 360


<210> SEQ ID NO 36
<211> LENGTH: 1095
<212> TYPE: DNA
<213> ORGANISM: Polyomavirus SV40

<400> SEQUENCE: 36

atgaagatgg ccccaacaaa aagaaaagga agttgtccag gggcagctcc caaaaaacca      60

aaggaaccag tgcaagtgcc aaagctcgtc ataaaaggag gaatagaagt tctaggagtt     120

aaaactggag tagacagctt cactgaggtg gagtgctttt taaatcctca aatgggcaat     180

cctgatgaac atcaaaaagg cttaagtaaa agcttagcag ctgaaaaaaa gtttacagat     240

gactctccag acaaagacca actgccttgc tacagtgtgg ctagaattcc tttgcctaat     300

ttaaatgagg acttaacctg tggaaatatt ttgatgtggg aagctgttac tgttaaaact     360

gaggttattg gggtaactgc tatgttaaac ttgcattcag ggacacaaaa aactcatgaa     420

aatggtgctg gaaaacccat acaagggtca aactttcatt tttttgctgt tggtggggaa     480

cctttggagc tgcagggtgt gttagcaaac tacaggacca aatatcctgc tcaaactgta     540

accccaaaaa atgctacatt tgacagtcag cagatgaaca ctgaccacaa ggctgttttg     600

gataaggata atgcttatcc agtggagtgc tgggttcctg atccaagtaa aaatgaaaac     660

actagatatt ttggaaccta cacaggtggg gaaaatgtgc ctcctgtttt acacattact     720

aacacagcaa ccacagtgct gcttgatgag cagggtgttg ggcccttgtg caaagctgac     780

agcttgtatg tttctgctgt tgacatttgt gggctgttta ccaacacttc tggaacacag     840

cagtggaagg gacttcccag atattttaaa attaccctta gaaagaggtc tgtgaaaaac     900

ccctacccaa tttccttttt gttaagtgac ctaattaaca ggaggacaca gagggtggat     960

gggcagccta tgattggaat gtcctctcaa gtagaggagg ttagggttta tgaggacaca    1020

gaggagcttc ctggggatcc agacatgata agatacattg atgagtttgg acaaaccaca    1080

actagaatgc agtga                                                     1095
```

<210> SEQ ID NO 37
<211> LENGTH: 364
<212> TYPE: PRT
<213> ORGANISM: Polyomavirus SV40

<400> SEQUENCE: 37

```
Met Lys Met Ala Pro Thr Lys Arg Lys Gly Ser Cys Pro Gly Ala Ala
1               5                   10                  15

Pro Lys Lys Pro Lys Glu Pro Val Gln Val Pro Lys Leu Val Ile Lys
            20                  25                  30

Gly Gly Ile Glu Val Leu Gly Val Lys Thr Gly Val Asp Ser Phe Thr
        35                  40                  45

Glu Val Glu Cys Phe Leu Asn Pro Gln Met Gly Asn Pro Asp Glu His
    50                  55                  60

Gln Lys Gly Leu Ser Lys Ser Leu Ala Ala Glu Lys Gln Phe Thr Asp
65                  70                  75                  80

Asp Ser Pro Asp Lys Asp Gln Leu Pro Cys Tyr Ser Val Ala Arg Ile
                85                  90                  95

Pro Leu Pro Asn Leu Asn Glu Asp Leu Thr Cys Gly Asn Ile Leu Met
            100                 105                 110

Trp Glu Ala Val Thr Val Lys Thr Glu Val Ile Gly Val Thr Ala Met
        115                 120                 125

Leu Asn Leu His Ser Gly Thr Gln Lys Thr Tyr Glu Asn Gly Ala Gly
    130                 135                 140

Lys Pro Ile Gln Gly Ser Asn Phe His Phe Phe Ala Val Gly Gly Glu
145                 150                 155                 160

Pro Leu Glu Leu Gln Gly Val Leu Ala Asn Tyr Arg Thr Lys Tyr Pro
                165                 170                 175

Ala Gln Thr Val Thr Pro Lys Asn Ala Thr Val Asp Ser Gln Gln Met
            180                 185                 190

Asn Thr Asp His Lys Ala Val Leu Asp Lys Asp Asn Ala Tyr Pro Val
        195                 200                 205

Glu Cys Trp Val Pro Asp Pro Ser Lys Asn Glu Asn Thr Arg Tyr Phe
    210                 215                 220

Gly Thr Tyr Thr Gly Gly Glu Asn Val Pro Pro Val Leu His Ile Thr
225                 230                 235                 240

Asn Thr Ala Thr Thr Val Leu Leu Asp Glu Gln Gly Val Gly Pro Leu
                245                 250                 255

Cys Lys Ala Asp Ser Leu Tyr Val Ser Ala Val Asp Ile Cys Gly Leu
            260                 265                 270

Phe Thr Asn Thr Ser Gly Thr Gln Gln Trp Lys Gly Leu Pro Arg Tyr
        275                 280                 285

Phe Lys Ile Thr Leu Arg Lys Arg Ser Val Lys Asn Pro Tyr Pro Ile
    290                 295                 300

Ser Phe Leu Leu Ser Asp Leu Ile Asn Arg Arg Thr Gln Arg Val Asp
305                 310                 315                 320

Gly Gln Pro Met Ile Gly Met Ser Ser Gln Val Glu Glu Val Arg Val
                325                 330                 335

Tyr Glu Asp Thr Glu Glu Leu Pro Gly Asp Pro Asp Met Ile Arg Tyr
            340                 345                 350

Ile Asp Glu Phe Gly Gln Thr Thr Thr Arg Met Gln
        355                 360
```

<210> SEQ ID NO 38
<211> LENGTH: 1095

<212> TYPE: DNA
<213> ORGANISM: Polyomavirus SV40

<400> SEQUENCE: 38
atgaagatgg ccccaacaaa aagaaaagga agttgtccag gggcagctcc caaaaaacca 60
aaggaaccag tgcaagtgcc aaagctcgtc ataaaaggag gaatagaagt tctaggagtt 120
aaaactggag tagacagctt cactgaggtg gagtgctttt taaatcctca aatgggcaat 180
cctgatgaac atcaaaaagg cttaagtaaa agcttagcag ctgaaaaaca gtttacagat 240
gactctccag acaaagacca actgccttgc tacagtgtgg ctagaattcc tttgcctaat 300
ttaaatgagg acttaacctg tggaaatatt ttgatgtggg aagctgttac tgttaaaact 360
gaggttattg gggtaactgc tatgttaaac ttgcattcag ggacacaaaa aacttatgaa 420
aatggtgctg gaaaacccat acaagggtca aactttcatt tttttgctgt tggtggggaa 480
cctttggagc tgcagggtgt gttagcaaac tacaggacca aatatcctgc tcaaactgta 540
accccaaaaa atgctacagt tgacagtcag cagatgaaca ctgaccacaa ggctgttttg 600
gataaggata atgcttatcc agtggagtgc tgggttcctg atccaagtaa aaatgaaaac 660
actagatatt ttggaaccta cacaggtggg gaaaatgtgc ctcctgtttt acacattact 720
aacacagcaa ccacagtgct gcttgatgag cagggtgttg ggcccttgtg caaagctgac 780
agcttgtatg tttctgctgt tgacatttgt gggctgttta ccaacacttc tggaacacag 840
cagtggaagg gacttcccag atattttaaa attaccctta gaaagaggtc tgtgaaaaac 900
ccctacccaa tttccttttt gttaagtgac ctaattaaca ggaggacaca gagggtggat 960
gggcagccta tgattggaat gtcctctcaa gtagaggagg ttagggttta tgaggacaca 1020
gaggagcttc ctggggatcc agacatgata agatacattg atgagtttgg acaaaccaca 1080
actagaatgc agtga 1095

<210> SEQ ID NO 39
<211> LENGTH: 364
<212> TYPE: PRT
<213> ORGANISM: Polyomavirus SV40

<400> SEQUENCE: 39

Met Lys Met Ala Pro Thr Lys Arg Lys Gly Ser Cys Pro Gly Ala Ala
1 5 10 15

Pro Lys Lys Pro Lys Glu Pro Val Gln Val Pro Lys Leu Val Ile Lys
20 25 30

Gly Gly Ile Glu Val Leu Gly Val Lys Thr Gly Val Asp Ser Phe Thr
35 40 45

Glu Val Glu Cys Phe Leu Asn Pro Gln Met Gly Asn Pro Asp Glu His
50 55 60

Gln Lys Gly Leu Ser Lys Ser Leu Ala Ala Glu Lys Gln Phe Thr Asp
65 70 75 80

Asp Ser Pro Asp Lys Asp Gln Leu Pro Cys Tyr Ser Val Ala Arg Ile
85 90 95

Pro Leu Pro Asn Leu Asn Glu Asp Leu Thr Cys Gly Asn Ile Leu Met
100 105 110

Trp Glu Ala Val Thr Val Lys Thr Glu Val Ile Gly Val Thr Ala Met
115 120 125

Leu Asn Leu His Ser Gly Thr Gln Lys Thr His Glu Asn Gly Ala Gly
130 135 140

Lys Pro Ile Gln Gly Ser Asn Phe His Phe Phe Ala Val Gly Gly Glu

-continued

```
145                 150                 155                 160

Pro Leu Glu Leu Gln Gly Val Leu Ala Asn Tyr Arg Thr Lys Tyr Pro
                165                 170                 175

Ala Gln Thr Val Thr Pro Lys Asn Ala Thr Val Asp Ser Gln Gln Met
            180                 185                 190

Asn Thr Asp His Lys Ala Val Leu Asp Lys Asp Asn Ala Tyr Pro Val
        195                 200                 205

Glu Cys Trp Val Pro Asp Pro Ser Lys Asn Glu Asn Thr Arg Tyr Phe
    210                 215                 220

Gly Thr Tyr Thr Gly Gly Glu Asn Val Pro Pro Val Leu His Ile Thr
225                 230                 235                 240

Asn Thr Ala Thr Thr Val Leu Leu Asp Glu Gln Gly Val Gly Pro Leu
                245                 250                 255

Tyr Lys Ala Asp Ser Leu Tyr Val Ser Ala Val Asp Ile Cys Gly Leu
            260                 265                 270

Phe Thr Asn Thr Ser Gly Thr Gln Gln Trp Lys Gly Leu Pro Arg Tyr
        275                 280                 285

Phe Lys Ile Thr Leu Arg Lys Arg Ser Val Lys Asn Pro Tyr Pro Ile
    290                 295                 300

Ser Phe Leu Leu Ser Asp Leu Ile Asn Arg Arg Thr Gln Arg Val Asp
305                 310                 315                 320

Gly Gln Pro Met Ile Gly Met Ser Ser Gln Val Glu Glu Val Arg Val
                325                 330                 335

Tyr Glu Asp Thr Glu Glu Leu Pro Gly Asp Pro Asp Met Ile Arg Tyr
            340                 345                 350

Ile Asp Glu Phe Gly Gln Thr Thr Thr Arg Met Gln
        355                 360


<210> SEQ ID NO 40
<211> LENGTH: 1095
<212> TYPE: DNA
<213> ORGANISM: Polyomavirus SV40

<400> SEQUENCE: 40

atgaagatgg ccccaacaaa aagaaaagga agttgtccag gggcagctcc caaaaaacca      60

aaggaaccag tgcaagtgcc aaagctcgtc ataaaaggag gaatagaagt tctaggagtt     120

aaaactggag tagacagctt cactgaggtg gagtgctttt taaatcctca aatgggcaat     180

cctgatgaac atcaaaaagg cttaagtaaa agcttagcag ctgaaaaaca gtttacagat     240

gactctccag acaaagacca actgccttgc tacagtgtgg ctagaattcc tttgcctaat     300

ttaaatgagg acttaacctg tggaaatatt ttgatgtggg aagctgttac tgttaaaact     360

gaggttattg gggtaactgc tatgttaaac ttgcattcag ggacacaaaa aactcatgaa     420

aatggtgctg gaaaacccat acaagggtca aactttcatt tttttgctgt tggtggggaa     480

cctttggagc tgcagggtgt gttagcaaac tacaggacca aatatcctgc tcaaactgta     540

accccaaaaa atgctacagt tgacagtcag cagatgaaca ctgaccacaa ggctgttttg     600

gataaggata atgcttatcc agtggagtgc tgggttcctg atccaagtaa aaatgaaaac     660

actagatatt ttggaaccta cacaggtggg gaaaatgtgc ctcctgtttt gcacattact     720

aacacagcaa ccacagtgct gcttgatgag cagggtgttg ggcccttgta caaagctgac     780

agcttgtatg tttctgctgt tgacatttgt gggctgttta ccaacacttc tggaacacag     840

cagtggaagg gacttcccag atattttaaa attaccctta gaaagcggtc tgtgaaaaac     900
```

-continued

```
ccctacccaa tttccttttt gttaagtgac ctaattaaca ggaggacaca gagggtggat    960

gggcagccta tgattggaat gtcctctcaa gtagaggagg ttagggttta tgaggacaca   1020

gaggagcttc ctggggatcc agacatgata agatacattg atgagtttgg acaaaccaca   1080

actagaatgc agtga                                                    1095


<210> SEQ ID NO 41
<211> LENGTH: 364
<212> TYPE: PRT
<213> ORGANISM: Polyomavirus SV40

<400> SEQUENCE: 41

Met Lys Met Ala Pro Thr Lys Arg Lys Gly Ser Cys Pro Gly Ala Ala
1               5                   10                  15

Pro Lys Lys Pro Lys Glu Pro Val Gln Val Pro Lys Leu Val Ile Lys
            20                  25                  30

Gly Gly Ile Glu Val Leu Gly Val Lys Thr Gly Val Asp Ser Phe Thr
        35                  40                  45

Glu Val Glu Cys Phe Leu Asn Pro Gln Met Gly Asn Pro Asp Glu His
    50                  55                  60

Gln Lys Gly Leu Ser Lys Ser Val Ala Ala Glu Lys Gln Phe Thr Asp
65                  70                  75                  80

Asp Ser Pro Asp Lys Asp Gln Leu Pro Cys Tyr Ser Val Ala Arg Ile
                85                  90                  95

Pro Leu Pro Asn Leu Asn Glu Asp Leu Thr Cys Gly Asn Ile Leu Met
            100                 105                 110

Trp Glu Ala Val Thr Val Lys Thr Glu Val Ile Gly Val Thr Ala Met
        115                 120                 125

Leu Asn Leu His Ser Gly Thr Gln Lys Thr His Glu Asn Gly Ala Gly
    130                 135                 140

Lys Pro Ile Gln Gly Ser Asn Phe His Phe Phe Ala Val Val Gly Glu
145                 150                 155                 160

Pro Leu Glu Leu Gln Gly Val Leu Ala Asn Cys Ser Thr Lys Tyr Pro
                165                 170                 175

Ala Gln Thr Val Thr Pro Lys Asn Ala Thr Val Asp Ser Gln Gln Met
            180                 185                 190

Asn Thr Asp His Lys Ala Val Leu Asp Lys Asp Asn Ala Tyr Pro Val
        195                 200                 205

Glu Cys Trp Val Pro Asp Pro Ser Lys Asn Glu Asn Thr Arg Tyr Phe
    210                 215                 220

Gly Thr Tyr Thr Gly Gly Glu Asn Val Pro Pro Val Leu His Ile Thr
225                 230                 235                 240

Asn Thr Ala Thr Thr Val Leu Leu Asp Glu Gln Gly Val Gly Pro Leu
                245                 250                 255

Cys Lys Ala Asp Ser Leu Tyr Val Ser Ala Val Asp Ile Cys Gly Leu
            260                 265                 270

Phe Thr Asn Thr Ser Gly Thr Gln Gln Trp Lys Gly Leu Pro Arg Tyr
        275                 280                 285

Phe Lys Ile Thr Leu Arg Lys Arg Ser Val Lys Asn Pro Tyr Pro Ile
    290                 295                 300

Ser Phe Leu Leu Ser Asp Leu Ile Asn Arg Arg Thr Gln Arg Val Asp
305                 310                 315                 320

Gly Gln Pro Met Ile Gly Met Ser Ser Gln Val Glu Glu Val Arg Val
                325                 330                 335
```

Tyr Glu Asp Thr Glu Glu Leu Pro Gly Asp Pro Asp Met Ile Arg Tyr
340 345 350

Ile Asp Glu Phe Gly Gln Thr Thr Thr Arg Met Gln
355 360

<210> SEQ ID NO 42
<211> LENGTH: 1095
<212> TYPE: DNA
<213> ORGANISM: Polyomavirus SV40

<400> SEQUENCE: 42
atgaagatgg ccccaacaaa aagaaaagga agttgtccag gggcagctcc caaaaaacca 60
aaggaaccag tgcaagtgcc aaagctcgtc ataaaaggag gaatagaagt tctaggagtt 120
aaaactggag tagacagctt cactgaggtg gagtgctttt taaatcctca aatgggcaat 180
cctgatgaac atcaaaaagg cttaagtaaa agcgtagcag ctgaaaaaca gtttacagat 240
gactctccag acaaagacca actgccttgc tacagtgtgg ctagaattcc tttgcctaat 300
ttaaatgagg acttaacctg tggaaatatt ttgatgtggg aagctgttac tgttaaaact 360
gaggttattg gggtaactgc tatgttaaac ttgcattcag ggacacaaaa aactcatgaa 420
aatggtgctg gaaaacccat acaagggtca aactttcatt tttttgctgt tgttggggaa 480
cctttggagc tgcagggtgt gttagcaaac tgcagtacca aataccctgc tcaaactgta 540
accccaaaaa atgctacagt tgacagtcag cagatgaaca ctgaccacaa ggctgttttg 600
gataaggata atgcttatcc agtggagtgc tgggttcctg atccaagtaa aaatgaaaac 660
actagatatt ttggaaccta cacaggtggg gaaaatgtgc ctcctgtttt gcacattact 720
aacacagcaa ccacagtgct gcttgatgag cagggtgttg ggcccttgtg caaagctgac 780
agcttgtatg tttctgctgt tgacatttgt gggctgttta ccaacacttc tggaacacag 840
cagtggaagg gacttcccag atattttaaa attaccctta gaaagaggtc tgtgaaaaac 900
ccctacccaa tttccttttt gttaagtgac ctaattaaca ggaggacaca gagggtggat 960
gggcagccta tgattggaat gtcctctcaa gtagaggagg ttagggttta tgaggacaca 1020
gaggagcttc ctggggatcc agacatgata agatacattg atgagtttgg acaaaccaca 1080
actagaatgc agtga 1095

<210> SEQ ID NO 43
<211> LENGTH: 364
<212> TYPE: PRT
<213> ORGANISM: Polyomavirus SV40

<400> SEQUENCE: 43

Met Lys Met Ala Pro Ala Lys Arg Lys Gly Ser Cys Pro Gly Ala Ala
1 5 10 15

Pro Lys Lys Pro Lys Glu Pro Val Gln Val Pro Lys Leu Val Ile Lys
20 25 30

Gly Gly Ile Glu Val Leu Gly Val Lys Thr Gly Val Asp Ser Phe Thr
35 40 45

Glu Val Glu Cys Phe Leu Asn Pro Gln Met Gly Asn Pro Asp Glu His
50 55 60

Gln Lys Gly Leu Ser Lys Ser Leu Ala Ala Glu Lys Gln Phe Thr Asp
65 70 75 80

Asp Ser Pro Glu Lys Asp Gln Leu Pro Cys Tyr Ser Val Ala Arg Ile
85 90 95

Pro Leu Pro Asn Leu Asn Glu Asp Leu Thr Cys Gly Asn Ile Leu Met

```
            100                 105                 110

Trp Glu Ala Val Thr Val Lys Thr Glu Val Ile Gly Val Thr Cys Met
        115                 120                 125

Leu Asn Leu His Ser Gly Thr Gln Lys Thr His Glu Asn Gly Ala Gly
    130                 135                 140

Lys Pro Ile Gln Gly Ser Asn Phe His Phe Phe Ala Ile Gly Gly Glu
145                 150                 155                 160

Pro Leu Glu Leu Gln Gly Val Leu Ala Asn Tyr Arg Thr Lys Tyr Pro
                165                 170                 175

Ala Leu Thr Val Thr Pro Lys Asn Ala Thr Ser Asp Ser Gln Gln Met
            180                 185                 190

Asn Thr Asp His Lys Ala Val Leu Asp Lys Asp Asn Ala Tyr Pro Ile
        195                 200                 205

Glu Cys Trp Val Pro Asp Pro Ser Lys Asn Glu Asn Thr Arg Tyr Phe
    210                 215                 220

Gly Thr Tyr Thr Gly Gly Glu Asn Val Pro Pro Val Leu His Ile Thr
225                 230                 235                 240

Asn Thr Ala Thr Thr Val Leu Leu Asp Glu Gln Gly Val Gly Pro Leu
                245                 250                 255

Cys Lys Ala Asp Ser Leu Tyr Val Ser Ala Ala Asp Ile Cys Gly Leu
            260                 265                 270

Phe Thr Asn Thr Ser Gly Thr Gln Gln Trp Lys Gly Leu Pro Arg Tyr
        275                 280                 285

Phe Lys Ile Thr Leu Arg Lys Arg Ser Val Lys Asn Pro Tyr Pro Ile
    290                 295                 300

Ser Phe Leu Leu Ser Asp Leu Ile Asn Arg Arg Thr Gln Arg Val Asp
305                 310                 315                 320

Gly Gln Pro Met Ile Gly Met Ser Ser Gln Val Glu Glu Val Arg Val
                325                 330                 335

Tyr Glu Asp Thr Glu Glu Leu Pro Gly Asp Pro Asp Met Ile Arg Tyr
            340                 345                 350

Ile Asp Glu Phe Gly Gln Thr Thr Thr Arg Met Gln
        355                 360


<210> SEQ ID NO 44
<211> LENGTH: 1095
<212> TYPE: DNA
<213> ORGANISM: Polyomavirus SV40

<400> SEQUENCE: 44

atgaagatgg ccccagcaaa aagaaaagga agctgtccag gggcagctcc caaaaaacca      60

aaggaaccag ttcaagtacc aaagctcgtc ataaaaggag gaatagaagt tctaggagtt     120

aaaactggag tagacagctt tactgaggtg gagtgctttt taaatcctca aatgggcaat     180

cctgatgaac accaaaaagg cttaagtaaa agcctagctg ctgaaaagca gtttactgat     240

gactctccag aaaaggacca gctgccctgc tacagtgtgg ccagaattcc attgcctaat     300

ttaaatgagg accttacctg tggaaatatt ttaatgtggg aagctgtaac tgtaaaaaca     360

gaagttattg gggtaacttg tatgctaaat ttgcactctg gaacacaaaa aacacatgaa     420

aatggtgctg gaaaacccat acaggggtca aactttcatt tctttgctat tggtggggag     480

ccactggagc tgcaaggggt gctagctaac tataggacca aataccctgc tttaactgtt     540

actcctaaaa atgccacaag tgacagtcag caaatgaaca ctgatcataa agcagtgttg     600

gataaggata atgcttatcc aattgagtgc tgggttcctg atcctagtaa aaatgaaaat     660
```

```
actagatact ttggaaccta cactggtggg gaaaatgtac cccctgtgct gcacattact    720

aatactgcaa ccacagtgct tcttgatgag caaggcgtgg ggcccttatg caaagctgac    780

agcttgtatg tatctgctgc agacatttgt gggcttttta ccaacacatc tggaacccag    840

cagtggaagg gacttcccag atactttaaa attaccctga gaaagcggtc tgtgaaaaac    900

ccctacccaa tttccttttt gttaagtgac cttattaaca gaaggaccca aagggtggat    960

gggcaaccca tgattggcat gtcctctcag gttgaagagg ttagagttta tgaggacaca   1020

gaagagcttc caggggatcc agatatgata agatacattg atgagtttgg acaaaccaca   1080

acacgaatgc agtga                                                    1095


<210> SEQ ID NO 45
<211> LENGTH: 364
<212> TYPE: PRT
<213> ORGANISM: Polyomavirus SV40

<400> SEQUENCE: 45

Met Lys Met Ala Pro Ala Lys Arg Lys Gly Ser Cys Pro Gly Ala Ala
1               5                   10                  15

Pro Lys Lys Pro Lys Glu Pro Val Gln Val Pro Lys Leu Val Ile Glu
            20                  25                  30

Gly Gly Ile Glu Val Leu Gly Val Lys Thr Gly Val Asp Ser Phe Thr
        35                  40                  45

Glu Val Glu Cys Phe Leu Asn Pro Gln Met Gly Asn Pro Asp Glu His
    50                  55                  60

Gln Lys Gly Leu Ser Lys Ser Leu Ala Ala Glu Lys Gln Phe Thr Asp
65                  70                  75                  80

Asp Ser Pro Glu Lys Asp Gln Leu Pro Cys Tyr Ser Val Ala Arg Ile
                85                  90                  95

Pro Leu Pro Asn Leu Asn Glu Asp Leu Thr Cys Gly Asn Ile Leu Met
            100                 105                 110

Trp Glu Ala Val Thr Val Lys Thr Glu Val Ile Gly Val Thr Cys Met
        115                 120                 125

Leu Asn Leu His Ser Gly Thr Gln Lys Thr His Glu Asn Gly Ala Gly
    130                 135                 140

Lys Pro Ile Gln Gly Ser Asn Phe His Phe Phe Ala Ile Gly Gly Glu
145                 150                 155                 160

Pro Leu Glu Leu Gln Gly Val Leu Ala Asn Tyr Arg Thr Lys Tyr Pro
                165                 170                 175

Ala Leu Thr Val Thr Pro Lys Asn Ala Thr Ser Asp Ser Gln Gln Met
            180                 185                 190

Asn Thr Asp His Lys Ala Val Leu Asp Lys Asp Asn Ala Tyr Pro Ile
        195                 200                 205

Glu Cys Trp Val Pro Asp Pro Ser Lys Asn Glu Asn Thr Arg Tyr Phe
    210                 215                 220

Gly Thr Tyr Thr Gly Gly Glu Asn Val Pro Pro Val Leu His Ile Thr
225                 230                 235                 240

Asn Thr Ala Thr Thr Val Leu Leu Asp Glu Gln Gly Ala Gly Pro Leu
                245                 250                 255

Cys Lys Ala Asp Ser Leu Tyr Val Ser Ala Ala Asp Ile Cys Gly Leu
            260                 265                 270

Phe Thr Asn Thr Ser Gly Thr Gln Gln Trp Lys Gly Leu Pro Arg Tyr
        275                 280                 285
```

-continued

Phe Lys Ile Thr Leu Arg Lys Arg Ser Val Lys Asn Pro Tyr Pro Ile
    290                 295                 300

Ser Phe Leu Leu Ser Asp Leu Ile Asn Arg Arg Thr Gln Arg Val Asp
305                 310                 315                 320

Gly Gln Pro Met Ile Gly Met Ser Ser Gln Val Glu Glu Val Arg Val
                325                 330                 335

Tyr Glu Asp Thr Glu Glu Leu Pro Gly Asp Pro Asp Met Ile Arg Tyr
            340                 345                 350

Ile Asp Glu Phe Gly Gln Thr Thr Thr Arg Met Gln
        355                 360

<210> SEQ ID NO 46
<211> LENGTH: 1095
<212> TYPE: DNA
<213> ORGANISM: Polyomavirus SV40

<400> SEQUENCE: 46
atgaagatgg ccccagcaaa aagaaaagga agctgtccag gggcagctcc caaaaaacca 60
aaggaaccag ttcaagtacc aaagctcgtc atagaaggag gaatagaagt tctaggagtt 120
aaaactggag tagacagctt tactgaggtg gagtgctttt taaatcctca aatgggcaat 180
cctgatgaac accaaaaagg cttaagtaaa agcctagctg ctgaaaagca gtttactgat 240
gactctccag aaaaggacca gctgccctgc tacagtgtgg ccagaattcc attgcctaat 300
ttaaatgagg accttacctg tggaaatatt ttaatgtggg aagctgtaac tgtaaaaaca 360
gaagttattg gggtaacttg tatgttaaat ttgcactctg gaacacaaaa aacacatgaa 420
aatggtgctg gaaaacccat acaggggtca aactttcatt tctttgctat tggtggggag 480
ccactggagc tgcaaggggt gctagctaac tataggacca aataccctgc tttaactgtt 540
actcctaaaa atgccacaag tgacagtcag caaatgaaca ctgatcataa agcagtgttg 600
gataaggata atgcttatcc aattgagtgc tgggttcctg atcctagtaa aaatgaaaat 660
actagatact ttggaaccta cactggtggg gaaaatgtac cccctgtgct gcacattact 720
aatactgcaa ccacagtgct tcttgatgag caaggcgcgg ggcccttatg caaagctgac 780
agcttgtatg tatctgctgc agacatttgt gggcttttta ccaacacatc tggaacccag 840
cagtggaagg gacttcccag atactttaaa attaccctga gaaagcggtc tgtgaaaaac 900
ccctacccaa tttccttttt gttaagtgac cttattaaca gaaggaccca aagggtggat 960
gggcaaccca tgattggcat gtcctctcag gttgaagagg ttagagttta tgaggacaca 1020
gaagagcttc caggggatcc agatatgata agatacattg atgagtttgg acaaaccaca 1080
acacgaatgc agtga 1095

<210> SEQ ID NO 47
<211> LENGTH: 8
<212> TYPE: PRT
<213> ORGANISM: Artificial Sequence
<220> FEATURE:
<223> OTHER INFORMATION: Synthetic sequence, FLAG sequence

<400> SEQUENCE: 47

Asp Tyr Lys Asp Asp Asp Asp Lys
1               5

<210> SEQ ID NO 48
<211> LENGTH: 9
<212> TYPE: PRT
<213> ORGANISM: Artificial Sequence -continued

```
<220> FEATURE:
<223> OTHER INFORMATION: Synthetic RGD sequence

<400> SEQUENCE: 48

Arg Gly Asp Arg Gly Asp Arg Gly Asp
1               5
```

IMMUNOSTIMULATOR AND METHOD FOR PRODUCING THE SAME

CROSS REFERENCE TO RELATED APPLICATIONS

This application claims priority from prior Japanese Patent Application No. 2015-255012, filed on Dec. 25, 2015, entitled "IMMUNOSTIMULATOR AND METHOD FOR PRODUCING THE SAME", the entire contents of which are incorporated herein by reference.

TECHNICAL FIELD

The present invention relates to an immunostimulator containing virus-like particles, a method for producing the same and a method for potentiating immune effect of a living body by administering the immunostimulator.

BACKGROUND

For protection against infection by pathogens (infection prevention) and treatment of diseases such as infections and cancer, a vaccine is sometimes administered to a living body. A vaccine is usually administered with an immunostimulator. The immunostimulator is also called as an adjuvant. The immunostimulator has an ability to enhance the effect of vaccine such as enhancement of immune response to a vaccine antigen. For example, US Patent Application Publication No. 2015-174223 describes that an adjuvant can be contained in a pharmaceutical composition containing a peptide vaccine. As specific examples of adjuvant, aluminum phosphate, aluminum hydroxide and the like are described.

SUMMARY OF THE INVENTION

The scope of the present invention is defined solely by the appended claims, and is not affected to any degree by the statements within this summary.

The present inventors have unexpectedly found that virus-like particles having an outer coat of SV40 have a property as an adjuvant, thereby completing the present invention.

More specifically, an immunostimulator comprising virus-like particles is provided. The virus-like particles contain an outer coat protein comprising an amino acid sequence selected from the group consisting of SEQ ID No. 1, SEQ ID No. 26, SEQ ID No. 33, SEQ ID No. 35, SEQ ID No. 37, SEQ ID No. 39, SEQ ID No. 41, SEQ ID No. 43 and SEQ ID No. 45. The outer coat protein constitutes an outer coat of the virus-like particles. The virus-like particles do not substantially contain a genome DNA of SV40.

DETAILED DESCRIPTION OF THE PREFERRED EMBODIMENTS

Figure 1:
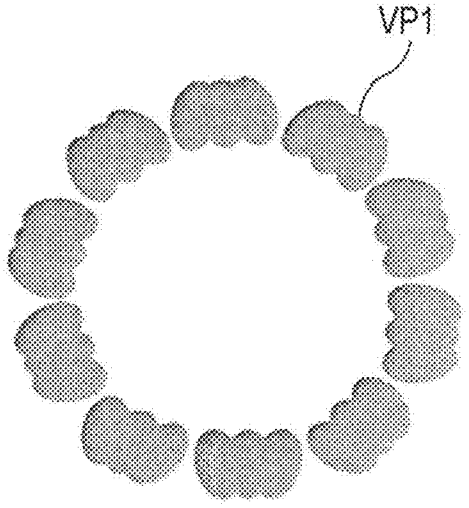
FIG. 1 is a schematic view showing an example of a virus-like particle.

An immunostimulator of a present embodiment contains virus-like particles having an outer coat constituted from an outer coat protein derived from SV40 (Simian Virus 40). The phrase "an outer coat is constituted from an outer coat protein" means that the outer coat substantially comprises the outer coat protein. More specifically, the outer coat may be constituted only by an outer coat protein. Alternatively, the outer coat protein may be constituted by an outer coat protein and a protein bindable to the outer coat protein in a range in which the structure of outer coat is maintained. More specifically, the outer coat of wild-type SV40 virus is constituted by assembling of 72 VP1 pentamer units, and VP2 and VP3 are bound to the inside of the constituted outer coat as lining. However, VP1 of SV40 can constitute an outer coat by itself even without VP2 and VP3. In the present embodiment, the outer coat protein means a protein capable of substantially constituting an outer coat by themselves like SV40 VP1.

The outer coat of the virus-like particles preferably does not substantially contain VP2, VP3, or both of them. The phrase "The outer coat of the virus-like particles does not substantially contain VP2, VP3, or both of them" does not eliminate the possibility that VP2 or VP3 is contained in the outer coat of the virus-like particles, but is used as an expression which remains the possibility that VP2 and VP3 are present as a member non-essential for outer coat formation, in a form that the original functions of VP2 and VP3 in a wild-type SV40 cannot be exhibited. The outer coat of the virus-like particles more preferably does not contain both VP2 and VP3.

SV40 is a type of virus belonging to the genus *Polyomavirus* (Genus: *Polyomavirus*), in the virus classification published by International Committee on Taxonomy of Viruses (ICTV) in 2014. In the virus classification, reorganization of the classification and modification of generic name, species name or the like are often made. Accordingly, while the classification can be reorganized, or the generic name, species name or the like can be modified in the classification by ICTV or an equivalent academic authority in the future, viruses corresponding to SV40 in the ICTV classification in 2014 are defined to be naturally included in SV40 referred in this specification.

The outer coat protein is not required to have completely same amino acid sequence as that of a wild-type virus. The amino acid sequence may be varied as long as it does not hinder outer coat formation. Variation of amino acid sequence means that one or more amino acid residues are substituted, deleted or added as compared to the wild-type sequence. The variant amino acid sequence has preferably at least 85%, more preferably at least 90% and further preferably at least 95% sequence identity with the amino acid sequence of the wild-type SV40VP1 (SEQ ID No. 1). The outer coat protein may form an outer coat by its self-assembling ability, or may form an outer coat by the action of factors inherent in a host. The outer coat protein may form an outer coat, as monomers, or may form outer coat-forming units (capsomere) constituted from multimers and form an outer coat by assembling of the units. The outer coat protein forms an outer coat by assembling of preferably dimers to decamers and more preferably trimers to pentamers of about 50 to 500 capsomeres. The outer coat protein may be an extracted and purified natural protein, or may be artificially synthesized by a genetic engineering technique or the like.

The outer coat protein contains an amino acid sequence selected from the group consisting of SEQ ID No. 1, SEQ ID No. 26, SEQ ID No. 33, SEQ ID No. 35, SEQ ID No. 37, SEQ ID No. 39, SEQ ID No. 41, SEQ ID No. 43 and SEQ ID No. 45. SEQ ID No. 1 is an amino acid sequence of VP1 of the wild-type SV40 VP1 (wt SV40 VP1). SEQ ID No. 1 is encoded by a nucleic acid sequence of SEQ ID No. 2 or SEQ ID No. 25. SEQ ID No. 26 is one of the amino acid sequences of a variant-type SV40 VP1. SEQ ID No. 26 is encoded by a nucleic acid sequence of SEQ ID No. 27, SEQ ID No. 28, SEQ ID No. 29, SEQ ID No. 30, SEQ ID No. 31, or SEQ ID No. 32. SEQ ID No. 33, SEQ ID No. 35, SEQ ID No. 37, SEQ ID No. 39, SEQ ID No. 41, SEQ ID No. 43 and SEQ ID No. 45 are each one of the amino acid sequences of a variant-type SV40 VP1, and are each encoded by a nucleic acid sequence of SEQ ID No. 34, SEQ ID No. 36, SEQ ID No. 38, SEQ ID No. 40, SEQ ID No. 42, SEQ ID No. 44 or SEQ ID No. 46.

The virus-like particles do not substantially contain a genome DNA of SV40. The phrase "do not substantially contain a genome DNA of SV40" means that DNA functioning for self-replication of SV40 is not contained. The virus-like particles do not substantially contain a genome DNA of SV40. Thus, the virus-like particles cannot parasitize a host cell to carry out self-replication like natural virus. The virus-like particles may contain at least part of the genome DNA of SV40, as long as the genome DNA does not function for self-replication.

The shape of outer coat is not particularly limited. The shape may be spherical or tubular. The shape of outer coat is, for example, approximately spherical, regular octahedron to regular icosahedron. VP1 of the wild-type SV40 forms an outer coat of approximately spherical regular icosahedron. Particularly when there is a variation in the amino acid sequence of the outer coat protein, VP1 may have a different shape from the outer coat of the wild-type.

When the outer coat is constituted from monomers of outer coat protein, the number of monomers constituting one outer coat is not particularly limited, but is preferably 100 to 1000 and more preferably 150 to 500. When the outer coat is constituted from capsomeres, the number of capsomeres constituting one outer coat is preferably 50 to 390 and more preferably 72 to 260. VP1 of the wild-type SV40 forms an outer coat by assembly of 72 capsomeres constituted from pentameric VP1 (the number of monomers of 360). Particularly when there is a variation in the amino acid sequence of the outer coat protein, VP1 may constitute an outer coat in a different form from the wild-type.

The diameter of outer coat is not particularly limited. The diameter of outer coat is preferably 30 to 300 nm and more preferably 45 to 200 nm. The diameter of the outer coat of the wild-type SV40 is about 45 nm. Particularly when there is a variation in the amino acid sequence of the outer coat protein, SV40 may have a different diameter from the wild-type.

The outer coat may be constituted from any one kind of the wild-type VP1 and variant-type VP1 described above. Alternatively, the outer coat may contain plural kinds.

The virus-like particles can be used as an adjuvant for administering with an antigen for vaccine, in a vaccine for preventing or treating viral diseases or prevention or treatment of various cancers. Specifically, virus-like particles can be used as an adjuvant for administering with an antigen for vaccine, in the prevention or treatment of diseases such as infections (influenza, immunodeficiency syndrome, hepatitis C, etc.), cancers (cervical cancer, pharyngeal papilloma, etc.), verrucas (verruca vulgaris, inclusion body of verruca vulgaris, verruca plana, etc.), HPV-associated epidermoid cyst, epidermodysplasia verruciformis, condyloma acuminatum and bowenoid papulosis.

When virus-like particles are administered to a living body with an antigen, the virus-like particles can potentiate an immune effect of a living body on the antigen. Namely, virus-like particles of the present embodiment can be used as an adjuvant for administering with an antigen for vaccine, in prevention and/or treatment of diseases such as viral infections, bacterial infections, and cancers. The action mechanism of adjuvant is diverse and is not often elucidated. As one commonly accepted view, it is known that the adjuvant itself has antigenicity and consequently enhances the induction ability of immune cells, thus potentiates an immune effect on the antigen administered together. It has been so far considered that SV40 has low or no immunogenicity since SV40 does not induce increase in expression of CD86 (Cluster of Differentiation) molecule that is an immune activation marker, in a dendritic cell that is representative of antigen-presenting cells. It has been considered that there is no adjuvant effect to a dendritic cell as well, also for general *polyomavirus*. However, the present inventors have unexpectedly found that, when the virus-like particles of the present embodiment themselves have an antigenicity and administered with an antigen, the virus-like particles potentiate an immune effect on the antigen. It is possible that the virus-like particles of the present embodiment also potentiate an immune effect on the antigen administered together, attributed to the antigenicity of itself. The present inventors have unexpectedly found knowledge that the virus-like particles of the present embodiment potentiate an immune effect of a living body on the antigen administered together, on the contrary to the technical common knowledge so far.

The above antigen may be added to the outer coat protein of the virus-like particles. In the outer coat protein, a site to which the antigen is added is not particularly limited, and the antigen may be added to any amino acid. The antigen may be added in a form of being exposed outside of the outer coat. The antigen may be added in a form of being included in the outer coat.

The kind of antigen is not particularly limited, and examples thereof include polypeptides, sugar chains, nucleic acids, lipids, and the like. The outer coat protein is not included in "antigen" in this specification. The antigen is preferably polypeptide, and more preferably a polypeptide derived from a pathogen. Examples of the polypeptide antigen derived from a pathogen include HA, NA, M1, M2, NP, NS1, NS2, PA, PB1, PB2, PB1-F2 and the like of influenza viruses, Gag, Pol, Env, Tat, Nef, Rev and the like of HIV, E1, E2, Core, NS2, NS3, NS4, NS5 and the like of hepatitis C viruses (HCV), E6, E7 and the like of viruses belonging to the Papillomavirus family, Melan-A/MART-1, gp100, MAGEA3, MAGE-A10, CEA, HER2/new, NY-E50-1, WT-1, hTERT and the like that are proteins specific to cancer cells, and the like. Among them, M1, NP, NS1, PA, PB1 and PB2 of influenza viruses, HER2/new, WT-1 and MAGE-A3 that are proteins specific to cancer cells and the like are preferred. The size of the polypeptide antigen is not particularly limited. The polypeptide antigen may be a full-length protein. The polypeptide antigen may be a part of protein at least containing epitope.

The method of adding an antigen to an outer coat peptide is not particularly limited, and a method known to a person skilled in the art, for example, a chemical procedure, a method using a gene recombination technique and the like can be used. Examples of the chemical procedure include crosslinking by one or more crosslinkers known to a person skilled in the art and the like. Examples of the method using a gene recombination technique include fusing of a gene encoding an antigen and/or antigen epitope (T-helper epitope, CTL epitope, antibody epitope, ADCC (Antibody-dependent cell-mediated cytotoxicity) epitope, etc., epitope inducing immune response) to a gene encoding VP1 of SV40 virus like US Patent Application Publication No. 2014-0286978, and the like. In the present embodiment, an antigen and/or antigen epitope can be specifically added by crosslinking via EDC crosslinker (for example, Thermo Fisher Scientific Inc., etc.).

Figure 2:
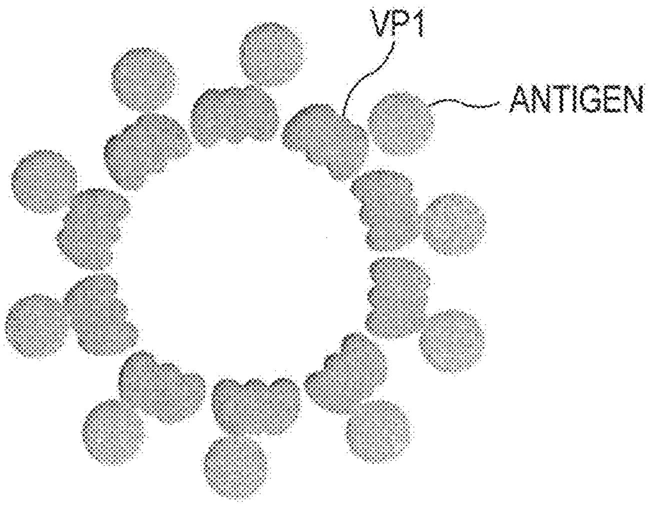
FIG. 2 is a schematic view showing an example of a virus-like particle.

The schematic view of an example of a virus-like particle is shown in FIG. 1. The virus-like particle represented by this schematic view comprises an outer coat constituted by a wild-type SV40 outer coat protein VP1 having an amino acid sequence of SEQ ID No. 1. The virus-like particle exemplified in FIG. 1 does not contain genome DNA of SV40, and comprises approximately spherical regular icosahedron constituted by assembly of 72 capsomeres constituted from pentameric VP1 (the number of monomers of 360). The diameter of the virus-like particle shown in FIG. 1 is about 45 nm. The schematic view of another example of a virus-like particle is shown in FIG. 2. This virus-like particle has the same outer coat as the virus-like particle shown exemplified FIG. 1, and an antigen is added to the surface of the outer coat.

The virus-like particles potentiate an immune effect of a living body. The phrase "potentiate an immune effect" refers to enhance an immune response to an antigen. Enhancement of immune response refers to, for example, enhancement of the production of cytotoxic T lymphocytes (CTL) induced by administration of an antigen specific to the antigen (enhancement of cellular immunity), enhancement of the production of antibody induced by administration of an antigen specific to the antigen (enhancement of humoral immunity), and the like.

In one embodiment, virus-like particles can potentiate an immune effect, with CD86 expression induction in lymphocytes, particularly, $CD4^+$T cells, $CD8^+$T cells and B cells. For example, CD86 is a protein present in the surface of an antigen-presenting cell (B cell, macrophage, dendritic cell). CD86 is involved in the activation of T cells. CD86 is also an antigen that activates B cells. Accordingly, it is considered that the virus-like particles of the present embodiment activate T cells and B cells with CD86 expression induction, and potentiate an immune effect of a living body.

In the preferred embodiment, virus-like particles can potentiate an immune effect, with CD86 expression in lymphocytes of mouse, dependently on GM1, a type of gangliosides. Gangliosides are present in a lipid bilayer. Gangliosides are involved in adjustment of cellular signal transduction. Accordingly, it is considered that the virus-like particles of the present embodiment activate T cells and B cells, and potentiate an immune effect of a living body, while GM1 is involved in some form in the process of cellular signal transduction to induce CD86 expression.

In another embodiment, virus-like particles induce expression of various CD molecules, specifically, CD69, CD81, CD83, CD196, CD197, CD63, and CD68, in lymphocytes. Thus, the virus-like particles of the present embodiment potentiate an immune effect of a living body.

In another embodiment, virus-like particles do not much induce secretion of inflammatory cytokines involved in the formation of pathological conditions of systemic inflammation, for example, interferon γ (IFN-γ), tumor necrosis factor α (TNF-α), interleukin 6 (IL-6) and interleukin 1β (IL-1β), in lymphocytes. On the other hand, virus-like particles induce secretion of chemokines involved in the formation of pathological conditions of local inflammation, for example, CCL3 and CCL4. When a vaccine is administered, the applied part is inflamed, macrophages aggregate, and the antigen is likely to be phagocytosed. Accordingly, antigen presentation effectively occurs. However, it becomes unwanted side effects for a living body when inflammation spreads throughout the whole body. It is considered that the virus-like particles of the present embodiment reduce induction of inflammatory cytokines involved in systemic inflammation and induce chemokines involved in local inflammation, thus effectively potentiate an immune effect of a living body, and side effects are reduced.

In another embodiment, virus-like particles increase phosphorylation of various kinases, specifically, Erk1/2, JNK and p38MAPK, in lymphocytes. Thus, it is considered that the virus-like particles of the present embodiment potentiate an immune effect of a living body.

An immunostimulator may contain any one kind or plural kinds of virus-like particles constituted by VP1 of SEQ ID No. 1, virus-like particles constituted by VP1 of SEQ ID No. 26, virus-like particles constituted by VP1 of SEQ ID No. 33, virus-like particles constituted by VP1 of SEQ ID No. 35, virus-like particles constituted by VP1 of SEQ ID No. 37, virus-like particles constituted by VP1 of SEQ ID No. 39, virus-like particles constituted by VP1 of SEQ ID No. 41, virus-like particles constituted by VP1 of SEQ ID No. 43, and virus-like particles constituted by VP1 of SEQ ID No. 45, as long as it is pharmacologically effective.

In the immunostimulator, virus-like particles may be formulated with an antigen and/or a pharmaceutical additive known to a person skilled in the art. The pharmaceutical additive as described above is not particularly limited, and examples thereof include excipients, lubricants, binders, disintegrants, coating agents, capsule base materials, plasticizers, colorants, solvents, stabilizers, preservatives, buffers, analgesics, bases, emulsifiers and suspending agents, other corrigents, sweeteners, absorbents, dissolution adjuvants, pH adjusting agents, thickeners, tonicity agents, dispersants, antiseptics, wetting agents, flavoring agents, antioxidants, and the like.

The excipient is not particularly limited, and examples thereof include mannitol, sucrose, glucose, corn starch, crystalline cellulose, calcium hydrogen phosphate, and the like.

The lubricant is not particularly limited, and examples thereof include magnesium stearate, talc, colloidal silica, and the like.

The binder is not particularly limited, and examples thereof include gum arabic, hydroxypropylcellulose (HPC), hydroxypropylmethylcellulose (HPMC), methylcellulose (MC), povidone (PVP), polyvinyl alcohol (PVA), and the like.

The disintegrant is not particularly limited, and examples thereof include cross-linked carmellose sodium, carmellose calcium, cross-linked povidone, sodium carboxymethyl starch, and the like.

The coating agent is not particularly limited, and examples thereof include coating agents for sugar coating such as sucrose and talc, enteric coating agents such as carboxymethylethyl cellulose, gastrosoluble coating agents such as polyvinyl acetal diethyl aminoacetate, and the like.

The capsule base material is not particularly limited, and examples thereof include gelatin and the like.

The plasticizer is not particularly limited, and examples thereof include triacetin, medium-chain triglyceride, and the like.

The colorant is not particularly limited, and examples thereof include edible tar colors, lake pigments, iron sesquioxide, and the like.

The solvent is not particularly limited, and examples thereof include aqueous solvents such as water for injection and sterile purified water, nonaqueous solvents such as vegetable oils (including olive oil, soybean oil, sesame oil and the like), and the like.

The stabilizer is not particularly limited, and examples thereof include inert gas such as nitrogen and carbon dioxide, chelating agents such as EDTA, reduction substrates such as L-ascorbic acid, and the like.

The preservative is not particularly limited, and examples thereof include p-oxybenzoic ester, chlorobutanol, and the like.

The buffer is not particularly limited, and examples thereof include sodium salts of citric acid, acetic acid, phosphoric acid, and the like.

The analgesic is not particularly limited, and examples thereof include benzyl alcohol, procaine hydrochloride, glucose, and the like.

The base is not particularly limited, and examples thereof include bases for suppositories such as cacao butter and gelatin, bases for ointments such as liquid paraffin and carnauba wax, and the like.

The emulsifier is not particularly limited, and examples thereof include gum arabic, polysorbate, sodium lauryl sulfate, and the like.

The suspending agent is not particularly limited, and examples thereof include gum arabic, sodium alginate, tragacanth, aluminum monostearate, and the like.

An immunostimulator may be any of a solid preparation, a semisolid preparation, a liquid preparation, an injection, a suppository, and other preparation form known to a person skilled in the art. Specific dosage form is not particularly limited, and examples thereof include tablets, pills, granules, powders, capsules, troches, injections, liquid agents, elixirs, syrups, limonades, suppositories, ointments, suspension agents, emulsions, liniments, lotions, percutaneous absorption preparations, patches, cataplasms, aerosols, and the like.

The liquid preparation is prepared, for example, by extracting virus-like particles from a host cell expressing the virus-like particles, and adding an antigen and diluting the virus-like particles with an appropriate solvent as necessary.

The suspension agent is prepared, for example, by producing a homogenate obtained by homogenizing a host cell expressing the virus-like particles, and adding an antigen, and extracting, purifying, and diluting the homogenate with a solvent as necessary. Specifically, when a lepidopterous insect individual such as a silkworm is used as a host, a suspension agent can be prepared by grinding an individual expressing the virus-like particles, and roughly purifying the ground individual.

When the virus-like particles are not formulated with an antigen, an immunostimulator containing the virus-like particles may be administered simultaneously with an antigen, or may be separately administered. The virus-like particles are preferably administered simultaneously with an antigen. For example, an immunostimulator is mixed with an antigen or a composition containing an antigen, and administered to a living body. Regarding virus-like particles, the phrase "administered with an antigen" does not necessarily mean that virus-like particles must be administered at the same time points, but is used as an expression including that both antigen and virus-like particles are administered at separate time points in one dosage schedule.

The administration route of an immunostimulator is not particularly limited, and examples thereof include transmucosal administration (for example, oral administration, transnasal administration, intranasal administration, buccal administration, enema administration, and the like), parenteral administration (for example, intraperitoneal injection, subcutaneous injection, intravenous injection, intramuscular injection, injection into a space between tissues, and the like), transdermal administration, and the like. More specifically, the immunostimulator of the present embodiment can be used by not only a high burden administration by injection or the like, but also a low burden administration by oral ingestion, administration by collunarium, enema or the like. For example, an immunostimulator can be used as an adjuvant for a vaccine for animals by mixing into animal feed with an antigen.

The dose and number of doses of an immunostimulator can be properly set by a person skilled in the art according to the kind of an antigen, animal species of an administration target, and symptom, age, body weight, administration form and the like, of an administration target. The dose is usually 0.01 μg to 100 mg, preferably 0.1 μg to 50 mg, and more preferably 1.0 μg to 10 mg, and it is preferred to administer an immunostimulator once per few days to few months.

The administration target of an immunostimulator can be biological bodies, more specifically, human or animals other than human (mammals other than human, birds, reptiles, and the like). Examples of animals other than human include bovine, equine, porcine, chicken, canine, feline, mouse, rat, lagomorph, simian, and the like.

The immunostimulator of the present embodiment contains a pharmacologically effective amount of virus-like particles from the viewpoint of immune effect enhancement. The virus like particles may cause a pharmaceutically acceptable side effect when administered, but it is preferred for the animal of an administration target that there is no pathogenicity, and a side effect is not caused.

The immunostimulator of the present embodiment can be produced by preparing virus-like particles according to a method known to a person skilled in the art, and formulating the virus-like particles by mixing with an antigen and/or a pharmaceutically acceptable excipient or the like as necessary.

The virus-like particles can be prepared using an outer coat protein containing an amino acid sequence selected from the group consisting of SEQ ID No. 1, SEQ ID No. 26, SEQ ID No. 33, SEQ ID No. 35, SEQ ID No. 37, SEQ ID No. 39, SEQ ID No. 41, SEQ ID No. 43 and SEQ ID No. 45. For example, it can be performed by dispersing an outer coat protein in a proper medium. The medium and dispersion conditions can be properly set by a person skilled in the art.

Before preparing virus-like particles, the outer coat protein may be obtained by incorporating a DNA encoding the outer coat protein incorporated into a host cell to express the outer coat protein in the host cell. These proteins can be obtained by a method known to a person skilled in the art, for example, gene recombination and the like.

The host cell is not particularly limited as long as it does not hinder the formation of virus-like particles. The host cell is selected, for example, from a group consisting of insect cells (including insect individuals such as silkworm), *Escherichia coli*, yeasts and plants. The host cell is preferably an insect cell, more preferably a lepidopterous insect individual, and further preferably a silkworm.

When an outer coat protein is expressed in a host cell, virus-like particles may be prepared by contact of the outer coat proteins expressed in the host cell each other. Alternatively, virus-like particles may be formed in a production process such as homogenization, purification and extraction on the host cell.

The virus-like particles formed in the host cell may be collected as necessary. Collection method is not particularly limited, but a person skilled in the art can properly selected mainly depending on the kind of the host cell. For example, when the host cell is an insect cell, an *Escherichia coli* cell or the like, cytolysis and the like by ultrasonication or the like can be used. When the host cell is a pupa of a lepidopterous insect, a method of eluting virus-like particles by grinding or the like, and collecting a supernatant after centrifugation can be used.

In a preferred embodiment, first, an insect cell or insect individual is infected with a baculovirus into which a DNA encoding an outer coat protein is incorporated. Next, the insect cell or insect individual is subjected to ultrasonic treatment or ground, then centrifuged or filtered, and the supernatant is collected, whereby virus-like particles can be obtained.

The virus-like particles may be purified as necessary. The purification method is not particularly limited, and examples thereof include methods known to a person skilled in the art such as density gradient centrifugation and chromatography and the like.

An antigen may be added to the virus-like particles. A method of adding an antigen to an outer coat peptide is as described above.

Formulation can be performed, for example, by mixing virus-like particles to which an antigen is added with an appropriate pharmaceutical composition, or mixing virus-like particles with an antigen and/or an appropriate pharmaceutical additive, molding into a desired dosage form, and coating the dosage form as necessary.

Specifically, when a dosage form is formed into a solid preparation, for example, a tablet, it can be formulated, for example, by mixing virus-like particles to which an antigen is added with an appropriate excipient, binder and/or disintegrant, or mixing virus-like particles with an antigen and/or an appropriate excipient, binder and/or disintegrant, adding an appropriate lubricant, further mixing the ingredients, tableting the mixture, and coating the dosage form as necessary.

When a dosage form is formed into an injection or a liquid preparation, it can be formulated, for example, by dispersing virus-like particles to which an antigen is added or virus-like particles in an appropriate solvent, adding an antigen and/or filtering or sterilizing the dispersion as necessary, and filling the dispersion in a predetermined container.

When a dosage form is formed into an ointment, it can be formulated, for example, by melting an appropriate ointment in a mixer equipped with a warming device, stopping warming, mixing at a low speed until it coagulates in the form of an ointment, adding virus-like particles to which an antigen is added or virus-like particles and an antigen as necessary, immediately before coagulation, and filling the mixture in a predetermined container.

When a dosage form is formed into a suppository, it can be formulated, for example, by mixing virus-like particles to which an antigen is added with an appropriate base for suppositories previously melted at a low temperature, or mixing virus-like particles with an appropriate base for suppositories previously melted at a low temperature, and an antigen as necessary, pouring the mixture into a mold, and cooling it to harden.

Another embodiment relates to virus-like particles for potentiating an immune effect of a living body. More specifically, another embodiment relates to virus-like particles for potentiating an immune effect of a living body, in which the virus-like particles contain an outer coat protein containing an amino acid sequence selected from the group consisting of SEQ ID No. 1, SEQ ID No. 26, SEQ ID No. 33, SEQ ID No. 35, SEQ ID No. 37, SEQ ID No. 39, SEQ ID No. 41, SEQ ID No. 43 and SEQ ID No. 45, the outer coat protein constitutes an outer coat of the virus-like particles, and the virus-like particles do not substantially contain a genome DNA of SV40.

The virus-like particles, outer coat protein, outer coat and the like are as described above.

The virus-like particles of the present embodiment can be used as an immunostimulator that potentiates an immune effect of a living body on an antigen by administering the virus-like particles with the antigen, in the prevention or treatment of disease. More specifically, the virus-like particles can be used as an immunostimulator that potentiates an immune effect of a living body on an antigen by administering the virus-like particles with the antigen, in the prevention or treatment of diseases such as infections (influenza, HIV, hepatitis C, etc.), cancers (cervical cancer, pharyngeal papilloma, etc.), verrucas (verruca vulgaris, inclusion body of verruca vulgaris, verruca plana, etc.), HPV-associated epidermoid cyst, epidermodysplasia verruciformis, condyloma acuminatum and bowenoid papulosis.

Accordingly, it can be also said that another embodiment relates to virus-like particles for treating a disease by administering the virus-like particles with the antigen. More specifically, the present embodiment relates to virus-like particles for treating a disease by administering the virus-like particles with an antigen, in which the virus-like particles contain an outer coat protein containing an amino acid sequence selected from the group consisting of SEQ ID No. 1, SEQ ID No. 26, SEQ ID No. 33, SEQ ID No. 35, SEQ ID No. 37, SEQ ID No. 39, SEQ ID No. 41, SEQ ID No. 43 and SEQ ID No. 45, the outer coat protein constitutes an outer coat of the virus-like particles, and the virus-like particles do not substantially contain a genome DNA of SV40.

The virus-like particles, outer coat protein, outer coat, antigen, diseases and the like are as described above.

Another embodiment relates to a method for potentiating an immune effect of a living body including administering virus-like particles to the living body. The virus-like particles contain an outer coat protein containing an amino acid sequence selected from the group consisting of SEQ ID No. 1, SEQ ID No. 26, SEQ ID No. 33, SEQ ID No. 35, SEQ ID No. 37, SEQ ID No. 39, SEQ ID No. 41, SEQ ID No. 43 and SEQ ID No. 45, the outer coat protein constitutes an outer coat of the virus-like particles, and the virus-like particles do not substantially contain a genome DNA of SV40.

The virus-like particles, outer coat protein, outer coat and administration method thereof, a biological body and the like are as described above.

It can be also said that another embodiment relates to a method for preventing or treating diseases including administering virus-like particles to a living body. More specifically, the present embodiment relates to a method for preventing or treating diseases, including administering virus-like particles to a living body with an antigen, in which the virus-like particles contain an outer coat protein containing an amino acid sequence selected from the group consisting of SEQ ID No. 1, SEQ ID No. 26, SEQ ID No. 33, SEQ ID No. 35, SEQ ID No. 37, SEQ ID No. 39, SEQ ID No. 41, SEQ ID No. 43 and SEQ ID No. 45, the outer coat protein constitutes an outer coat of the virus-like particles, and the virus-like particles do not substantially contain a genome DNA of SV40.

The virus-like particles, outer coat protein, outer coat, antigen and administration method thereof, a biological body, diseases and the like are as described above.

Another embodiment relates to use of virus-like particles in the production of an immunostimulator.

The virus-like particles, outer coat protein, outer coat, immunostimulator and administration method thereof, a biological body, diseases and the like are as described above.

Hereinbelow, the present invention will be described in detail by way of examples, but the present invention is not limited to these examples.

EXAMPLES

Example 1: Activation of CTL Peptide Using wt SV40 VP1 VLP

Preparation of Baculovirus Expressing Wild-Type (wt) Simian Virus 40 (SV40) VP1

*Escherichia coli* DH10bac (invitrogen) holding a baculovirus genome was transformed with a plasmid obtained by inserting wt SV40 VP1 gene (SEQ ID No. 2; the amino acid sequence is shown in SEQ ID No. 1) into Sal I site and Kpn I site of pFastBac1 plasmid (invitrogen) to prepare a recombinant baculovirus genome into which VP1 was incorporated. The recombinant baculovirus genome was transfected to Sf-9 cells. After three days, the supernatant thereof was collected to obtain a solution containing recombinant baculovirus. A part of this solution was again infected with Sf-9 cells (invitrogen), thereby increasing a recombinant baculovirus titer. The resulting solution was referred to as a stock solution of a recombinant baculovirus.

Preparation of wt SV40 VP1 Virus-Like Particles (VLP)

A recombinant baculovirus with wt SV40 VP1 incorporated therein was infected in a 15 cm culture dish in which $3\times10^7$ Sf-9 cells were inoculated at a multiplicity of infection of 0.05 to 0.2 (M.O.I. base). A total of 10 dishes was each prepared. Three days after infection, a total of $3\times10^8$ Sf-9 cells inoculated on these 10 dishes were collected, and washed with PBS(−). Thereafter, the cells were resuspended in 10 ml of a buffer for VP1 ultrasonic treatment (20 mM Tris-HCl (pH 7.9), 1% (w/vol) deoxycholic acid (Sigma)). In order to suppress endogenous protease activity, 2 mM phenylmethylsulfonyl fluoride (final concentration of 2 μM, Sigma), chymostatin (final concentration of 1 μg/ml, Sigma), aprotinin (final concentration of 1 μg/ml, Sigma), leupeptin (final concentration of 1 μg/ml, Sigma), antipain (final concentration of 1 μg/ml, Sigma) and pepstatin (final concentration of 1 μg/ml, Sigma) were added thereto, and the mixture was ultrasonically crushed. Thereafter, the crushed substance was centrifuged at 15,000 rpm, 4° C. for 5 minutes to separate into supernatant and pellet, and the supernatant was defined as a lysate solution.

Each 1.5 ml of a 20% CsCl solution (20 mM Tris-HCl (pH 7.9), 20% (w/vol) cesium chloride), a 30% CsCl solution (20 mM Tris-HCl (pH 7.9), 30% (w/vol) cesium chloride), a 40% CsCl solution (20 mM Tris-HCl (pH 7.9), 40% (w/vol) cesium chloride), and a 50% CsCl solution (20 mM Tris-HCl (pH 7.9), 50% (w/vol) cesium chloride) were superposed in an Ultra-Clear centrifugation tube (14×89 mm, Beckman coulter) in descending order of density, for density gradient centrifugation of cesium chloride. Subsequently, 5 ml of a lysate solution containing wt SV40 VP1 was further superposed. The centrifugation tube was ultracentrifuged at 35,000 rpm, 4° C. for 3 hours (SW41Ti rotor, Beckman).

After ultracentrifugation, a white band appeared at the center was collected with 23 G, 1 ml of a Terumo syringe (0.60×32 mm, TERUMO). This fraction was mixed with a 37% CsCl solution (20 mM Tris-HCl (pH 7.9), 37% (w/vol) cesium chloride), and the mixture was transferred to an Ultra-Clear centrifugation tube (11×60 mm, Beckman coulter). Thereafter, the centrifugation tube was ultracentrifuged at 50,000 rpm, 4° C. for 20 hours (SW60Ti rotor, Beckman). After ultracentrifugation, a white band appeared at the center was collected with 23 G, 1 ml of a Terumo syringe (0.60×32 mm, TERUMO). This fraction was dialyzed (Slide-A-Lyzer (trademark) MINI Dialysis Units, 3500 MWCO, Thermo SCIENTIFIC) against a PBS(−) solvent. This fraction was centrifuged at 15,000 rpm, 4° C. for 5 minutes. The supernatant was collected and referred to as a purified VP1 VLP fraction.

Immobilization of FMP:58-66 Peptide on SV40 Wild-Type VP1 VLP

A sample of wt SV40 VP1 VLP in which FMP:58-66 epitope peptide (GILGFVFTL, SEQ ID No. 3; herein also called as "CTL epitope of M1") was immobilized thereon was prepared, as described below.

(1) 35.04 μl of a MES buffer of the same composition was added to 39.96 μl of wt SV40 VP1 VLP (3752.7 ng/μl) dialyzed against a MES buffer (0.1 M MES (2-(N-morpholino)ethanesulfonic acid), 0.9% sodium chloride, pH 4.7, BupH MES buffered saline water pack, 28390, Thermo SCIENTIFIC) to make a total of 75 μl. 32.4 μl of a MES buffer was added to 155.1 μl of 10 mM FMP:58-66 peptide (GILGFVFTL, SEQ ID No. 3) (molecular weight of 966.9) dissolved in DMSO to make a total of 187.5 μl. Moreover, these buffers were mixed. Thereto was added 7.5 μl of EDC crosslinker (EDC, 22980, Thermo SCIENTIFIC) (10 mg/ml in redistilled water). Furthermore, 30 μl of redistilled water was added to make a total amount of 300 μl. This mixture liquid was incubated at room temperature for 2 hours to react a crosslinker. This was referred to as a 1:10 (with EDC) sample in a weight ratio of VP1:FMP:58-66 epitope peptide.

(2) 35.04 μl of a MES buffer of the same composition as described above was added to 39.96 μl of SV40 wild type VP1 VLP (3752.7 ng/μl) dialyzed against a MES buffer of the same composition to make a total of 75 μl. 109.95 μl of a MES buffer was added to 77.55 μl of 10 mM FMP:58-66 peptide (GILGFVFTL, SEQ ID No. 3) (molecular weight of 966.9) dissolved in DMSO to make a total of 187.5 μl. Moreover, these buffers were mixed. Thereto was added 7.5 μl of EDC crosslinker (EDC, 22980, Thermo SCIENTIFIC) (10 mg/ml in redistilled water). Furthermore, 30 μl of redistilled water was added to make a total amount of 300 μl. This mixture liquid was incubated at room temperature for 2 hours to react a crosslinker. This was referred to as a 1:5 (with EDC) sample in a weight ratio of VP1:FMP:58-66 epitope peptide.

(3) 35.04 μl of a MES buffer of the same composition as described above was added to 39.96 μl of SV40 wild type VP1 VLP (3752.7 ng/μl) dialyzed against a MES buffer of the same composition to make a total of 75 μl. 148.72 μl of a MES buffer was added to 38.78 μl of 10 mM FMP:58-66 peptide (GILGFVFTL, SEQ ID No. 3) (molecular weight of 966.9) dissolved in DMSO to make a total of 187.5 μl. Moreover, these buffers were mixed. Thereto was added 7.5 μl of EDC crosslinker (EDC, 22980, Thermo SCIENTIFIC) (10 mg/ml in redistilled water). Furthermore, 30 μl of redistilled water was added to make a total amount of 300 μl. This mixture liquid was incubated at room temperature for 2 hours to react a crosslinker. This was referred to as a 1:2.5 (with EDC) sample in a weight ratio of VP1:FMP:58-66 epitope peptide.

(4) 32.4 μl of a MES buffer was added to 155.1 μl of 10 mM FMP:58-66 peptide (GILGFVFTL, SEQ ID No. 3) (molecular weight of 966.9) dissolved in DMSO, and the mixture was added to 75 μl of a MES buffer to make a total of 262.5 μl. Moreover, these buffers were mixed. Thereto was added 7.5 μl of EDC crosslinker (EDC, 22980, Thermo SCIENTIFIC) (10 mg/ml in redistilled water). Furthermore, 30 μl of redistilled water was added to make a total amount of 300 μl. This mixture liquid was incubated at room temperature for 2 hours to react a crosslinker. This was referred to as a peptide alone (with EDC) sample.

(5) 35.04 μl of a MES buffer of the same composition as described above was added to 39.96 μl of SV40 wild type VP1 VLP (3752.7 ng/μl) dialyzed against a MES buffer of the same composition to make a total of 75 μl. 32.4 μl of a MES buffer was added to 155.1 μl of 10 mM FMP:58-66 peptide (GILGFVFTL, SEQ ID No. 3) (molecular weight of 966.9) dissolved in DMSO to make a total of 187.5 μl. Then, these buffers were mixed. Thereto was added 37.5 μl of redistilled water to make a total amount of 300 μl. This mixture liquid was incubated at room temperature for 2 hours. This was referred to as a 1:10 (no EDC) sample in a weight ratio of VP1:FMP:58-66 epitope peptide.

(6) 60 μl of a MES buffer of the same composition as described above was added to 15 μl of bovine serum albumin (BSA) (10 μg/l) dissolved in a MES buffer of the same composition to make a total of 75 μl, as a negative control. 32.4 μl of a MES buffer was added to 155.1 μl of 10 mM FMP:58-66 peptide (GILGFVFTL, SEQ ID No. 3) (molecular weight of 966.9) dissolved in DMSO to make a total of 187.5 μl. Moreover, these buffers were mixed. Thereto was added 7.5 μl of EDC crosslinker (EDC, 22980, Thermo SCIENTIFIC) (10 mg/ml in redistilled water). Furthermore, 30 μl of redistilled water was added to make a total amount of 300 μl. This mixture liquid was incubated at room temperature for 2 hours to react a crosslinker. This was referred to as a 1:10 (with EDC) sample in a weight ratio of BSA:FMP:58-66 peptide.

Figure 3A:
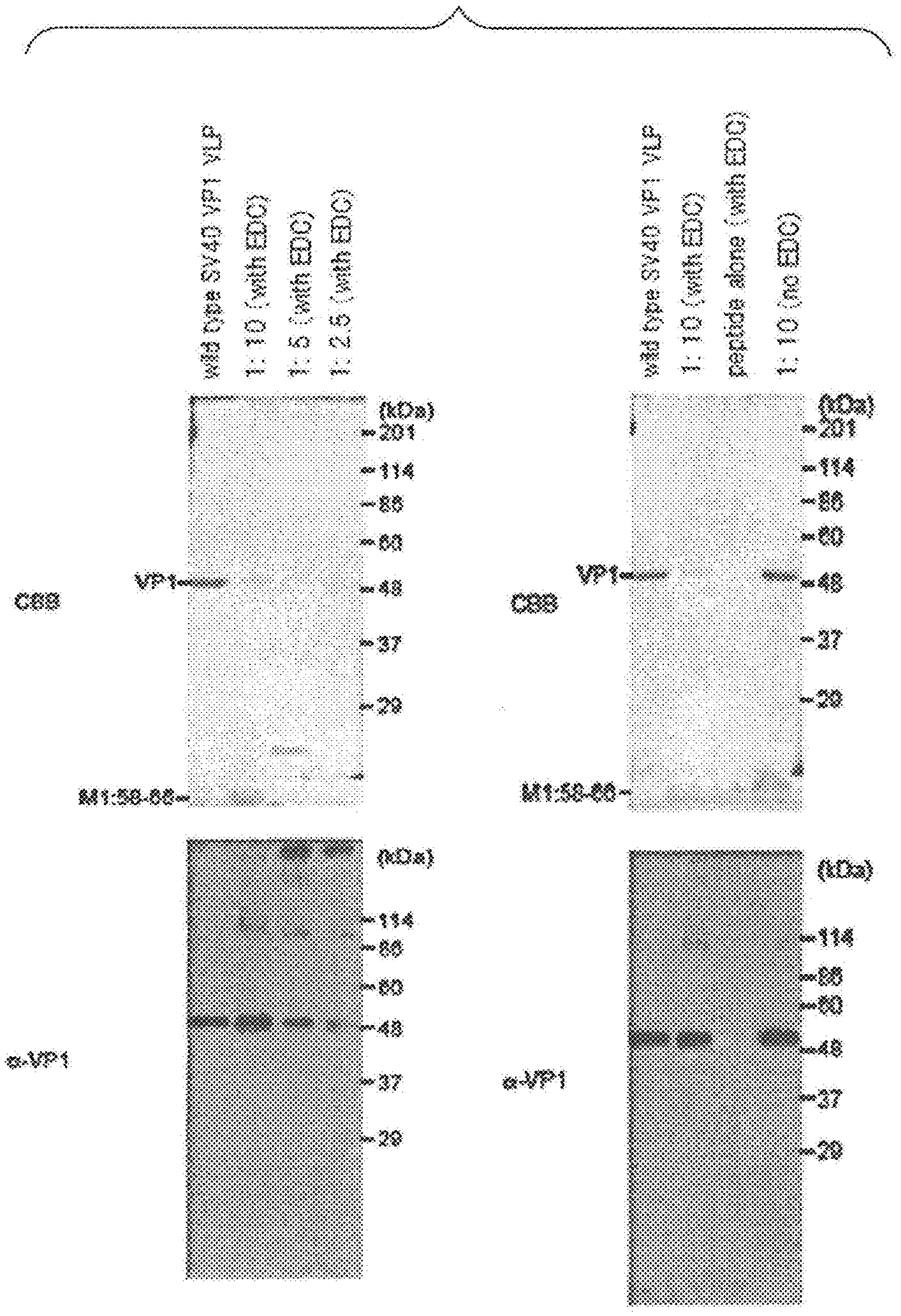
FIG. 3A is photographs showing results of CBB staining and western blotting showing that a crosslinking reaction of wt SV40 VP1 VLP and FMP:58-66 peptide occurs.

1 μl samples of the above (1) to (5) were developed by 10% SDS-PAGE and stained with CBB. 1 μl samples of the above (1) to (5) were developed by 10% SDS-PAGE and then transferred to a PVDF membrane. Western blotting was performed with an anti-SV40 VP1 antibody. The results are shown in FIG. 3A. In FIG. 3A, in the samples of the above (1) to (3) (in FIG. 3A, 1:10 (with EDC), 1:5 (with EDC) and 1:2.5 (with EDC), respectively), bands of 86 to 114 kDa were confirmed in the higher molecular side than VP1 (about 48 kDa), in the gel image of western blotting. It shows that the band of VP1 shifted to the higher molecular side, as a result of the crosslinking reaction of wt SV40 VP1 VLP and FMP:58-66 peptide. On the other hand, when using the samples of the above (4) and (5) (in FIG. 3A, peptide alone (with EDC) and 1:10 (no EDC), respectively), in both CBB staining and western blotting, any band in the higher molecular side than VP1 was not observed. Based on the above results, it was shown that M1 CTL epitope can be added to wt SV40 VP1 VLP, using EDC crosslinker.

Immunization of wt SV40 VP1 VLP

The following experiment used a transgenic mouse using C57BL/6 as a background and expressing a chimera of HLA-A*0201 and H-2Db further fused with human β2m (hereinafter, HHD mouse). This mouse is a β2m and H-2Db knockout mouse, thus it is considered that mouse-derived MHC class I is not exposed to the cell surface.

An 8-week old HHD mouse was immunized with 100 μl of each of the samples of the above (1) to (6) via the intraperitoneal route.

For immunization, a 1 ml syringe with a 27-gauge needle inserted (Myjector, syringe with an injection needle, for insulin, TERUMO, SS-10M2713) was used. After one week from administration, the spleen of the immunized mouse was collected. Lymphocytes were prepared by the following method, and Intra-cellular cytokine staining (ICS) analysis described below was performed.

Preparation of Lymphocytes from Spleen of Mouse

The spleen was removed from the immunized mouse. The spleen was put in a φ6 cm dish with 5 ml of RPMI-1640 medium. The spleen was well loosened in the medium using tweezers, and a solution containing lymphocytes eluted in the medium was transferred to a 15 ml tube. The φ6 cm dish was again washed with 5 ml of RPMI-1640 medium. The supernatant was added to the 15 ml tube so that the total amount was 10 ml. The supernatant was again transferred to a new 15 ml tube, leaving tissue sections deposited at the bottom of the 15 ml tube. The 15 ml tube was centrifuged at 1,200 rpm at room temperature for 5 minutes to obtain a pellet containing lymphocytes. The supernatant was removed, and the pellet was loosened. Thereafter, in order to remove erythrocytes, 250 μl of a $NH_4Cl$-tris solution was added thereto, and the mixture was stirred. Thereafter, 10 ml of RPMI-1640 medium was quickly added thereto, and the 15 ml tube was centrifuged at 1,2000 rpm at room temperature for 5 minutes to obtain a pellet containing lymphocytes. The supernatant was removed, and the pellet was loosened. Thereafter, 10 ml of RPMI-1640 medium was again added thereto. The medium containing lymphocytes was transferred to a new 15 ml tube with a pipette so as not to suck modified erythrocytes as much as possible. The 15 ml tube was again centrifuged at 1,200 rpm at room temperature for 5 minutes. The supernatant was removed, and then the pellet was loosened. The pellet was again suspended in 10 ml of RPMI-1640 medium, and centrifuged at 1,200 rpm at room temperature for 5 minutes. The supernatant was removed, and the pellet was finally suspended in 2 ml of 10% FCS mixing RPMI-1640 medium. In order to count lymphocytes, 10 μl of the above suspension was added to 490 μl of a 2% acetic acid solution. The number of cells was counted with a Burker-Turk hemocytometer. The resulting mixture was diluted with 10% FCS mixing RPMI-1640 medium so as to be $1\times10^7$ cells/ml.

Intra-Cellular Cytokine Staining (ICS) Analysis

After immunizing the mouse, ICS analysis was performed, in order to identify the ratio of CD8 positive IFN-γ positive CTL induced by reacting to FMP:58-66 epitope in the lymphocytes collected from the spleen. BD GolgiPlug (trademark) (BD Biosciences) diluted 25-fold with 10% FCS mixing RPMI-1640 medium was added to a 96-well round-bottom plate, at 5 μl per well. Thereto was further added 100 μl of 20 μM FMP:58-66 epitope (GILGFVFTL, SEQ ID No. 3; Operon) diluted with 10% FCS mixing RPMI-1640 medium. To this well was added 100 μl of the lymphocytes prepared above. Thereafter, the mixture was incubated at 37° C., 5% $CO_2$, for 5 hours.

After incubation at 4° C., the mixture was spun down at 1,400 rpm to remove the supernatant, and the cells were loosened with a Vortex mixer. Thereafter, FACS buffer (2% FCS, 0.1% sodium azide, 1×PBS(−)) was added at 200 μl per well. The mixture was again spun down at 4° C., 1,400 rpm to remove the supernatant, and the cells were loosened. Thereafter, 100 μl of Mouse BD Fc Block (trademark) (BD Pharmingen) diluted to 5 μg/ml with FACS buffer was added thereto, and the mixture was incubated at 4° C. for 10 minutes.

After incubation, the mixture was again spun down at 4° C., 1,400 rpm to remove the supernatant, and the cells were loosened.

Thereafter, FACS buffer was added at 200 μl/well. The mixture was again spun down at 4° C., 1,400 rpm to remove the supernatant. Washing operation using 200 μl/well of FACS buffer was again carried out.

FITC Rat Anti-Mouse CD8a Clone: 53-6.7 (BD Pharmingen) diluted to 10 μg/ml with FACS buffer was added to the loosened cells, at 50 μl per well. The mixture was incubated in a dark place at 4° C. for 30 minutes.

After incubation, washing operation with 200 μl/well of FACS buffer was carried out twice.

Thereafter, 100 μl of BD Cytofix/Cytoperm (trademark) (BD Biosciences) was added to the loosened cells, at 100 μl per well, and the mixture was incubated in a dark place at 4° C. for 20 minutes. After incubation, the washing operation as same as described above was carried out twice, using 200 μl of 1×BD Perm/Wash (trademark) (BD biosciences) in place of the FACS buffer. Thereafter, 50 μl of PE anti-mouse IFN-γClone: XMG1.2 (BioLegend) diluted to 10 μg/ml with 1×BD Perm/Wash (trademark) was added to the loosened cells. The mixture was incubated in a dark place at 4° C. for 30 minutes.

After incubation, the washing operation as same as described above was carried out twice, using 200 μl of 1×BD Perm/Wash (registered trademark). Thereafter, FACS fixation buffer (1% formaldehyde, 1×FACS buffer) was added to the loosened cells, at 100 μl per well, and the mixture was incubated in a dark place at 4° C. overnight.

After incubation, 400 μl of FACS buffer was added to 5 ml of a polystyrene tube (BD Falcon®, 5 ml polystyrene round-bottom tube 12×75 mm style). Thereto was added the sample fixed with 100 μl of FACS fixation buffer. Thereafter, dot plot analysis was performed with FACScan™ (Becton Dickinson). Cell Quest (Becton Dickinson) software was used for the analysis.

Figure 3B:
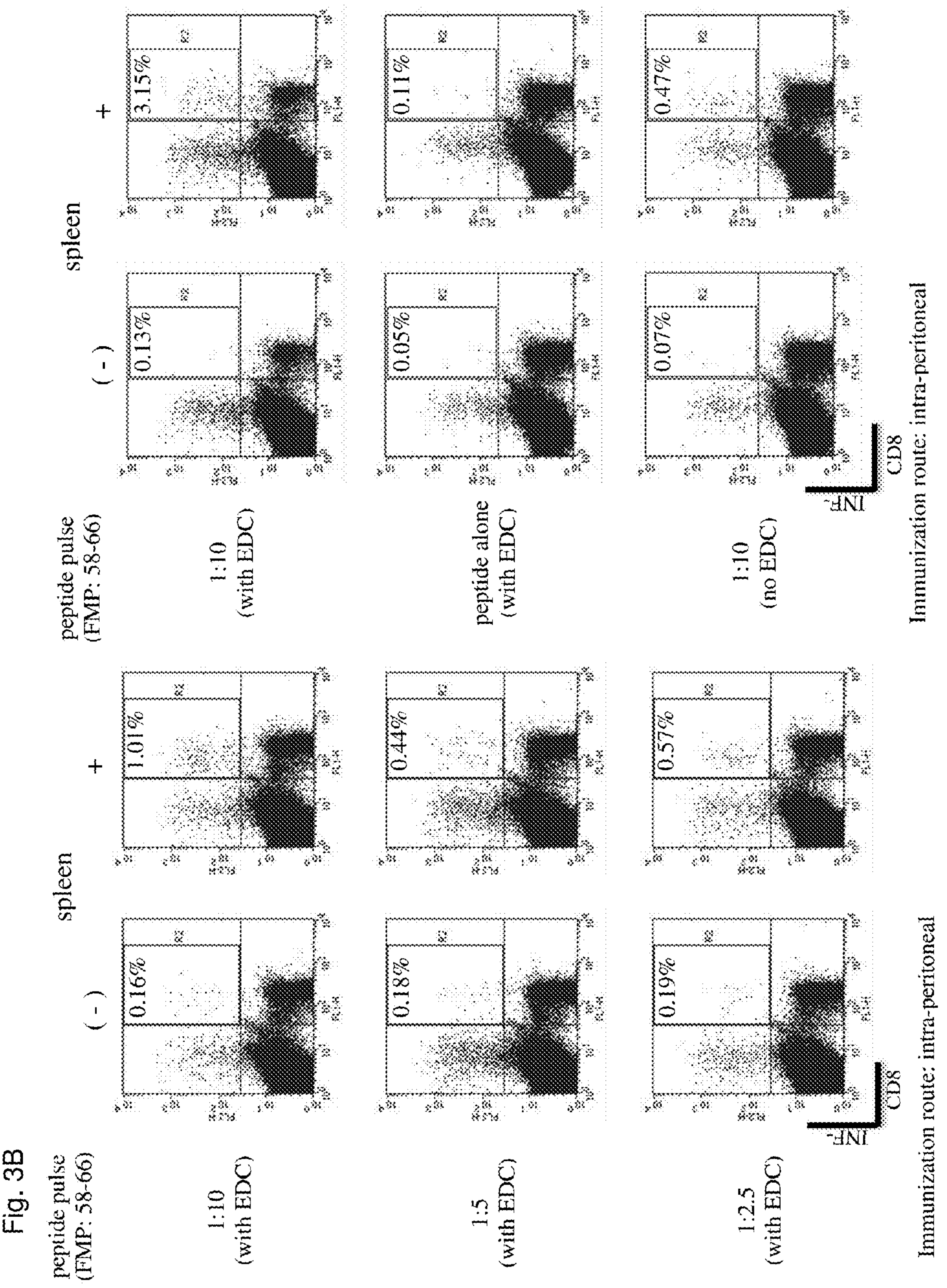
FIG. 3B is figures showing a result of ICS analysis performed for lymphocytes prepared from the spleen of a mouse intraperitoneally immunized with wt SV40 VP1 VLP with FMP:58-66 peptide immobilized thereon.
Figure 3C:
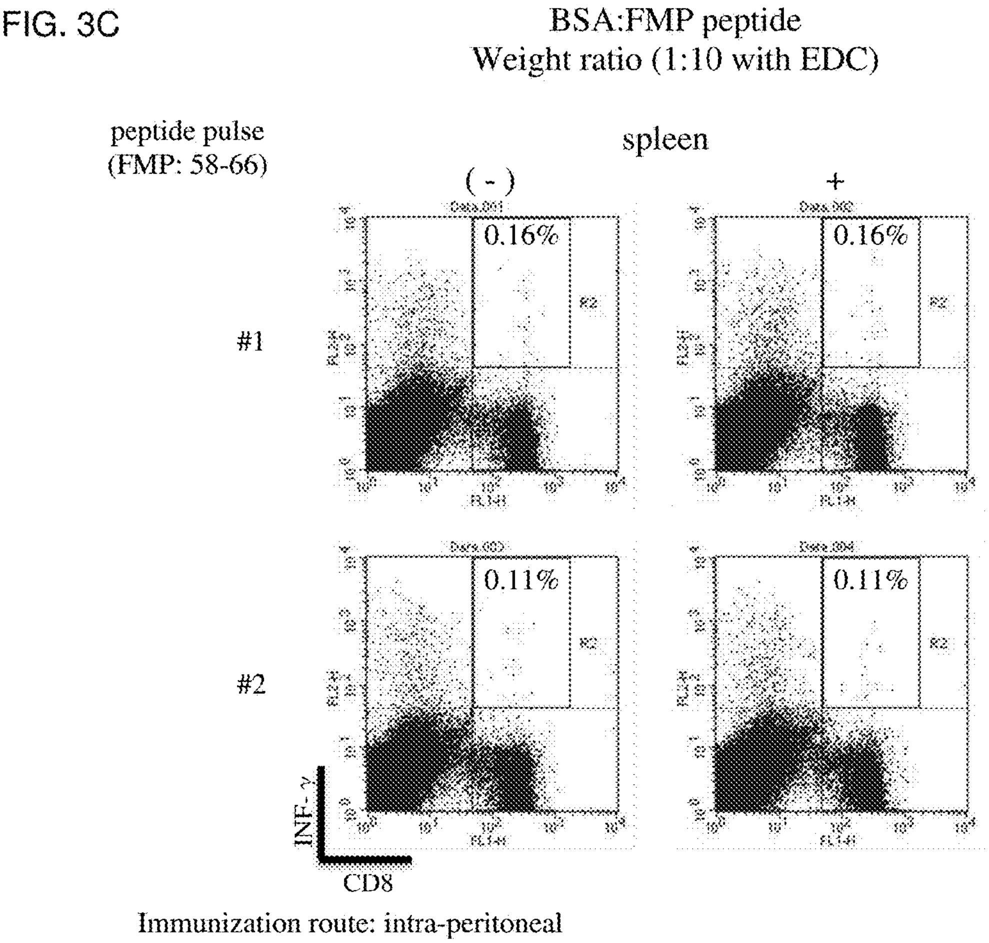
FIG. 3C is figures showing a result of ICS analysis performed for lymphocytes prepared from the spleen of a mouse intraperitoneally immunized with BSA with FMP:58-66 peptide immobilized thereon.

The results of ICS analysis are shown in FIG. 3B and FIG. 3C. In a scattergram by each dot plot, the horizontal axis shows an expression level of CD8. The higher the CD8 expression level, the plot of the cells shifts to the right side. The vertical axis shows an expression level of IFN-γ. The higher the IFN-γ expression level, the plot of the cells shifts to the upper side. In this analysis, $CD8^+IFN\text{-}\gamma^+T$ cells are plotted in an upper right quadrant divided by two straight lines each parallel to the vertical axis and the horizontal axis in the scattergram. The numerical value (%) in the same quadrant shows a percentage of $CD8^+IFN\text{-}\gamma^+T$ cells of the whole CD8 positive cells of the ICS analysis. The CD8 positive cell is also called as a cytotoxic T lymphocyte (CTL), and releases perforin, Granzyme B and the like to virus-infected cells, tumor cells and the like to induce apoptosis. IFN-γ is a type of cytokines produced by activated CD8 cells. In FIG. 3B, when using the sample of the above (1) (1:10 (with EDC)) (two pairs are shown), the percentages of $CD8^+IFN\text{-}\gamma^+T$ cells were greatly increased, in that the percentages of $CD8^+IFN\text{-}\gamma^+T$ cells were 1.01% and 3.15% in mouse lymphocytes with immunity (+) while the percentages were 0.16% and 0.13% in mouse lymphocytes with no immunity (−). Also when using the samples of the above (2) and (3) (1:5 (with EDC) and 1:2.5 (with EDC), respectively), the same thing was observed. These results show that FMP:58-66 epitope-specific cytotoxic T lymphocyte was induced by FMP:58-66 epitope addition after intraperitoneal immunization of wt SV40 VP1 VLP with FMP:58-66 epitope immobilized thereon. It became clear that the number of the induced epitope-specific CTL tends to increase, as the amount of epitope added is larger. Furthermore, when using the sample of the above (5) (1:10 (no EDC)), the percentage of $CD8^+IFN\text{-}\gamma^+T$ cells greatly increased. Based on the result of the sample (5), it is considered that, even when an epitope peptide is not added to wt SV40 VP1 VLP, CTL of mouse lymphocytes can be induced as well as immunization by epitope peptide-added wt SV40 VP1 VLP, by immunization with both. On the other hand, in the sample of the above (4) with peptide alone (peptide alone (with EDC)), the great increase in the percentage of $CD8^+IFN\text{-}\gamma^+T$ cells was not observed. In samples containing mouse lymphocytes immunized with BSA cross-linked with FMP:58-66 peptide (negative control, two pairs are shown in FIG. 3C), the great increase in the percentage was not observed, and FMP:58-66 epitope-specific CTL was never efficiently induced (FIG. 3C).

Based on these results, the possibility that the induction ability of epitope-specific CTL is high, and VLP is involved in CTL, in the sample containing mouse lymphocytes immunized with VLP with FMP:58-66 epitope immobilized thereon, was suggested. The induction ability of epitope-specific CTL was low even when immobilizing epitope on BSA. Thus, it was suggested that wt SV40 VP1 VLP is necessary for effectively inducing epitope-specific CTL.

$^{51}$Chrome Release Analysis

In order to show that a CD8 positive intracellular IFN-γ positive cell damages cells, $^{51}$Chrome release analysis was performed. Lymphocytes of the spleen of a non-immunized HHD mouse were prepared by the same method as described above. 4 μl of a peptide of 10 mM CTL epitope of M1 (FMP:58-66 peptide; GILGFVFTL, SEQ ID No. 3; Operon) was added to $2.4\times10^8$ spleen lymphocytes of a non-immune mouse in 2 ml of 10% FCS mixing RPMI-1640 medium in a 15 ml tube. The mixture was incubated at 37° C., 5% $CO_2$ incubator, for 2 hours. After incubation, 20 Gy (gray) X ray was irradiated. After irradiation, the 15 ml tube was centrifuged at 1,200 rpm at room temperature for 5 minutes to obtain a pellet containing lymphocytes. The supernatant was removed, and the pellet was loosened. Thereafter, 2 ml of 10% FCS mixing RPMI-1640 medium was added thereto. In order to count lymphocytes, 10 μl of the lymphocyte solution was added to 490 μl of a 2% acetic acid solution. The number of cells was counted with a Burker-Turk hemocytometer. The resulting mixture was diluted with 10% FCS mixing RPMI-1640 medium so as to be $5\times10^6$ cells/ml.

On the other hand, 50 μl of a VLP solution (1:10 (with EDC)) with FMP:58-66 peptide immobilized thereon was immunized by intraperitoneal immunization. After 1 week of immunization, the spleen was removed from the mouse. The spleen was put in a φ6 cm dish each with 5 ml of RPMI-1640 medium. The spleen was well loosened in the medium using tweezers, and a solution containing lymphocytes eluted in the medium was transferred to a 15 ml tube. The φ6 cm dish was again washed with 5 ml of RPMI-1640 medium. The supernatant was added to the 15 ml tube so that the total amount was 10 ml. The blood was not removed from the immunized lymphocytes. Therefore, then the supernatant was again transferred to a new 15 ml tube, leaving tissue sections deposited at the bottom of the 15 ml tube. The 15 ml tube was centrifuged at 1,200 rpm at room temperature for 5 minutes to obtain a pellet containing lymphocytes. The supernatant was removed, and the pellet was loosened. Thereafter, 2 ml of 10% FCS mixing RPMI-1640 medium was added thereto. In order to count lymphocytes, 10 μl of the lymphocyte solution was added to 490 μl of a 2% acetic acid solution. The number of cells was counted with a Burker-Turk hemocytometer. The resulting mixture was diluted with 10% FCS mixing RPMI-1640 medium so as to be $5\times10^6$ cells/ml.

In a 48-well plate, 500 μl/well of the above X-ray irradiated non-immune lymphocytes ($5\times10^6$ cells/ml) after incubated with peptide of M1 CTL epitope and 500 μl/well of the above immunized lymphocytes ($5\times10^6$ cells/ml) were mixed. 24 wells of this well were prepared per sample. After mixing, the plate was incubated at 37° C., 5% $CO_2$ incubator, for 7 days.

Thereafter, the lymphocytes in the 24 wells were collected in one 50 ml tube. The 15 ml tube was centrifuged at 1,200 rpm at room temperature for 5 minutes to obtain a pellet containing lymphocytes. The supernatant was removed, and the pellet was loosened. Thereafter, 2 ml of 10% FCS mixing RPMI-1640 medium was added thereto. In order to count lymphocytes, 20 μl of the lymphocyte solution was added to 20 μl of a 0.4% Trypan blue solution (Gibco). The number of cells was counted with a Burker-Turk hemocytometer. The resulting mixture was diluted with 10% FCS mixing RPMI-1640 medium or concentrated so as to be $7.5\times10^6$ cells/ml. The lymphocytes prepared as described above were referred to as effector cells.

On the other hand, 1 ml each of $1\times10^6$ cells/ml RMA-HHD cultured cells was dispensed into two 15 ml tubes. To one tube was added 5 μl of a peptide of 10 mM M1 CTL epitope (GILGFVFTL, SEQ ID No. 3; Operon). To other tube was not added a peptide. These tubes were each incubated at 37° C., 5% $CO_2$ incubator, for 2 hours. Thereafter, the 15 ml tube was centrifuged at 1,200 rpm at room temperature for 5 minutes to obtain a pellet containing the cells. The supernatant was removed, and the pellet was loosened. Thereafter, 100 μCi (microsievert) of a $Na_2{}^{51}CrO_4$ solution was added. The mixture was incubated at 37° C., 5% $CO_2$ incubator, for 30 minutes. Thereafter, the 15 ml tube was centrifuged at 1,200 rpm at room temperature for 5 minutes to obtain a pellet containing the cells. The supernatant was removed, and the pellet was loosened. Thereafter, 1 ml of 10% FCS mixing RPMI-1640 medium was added thereto, for washing operations. The 15 ml tube was centrifuged at 1,200 rpm at room temperature for 5 minutes to form a pellet containing lymphocytes. Then, the supernatant was removed. The washing operations were repeated five times. Finally, after removing the supernatant, 1 ml of 10% FCS mixing RPMI-1640 medium was added thereto. In a new 15 ml tube, 500 μl of this cell solution and 9.5 ml of 10% FCS mixing RPMI-1640 medium were mixed, and the mixture was diluted 20-fold. This diluted cell solution was referred to as a target cell fluid.

Into a 96-well plate was dispensed 100 μl of the target cell fluid ($5\times10^3$ cells). Thereto was each added 100 μl ($7.5\times10^5$ cells) of the effector cell fluid, a mixed liquid of 20 μl ($1.5\times10^5$ cells) of the effector cell fluid and 80 μl of 10% FCS mixing RPMI-1640 medium, and a mixed liquid of 10 μl ($7.5\times10^4$ cells) of the effector cell fluid and 90 μl of 10% FCS mixing RPMI-1640 medium, so that the ratios of effector cells:target cells became 150:1, 30:1, and 15:1, respectively. To 100 μl of the target cell fluid ($5\times10^3$ cells) was added 100 μl of a 5% Triton-X 100 solution as a positive control, and 100 μl of a 10% FCS mixing RPMI-1640 medium as a negative control, respectively. After mixing, the plate was incubated at 37° C., 5% $CO_2$ incubator, for 4 hours.

Thereafter, the supernatant was collected using Supernatant collection system (Molecular Devices). The released $^{51}Cr$ gamma ray was counted and analyzed with AUTO WELL GAMMA SYSTEM (ARC-380CL, Aloka) and ALOKA RIA Program (ARCAS ver. 3.11, Aloka). % Specific lysis was calculated by 100×(count (sample)−count (negative control))/(count (positive control)−count (negative control)).

Figure 3D:
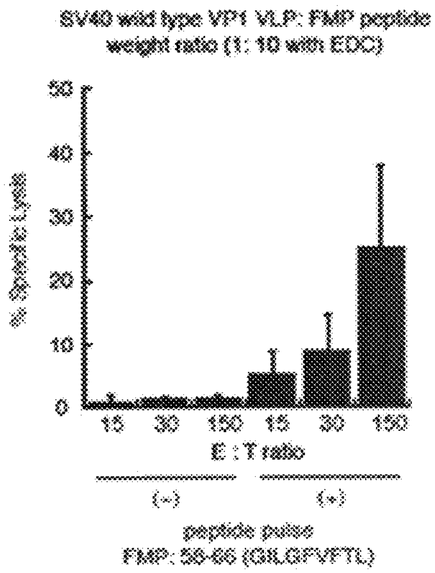
FIG. 3D is figures showing a result of $^{51}$Chrome release analysis performed for lymphocytes prepared from the spleen of a mouse immunized with wt SV40 VP1 VLP with FMP:58-66 peptide immobilized thereon by intraperitoneally administration.

The result is shown in FIG. 3D. Elution of $^{51}Cr$ was hardly observed in the case of no immunity (−). On the other hand, in the case of immunity (+), it was confirmed that $^{51}Cr$ in the cytoplasm was eluted since the cell membrane of the target cells (RMA-HHD cells) attacked by CTL was damaged, also in any ratio of effector cells:target cells. It was shown that the eluted $^{51}Cr$ amount is also increased as the amount of the effector cells added is increased. Based on the above, it was certainly shown that immunological activity on immobilized peptide can be induced by immunization of wt SV40 VP1 VLP with FMP:58-66 peptide immobilized thereon.

Example 2: Detection of Increase in CD86 Molecule by wt SV40 VP1 VLP Stimulation in Mouse Lymphocytes Increase in Expression of CD86 Molecule by wt SV40 VP1 VLP The purified VP1 VLP fraction prepared in Example 1 was used as a wt SV40 VP1 VLP solution. To a 96-well flat-bottom plate was added 5 μl of a wt SV40 VP1 VLP solution (500 μg/ml in PBS(−)). Meanwhile, a well to which a wt SV40 VP1 VLP solution was not added was prepared in a round-bottom plate. To a separate flat-bottom plate was added 5 μl of PBS(−) buffer. Meanwhile, a separate well to which PBS(−) buffer was not added was prepared in a round-bottom plate. Thereto were added $5\times10^5$ lymphocytes prepared as described in Example 1, except for using the spleen of non-immune HHD mouse in place of that of the intraperitoneally immunized mouse. Thereto was added R10 medium (a medium added to have final concentrations of 10% FCS, 100 U/ml penicilin, 100 μg/ml streptomycin, 2 mM L—glutamine, 50 μM 2-mercaptoethanol, to RPMI-1640 medium (Sigma); the same composition as the 10% FCS mixing RPMI-1640 medium) so as to be a total amount of 200 μl. Thereafter, the plate was incubated at an incubator at 37° C., 5% $CO_2$, for 24 hours.

Figure 4A:
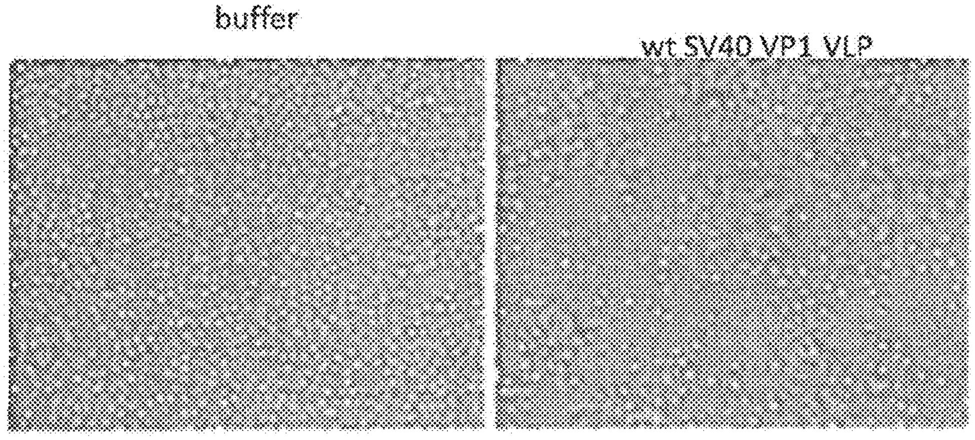
FIG. 4A is photographs showing proliferation of lymphocytes derived from a non-immune mouse stimulated with wt SV40 VP1 VLP.

In order to observe cell proliferation of lymphocytes by SV40 VP1 VLP stimulation, for a well added with a wt SV40 VP1 VLP solution and a well added with PBS(−) buffer in a flat-bottom plate, the cells were observed under an inverted phase contrast microscope. The cells were observed at ×200. The result is shown in FIG. 4A. In FIG. 4A, in the well added with PBS(−) alone with no stimulation (buffer, in FIG. 4A), lymphocytes were uniformly distributed without proliferating. On the other hand, in the well added with SV40 VP1 VLP stimulation (wt SV40 VP1 VLP, in FIG. 4A), it was observed that lymphocytes proliferated, and a cluster was formed. Therefore, it became clear that lymphocytes can be activated by wt SV40 VP1 VLP stimulation.

A well added with a wt SV40 VP1 VLP solution, a well added with PBS(−) buffer and a well with only R10 medium and lymphocytes in the round-bottom plate after incubation for 24 hours described above were spun down at 4° C., 1,400 rpm. The supernatant was removed, and the cells were loosened with a Vortex mixer. Thereafter, FACS buffer (2% FCS, 0.1% sodium azide, 1×PBS(−)) was added at 200 μl/well. The mixture was again spun down at 4° C., 1,400 rpm to remove the supernatant, and the cells were loosened. Thereafter, 100 μl of LEAF Purified Rat Anti-Mouse CD16/32 Clone: 93 (BioLegend) diluted to 20 μg/ml with FACS buffer was added thereto, and the mixture was incubated at 4° C. for 10 minutes. Thereafter, washing operation with 200 μl of FACS buffer was carried out once. 50 μl each of PE Rat Anti-Mouse CD86 Clone: GL-1 (BioLegend) diluted to 10 μg/ml with FACS buffer was added to the loosened cells. The mixture was incubated in a dark place at 4° C. for 30 minutes. Thereafter, washing operation with 200 μl of FACS buffer was carried out twice. Thereafter, FACS fixation buffer (1% formaldehyde, 1×FACS buffer) was added to the loosened cells, at 100 μl per well. The mixture was incubated in a dark place at 4° C. overnight. Thereafter, 400 μl of FACS buffer was added to 5 ml of a polystyrene tube (BD Falcon®, 5 ml polystyrene round-bottom tube 12×75 mm style). Thereto was added the sample fixed with 100 μl of FACS fixation buffer. Histogram analysis was performed with FACScan™ (Becton Dickinson). Cell Quest (Becton Dickinson) software was used for the analysis.

Figure 4B:
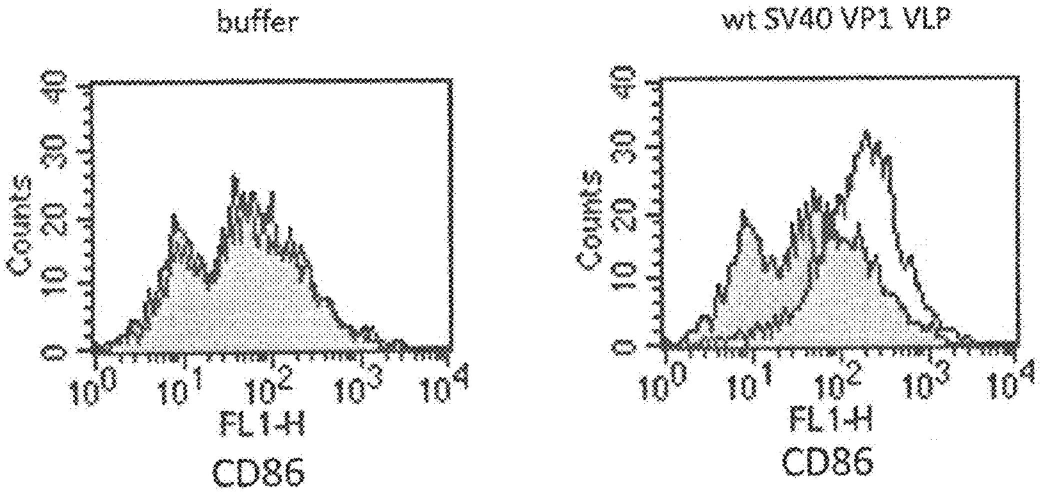
FIG. 4B is diagrams showing a FACScan™ analysis result showing CD86 expression in lymphocytes derived from a non-immune mouse stimulated with wt SV40 VP1 VLP.

The results are shown in FIG. 4B. FIG. 4B is a histogram showing fluorescence intensity of anti-CD86 antibody and the number of cells corresponding to the fluorescence intensity. In FIG. 4B, the gray histogram shows the number of cells in each fluorescence intensity when incubated with R10 medium alone without adding a wt SV40 VP1 VLP solution and PBS(−) buffer. The outlined histogram shows the number of cells in each fluorescence intensity when incubated with R10 medium added with a wt SV40 VP1 VLP solution (right figure, in FIG. 4B) or R10 medium added with PBS(−) buffer (left figure, in FIG. 4B). As a result of analysis, the outlined peak for mouse lymphocytes stimulated with PBS (−) buffer alone nearly overlapped with the gray peak (left figure, in FIG. 4B). On the other hand, the outlined peak for the mouse lymphocytes stimulated with wt SV40 VP1 VLP shifted to the right side as compared with the gray peak (right figure, in FIG. 4B). It shows that, when stimulated with wt SV40 VP1 VLP, cells highly expressing CD86 molecule increased. Based on the above, it became clear that wt SV40 VP1 VLP induces increase in expression of CD86 molecule, in the mouse lymphocytes.

Comparative Example 1: Detection of Increase in CD86 Molecule by M1 CTL Epitope-Inserted SV40 VP1 VLP Stimulation in Mouse Lymphocytes Preparation of Baculovirus Expressing M CTL Epitope-Inserted SV40 VP1

A CTL epitope sequence (FMP:58-66 epitope (influenza Matrix Protein 58-66 epitope): GILGFVFTL, SEQ ID No. 3) (this epitope sequence is an epitope sequence for HLA-A*0201 of human MHC class I) of an influenza virus particle internal protein matrix protein 1 (M1) was inserted into SV40 VP1. Specifically, a DE loop region (137 to 138 amino acid region, classically, 4th Ala of a VP1 gene as amino acid No. 1) or an HI loop region (273 to 274 amino acid region) of VP1 was replaced with GILGFVFTL (SEQ ID No. 3) in which three glycines are added at the amino terminal and the carboxyl terminal to prepare a M1 CTL epitope-inserted SV40 VP1 insertion mutant (FMP-DE-VP1, FMP-HIVP1). The mutant was prepared by the Overhang PCR method by employing pFastBac 1-SV40 wild type VP1 encoding SV40 VP1 as a template. The following primers were used.

Primers for Preparing FMP-DE-VP1

```
1st round
5'-SalI-Kozac-SV40 VP1
                                        (SEQ ID No. 4)
AAAAGTCGACACCATGAAGATGGCCCCAACAAAAAG

3'-DE2 loop (M1)
                                        (SEQ ID No. 5)
CGTGAACACAAAGCCCAAAATGCCGCCACCGCCATGAGT
TTTTTGTGTCCCTGAATG

5'-DE2 loop (M1)
                                        (SEQ ID No. 6)
CATTTTGGGCTTTGTGTTCACGTTGGGCGGCGGTGGTGC
TGGAAAACCCATTCAAG

3'-KpnI-SV40 VP1
                                        (SEQ ID No. 7)
AAAAGGTACCTCACTGCATTCTAGTTGTGGTTTG

2nd round
5'-SalI-Kozac-SV40 VP1
                                        (SEQ ID No. 4)
AAAAGTCGACACCATGAAGATGGCCCCAACAAAAAG

3'-KpnI-SV40 VP1
                                        (SEQ ID No. 7)
AAAAGGTACCTCACTGCATTCTAGTTTGTGGTTTG
```

Primers for Preparing FMP-HI-VP1

```
1st round
5'-SalI-Kozac-SV40 VP1
                                        (SEQ ID No. 4)
AAAAGTCGACACCATGAAGATGGCCCCAACAAAAAG

3'-HI1 loop (M1)
                                        (SEQ ID No. 8)
CGTGAACACAAAGCCCAAAATGCCGCCACCGCCGTTGGT
AAACAGCCCACAAATG

5'-HI1 loop (M1)
                                        (SEQ ID No. 9)
CATTTTGGGCTTTGTGTTCACGTTGGGCGGCGGTGGAAC
ACAGCAGTGGAAGGG

3'-KpnI-SV40 VP1
                                        (SEQ ID No. 7)
AAAAGGTACCTCACTGCATTCTAGTTGTGGTTTG

2nd round
5'-SalI-Kozac-SV40 VP1
                                        (SEQ ID No. 4)
AAAAGTCGACACCATGAAGATGGCCCCAACAAAAAG

3'-KpnI-SV40 VP1
                                        (SEQ ID No. 7)
AAAAGGTACCTCACTGCATTCTAGTTGTGGTTTG
```

10 ng of a template was employed. Each 50 pmol of primers was added to prepare 30 μL of a mixed solution containing 2.5 units of a KOD polymerase (TOYOBO), 0.2 mM dNTPs, 1 mM $MgCl_2$, 6 mM $(NH_4)_2SO_4$, 10 mM KCl, 120 mM Tris-HCl (pH 8.0), 0.1% Triton X-100, and 0.001% BSA.

In PCR, in both of 1st round and 2nd round, after incubation at 98° C. for 60 seconds, the following cycle was repeated 25 times (98° C. for 15 seconds, 59° C. for 15 seconds, 74° C. for 30 seconds) and finally, incubation was performed at 74° C. for 1 minute and 30 seconds, and the procedure was migrated to 4° C.

PCR fragments prepared by the Overhang PCR were cut with restriction enzymes KpnI and SalI. The cut PCR fragments were inserted between KpnI and SalI sites of a pFastBac 1 plasmid vector to obtain FMP-DE-VP1 and FMP-HI-VP1 plasmids. *Escherichia coli* DH10bac (invitrogen) holding a baculovirus genome was transformed with each plasmid to prepare a recombinant baculovirus genome with the coding sequence of loop region epitope-inserted VP1 incorporated therein. The recombinant baculovirus genome was transfected to Sf-9 cells. After three days, the supernatant thereof was collected to obtain a solution containing recombinant baculovirus. A part of this solution was again infected with Sf-9 cells, thereby increasing a recombinant baculovirus titer. The resulting solution was referred to as a stock solution of a recombinant baculovirus.

Preparation of FMP-DE-VLP and FMP-HI-VLP

A recombinant baculovirus with FMP-DE-VP1 or FMP-HI-VP1 incorporated therein was infected with Sf-9 cells ($3\times10^7$) were inoculated at a multiplicity of infection of 0.05 to 0.2 (M.O.I. base). Three days after infection, the Sf-9 cells were collected and then washed with PBS(−). Thereafter, the cells were resuspended in 1 ml of buffer for VP1 ultrasonic treatment (20 mM Tris-HCl (pH 7.9), 1% sodium deoxycholate (Sigma), 2 μM phenylmethanesulfonyl fluoride (Sigma), 1 μg/ml chymostatin (Sigma), 1 μg/ml aprotinin (Sigma), 1 μg/ml leupeptin (Sigma), 1 μg/ml antipain (Sigma) and 1 μg/ml pepstatin (Sigma)), and ultrasonic-crushed. Thereafter, the crushed substance was centrifuged at 15,000 rpm, 4° C. for 5 minutes to separate into supernatant and pellet, and the supernatant was removed. To the remaining pellet was added 200 μl of a 50% Opti-prep™ solution (20 mM Tris-HCl (pH 7.9), 50% Opti-prep™), and the mixture was resuspended by ultrasonication. The resuspension was referred to as a pellet solution (a FMP-DE-VLP solution and a FMP-HI-VLP solution, respectively).

Preparation of Lymphocytes from Spleen of Mouse

The lymphocytes were prepared from the spleen of mouse as described in Example 1, except for using the spleen of non-immune HHD mouse in place of that of the intraperitoneally immunized mouse.

Increase in Expression of CD86 Molecule by FMP-DE-VLP Stimulation and FMP-HI-VLP Stimulation An Opti-prep™ buffer, a FMP-DE-VLP solution (500 μg/ml in 20 mM Tris-HCl (pH 7.9) and 50% Opti-prep™), and a FMP-HI-VLP solution (500 μg/ml in 20 mM Tris-HCl (pH 7.9) and 50% Opti-prep™) were added to a 96-well round-bottom plate at each 5 μl/well. Thereto were added $5\times10^5$ mouse lymphocytes. The R10 medium was added so as to be a total amount of 200 μl. Thereafter, the plate was incubated at an incubator at 37° C., 5% $CO_2$, for 24 hours.

After incubation, pretreatment of FACScan™ was performed as described in Example 2, and histogram analysis was performed with FACScan™ (Becton Dickinson). Cell Quest (Becton Dickinson) software was used for the analysis.

Figure 5:
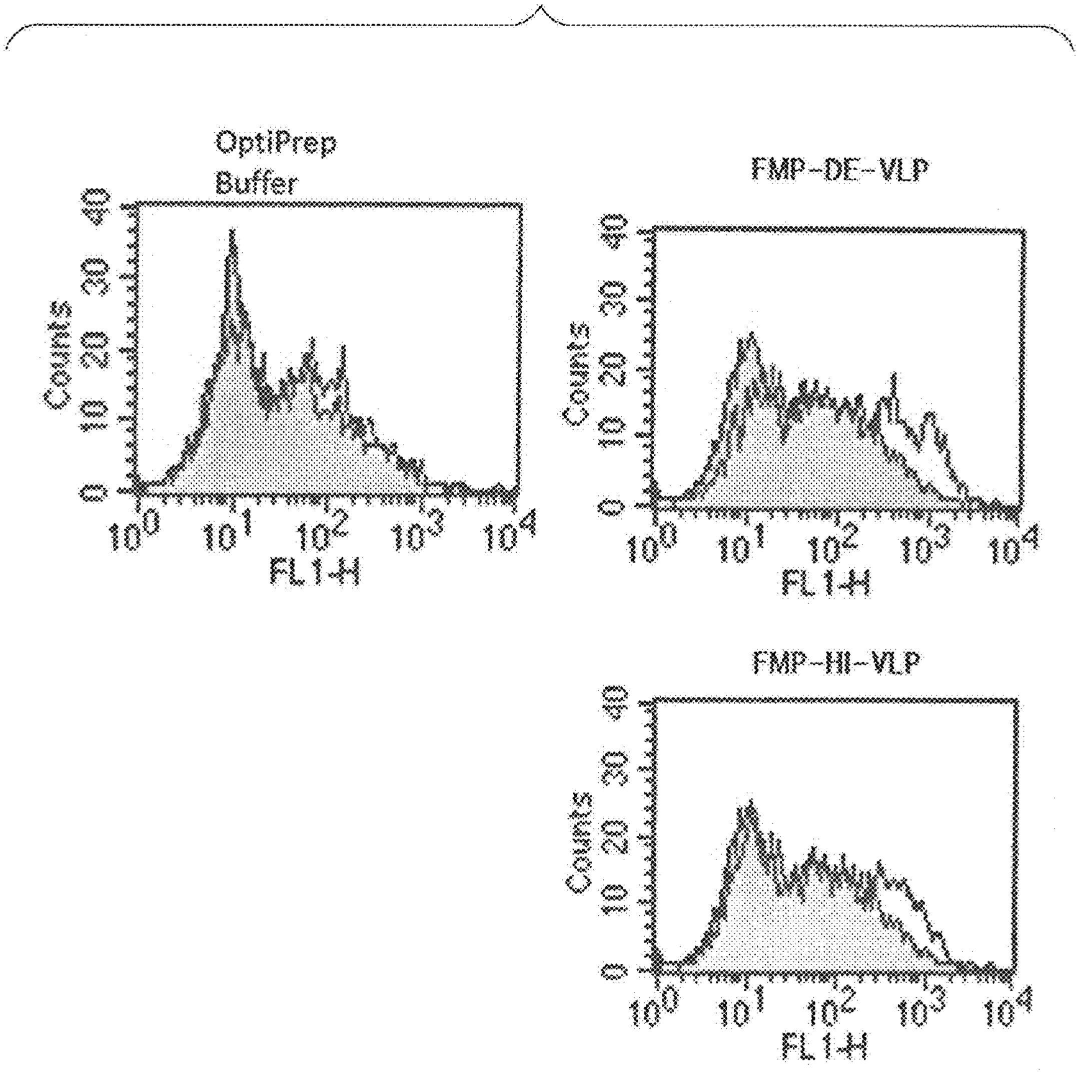
FIG. 5 is diagrams showing a FACScan™ analysis result showing CD86 expression in lymphocytes derived from a non-immune mouse stimulated with FMP-DE-VLP or FMP-HI-VLP.

The result is shown in FIG. 5. When the mouse lymphocytes were stimulated with a sample containing FMP-DE-VLP or a sample containing FMP-HI-VLP, enhancement of fluorescence intensity was slightly found (upper right figure and lower right figure in FIG. 5). However, as compared to the result of Example 2, the increase of fluorescence intensity was markedly low (right figure in FIG. 4B and right figure in FIG. 5). Based on the above, according to the method in Example 2, lymphocytes can be remarkably activated as compared to Comparative Example 1.

Example 3: Detection of Increase in Ganglioside GM1 Dependent CD86 Molecule in SV40 Wild Type VP1 VLP Stimulation Preparation of Baculovirus Expressing Wild-Type (wt) Simian Virus 40 (SV40) VP1

A baculovirus expressing wt SV40 VP1 was prepared by the same method as described in Example 1.

Preparation of wt SV40 VP1 Virus-Like Particles (VLP)

wt SV40 VP1 VLP was prepared by the same method as described in Example 1.

Preparation of Baculovirus Expressing M1 CTL Epitope-Inserted SV40 VP1

A baculovirus expressing M1 CTL epitope-inserted SV40 VP1 was prepared by the same method as described in Comparative Example 1.

Preparation of FMP-DE-VLP and FMP-HI-VLP

FMP-DE-VLP and FMP-HI-VLP were prepared by the same method as described in Comparative Example 1.

Preparation of Lymphocytes from Spleen of Mouse

The lymphocytes were prepared from the spleen of mouse as described in Example 1, except for using the spleen of non-immune HHD mouse in place of that of the intraperitoneally immunized mouse.

Effect of Ganglioside on Increase in Expression of CD Molecule by wt SV40 VP1 VLP Stimulation A wt SV40 VP1 VLP sample was prepared as follows. To a 96-well round-bottom plate was added a wt SV40 VP1 VLP solution (500 μg/ml in PBS(−)) at 5 μl/well. Thereto were added $5\times10^5$ lymphocytes prepared from the spleen of non-immune HHD mouse. The R10 medium was added so as to be a total amount of 200 μl. Thereafter, the plate was incubated at an incubator at 37° C., 5% $CO_2$, for 24 hours.

A GM1-treated wt SV40 VP1 VLP sample and a GD1a-treated wt SV40 VP1 VLP sample were prepared as follows. To a 96-well round-bottom plate was added a wt SV40 VP1 VLP solution (500 μg/ml in PBS(−)) at 5 μl/well. Thereto was added 100 μl of a ganglioside GM1 solution (20 μg/ml in the R10 medium) that is a type of glycolipids, a receptor of SV40, or 100 μl of a ganglioside GD1a solution (20 μg/ml in the R10 medium) that is a type of glycolipids, not a receptor of SV40. The mixture was incubated at 37° C., 5% $CO_2$ incubator, for 1 hour. After incubation, thereto were added $5\times10^5$ lymphocytes prepared from the spleen of non-immune HHD mouse. The R10 medium was added so as to be a total amount of 200 μl. Thereafter, the plate was incubated at an incubator at 37° C., 5% $CO_2$, for 24 hours.

To a 96-well round-bottom plate was added PBS(−) at 5 μl/well, as a control. Thereto were added $5\times10^5$ lymphocytes prepared from the spleen of non-immune HHD mouse. The R10 medium was added so as to be a total amount of 200 μl. Thereafter, the plate was incubated at an incubator at 37° C., 5% $CO_2$, for 24 hours.

After incubation, pretreatment of FACScan™ (Becton Dickinson) was performed as described in Example 2, and histogram analysis was performed with FACScan™ (Becton Dickinson). Cell Quest (Becton Dickinson) software was used for the analysis.

Figure 6A:
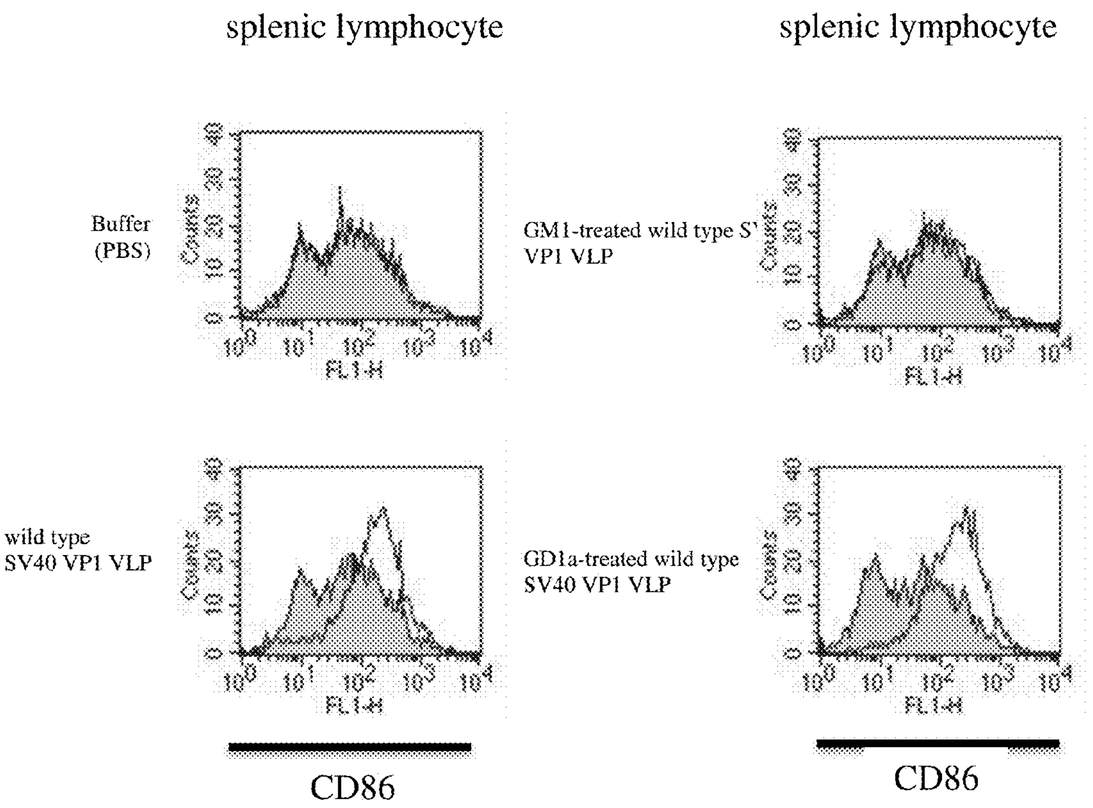
FIG. 6A is diagrams showing a FACScan™ analysis result showing an effect of GM1 or GD1a treatment on CD86 expression induction in lymphocytes derived from a non-immune mouse stimulated with wt SV40 VP1 VLP.

The results are shown in FIG. 6A. As shown in FIG. 6A, shifts of the outlined peaks to the right side were observed in the lymphocytes incubated with a wt SV40 VP1 VLP sample and a GD1a-treated wt SV40 VP1 VLP sample (lower left figure and lower right figure in FIG. 6A), and CD86 expression induction was suggested. On the other hand, the outlined peak nearly overlaps with the gray peak in the lymphocytes incubated with a GM1-treated wt SV40 VP1 VLP sample (upper right figure in FIG. 6A), and CD86 expression induction was not observed. Therefore, it became clear that expression induction of CD86 molecule is not inhibited in incubation with GD1a, but is inhibited in incubation with GM1. Based on the above, expression induction of CD86 molecule by wt SV40 VP1 VLP occurs through binding between wt SV40 VP1 VLP and GM1, thus it was suggested that wt SV40 VP1 VLP needs to bind with ganglioside GM1 on the surface of lymphocytes for increasing CD86 expression by wt SV40 VP1 VLP.

Effect of Ganglioside on Increase in Expression of CD86 Molecule by FMP-DE-VLP Stimulation and FMP-HI-VLP Stimulation A FMP-DE-VLP sample and a FMP-HI-VLP sample were prepared as follows. The FMP-DE-VLP solution (500 μg/ml in 20 mM Tris-HCl (pH 7.9) and 50% Opti-prep™) prepared in Comparative Example 1, and the FMP-HI-VLP solution (500 μg/ml in 20 mM Tris-HCl (pH 7.9) and 50% Opti-prep™) prepared in Comparative Example 1 were added to a 96-well round-bottom plate at each 5 μl/well. Thereto were added $5\times10^5$ lymphocytes prepared from the spleen of non-immune HHD mouse. The R10 medium was added so as to be a total amount of 200 μl. Thereafter, the plate was incubated at an incubator at 37° C., 5% $CO_2$, for 24 hours.

A GM1-treated FMP-DE-VLP sample and a GM1-treated FMP-HI-VLP sample were prepared as follows. A FMP-DE-VLP solution (500 μg/ml in 20 mM Tris-HCl (pH 7.9) and 50% Opti-prep™), and a FMP-HI-VLP solution (500 μg/ml in 20 mM Tris-HCl (pH 7.9) and 50% Opti-prep™) were added to a 96-well round-bottom plate at each 5 μl/well. Thereto was added 100 μl of a ganglioside GM1 solution (20 g/ml in the R10 medium) that is a type of glycolipids, a receptor of SV40. The mixture was incubated at 37° C., 5% $CO_2$ incubator, for 1 hour. After incubation, thereto were added $5\times10^5$ lymphocytes prepared from the spleen of non-immune HHD mouse. The R10 medium was added so as to be a total amount of 200 μl. Thereafter, the plate was incubated at an incubator at 37° C., 5% $CO_2$, for 24 hours.

To a 96-well round-bottom plate was added a buffer containing 20 mM Tris-HCl (pH 7.9) and 50% Opti-prep™ at 5 μl/well, as a control. Thereto were added $5\times10^5$ lymphocytes prepared from the spleen of non-immune HHD mouse. The R10 medium was added so as to be a total amount of 200 μl. Thereafter, the plate was incubated at an incubator at 37° C., 5% $CO_2$, for 24 hours.

After incubation, pretreatment of FACScan™ was performed as described in Example 2, and histogram analysis was performed with FACScan™ (Becton Dickinson). Cell Quest (Becton Dickinson) software was used for the analysis.

Figure 6B:
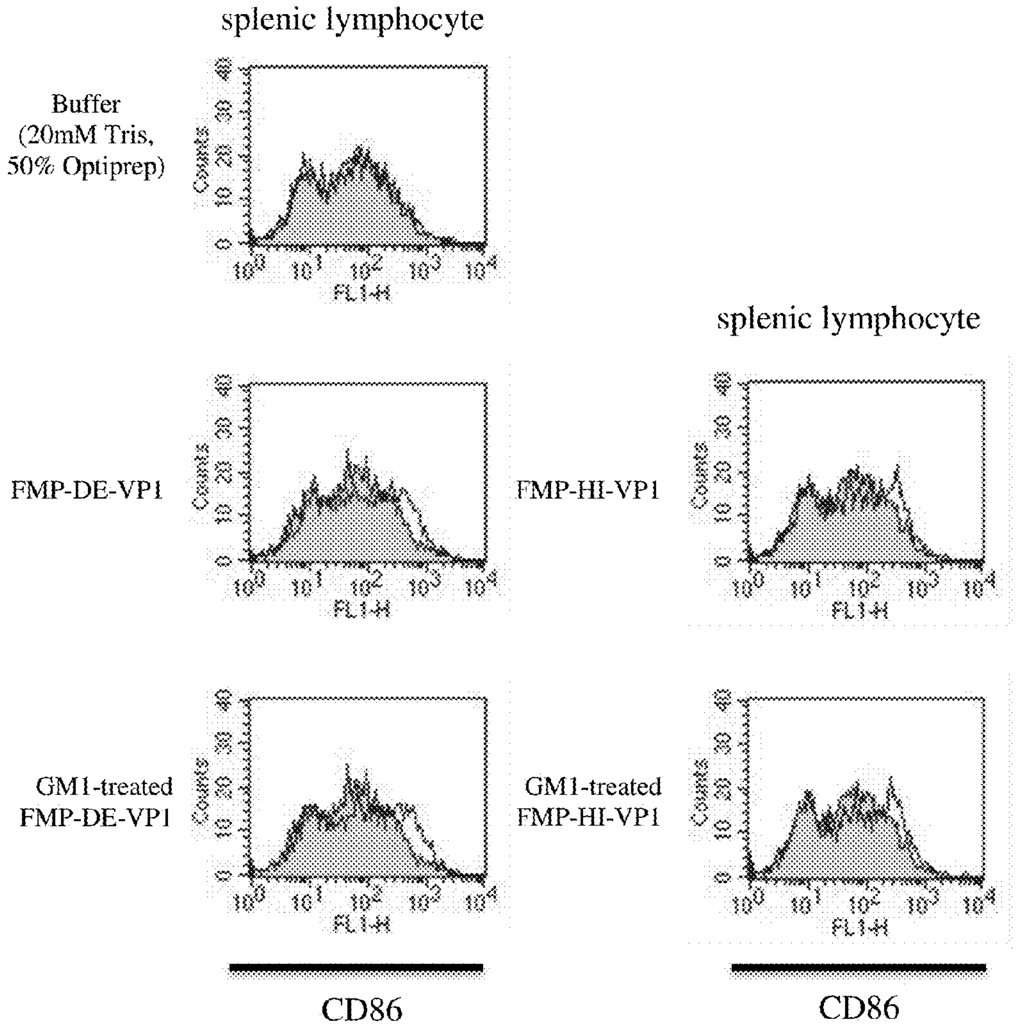
FIG. 6B is diagrams showing a FACScan™ analysis result showing an effect of GM1 or GD1a treatment on CD86 expression induction in lymphocytes derived from a non-immune mouse stimulated with FMP-DE-VLP or FMP-HI-VLP.

The results are shown in FIG. 6B. As shown in FIG. 6B, in the mouse lymphocytes incubated with FMP-DE-VLP, FMP-HI-VLP, GM1-treated FMP-DE-VLP and GM1-treated FMP-HI-VLP, the outlined peaks shifted to the right side as compared with the gray peaks, and induction of CD86 expression was suggested. Namely, expression induction of CD86 molecule was not inhibited by incubation with GM1.

Based on the above, it was considered that the mechanism of expression induction of CD86 molecule does not work through the binding with GM1. Therefore, a possibility different from the mechanism of CD86 expression induction by wt SV40 VP1 VLP was suggested.

Preparation of Baculovirus Expressing FLAG Sequence and 3xRGD Sequence-Inserted SV40 VP1

A FLAG sequence (DYKDDDDK, SEQ ID No. 47) or a 3xRGD sequence (RGDRGDRGD, SEQ ID No. 48) was inserted into SV40 VP1. Specifically, a DE loop region (137 to 138 amino acid region, classically, 4th Ala of a VP1 gene as amino acid No. 1) of VP1 was replaced with DYKDDDDK (SEQ ID No. 47) or RGDRGDRGD (SEQ ID No. 48) in which three glycines are added at the amino terminal and the carboxyl terminal to prepare a FLAG sequence-inserted SV40 VP1 insertion mutant (DE-FLAG VP1) or 3xRGD sequence-inserted SV40 VP1 insertion mutant (DE-3xRGD VP1). The mutant was prepared by the Overhang PCR method by employing pFastBac 1-SV40 wild type VP1 encoding SV40 VP1 as a template.

Primers for Preparing DE-FLAG-VP1

```
1st round
F Primer for preparing 5' side fragment
                                    (SEQ ID No. 10)
5'-AAAAGTCGACACCATGAAGATGGCCCCAACAAAAAG

R Primer for preparing 5' side fragment
                                    (SEQ ID No. 11)
5'-CTTGTCATCGTCGTCCTTGTAGTCTCCTCCTCCATG
AGTTTTTTGTGTCCCTGAATG

F Primer for preparing 3' side fragment
                                    (SEQ ID No. 12)
5'-CTACAAGGACGACGATGACAAGGGAGGAGGAGGTGC
TGGAAAACCCATTCAAG

R Primer for preparing 3' side fragment
                                    (SEQ ID No. 13)
5'-AAAAGGTACCTCACTGCATTCTAGTTGTGGTTTG

2nd round
F Primer
                                    (SEQ ID No. 10)
5'-AAAAGTCGACACCATGAAGATGGCCCCAACAAAAAG

R Primer
                                    (SEQ ID No. 13)
5'-AAAAGGTACCTCACTGCATTCTAGTTGTGGTTTG
```

Primers for Preparing DE-3xRGD-VP1

1st Round

```
1st round
F Primer for preparing 5' side fragment
                                    (SEQ ID No. 10)
5'-AAAAGTCGACACCATGAAGATGGCCCCAACAAAAAG

R Primer for preparing 5' side fragment
                                    (SEQ ID No. 14)
5'-GCCTCTATCGCCCCTGTCTCCTCTGCCTCCTCCATG
AGTTTTTTGTGTCCCTGAATG

F Primer for preparing 3' side fragment
                                    (SEQ ID No. 15)
5'-GAGACAGGGGCGATAGAGGCGACGGGGGAGGAGGTG
CTGGAAAACCCATTCAAG

R Primer for preparing 3' side fragment
                                    (SEQ ID No. 13)
5'-AAAAGGTACCTCACTGCATTCTAGTTGTGGTTTG

2nd round
F Primer
                                    (SEQ ID No. 10)
5'-AAAAGTCGACACCATGAAGATGGCCCCAACAAAAAG

R Primer
                                    (SEQ ID No. 13)
5'-AAAAGGTACCTCACTGCATTCTAGTTGTGGTTTG
```

10 ng of a template was employed. Each 50 pmol of primers were added to prepare 30 μL of a mixed solution containing 2.5 units of a KOD polymerase (TOYOBO), 0.2 mM dNTPs, 1 mM $MgCl_2$, 6 mM $(NH_4)_2SO_4$, 10 mM KCl, 120 mM Tris-HCl (pH 8.0), 0.1% Triton X-100, and 0.001% BSA.

In PCR, in both of 1st round and 2nd round, after incubation at 98° C. for 60 seconds, the following cycle was repeated 25 times (98° C. for 15 seconds, 59° C. for 15 seconds, 74° C. for 30 seconds) and finally, incubation was performed at 74° C. for 1 minute and 30 seconds, and the procedure was migrated to 4° C.

PCR fragments prepared by the Overhang PCR were cut with restriction enzymes KpnI and SalI. The cut PCR fragments were inserted between KpnI and SalI sites of a pFastBac 1 plasmid vector to obtain DE-FLAG VP1 or DE-3xRGD VP1 plasmid. *Escherichia coli* DH10bac (invitrogen) holding a baculovirus genome was transformed with each plasmid to prepare a recombinant baculovirus genome with the coding sequence of recombinant VP1 incorporated therein. The recombinant baculovirus genome was transfected to Sf-9 cells. After three days, the supernatant thereof was collected to obtain a solution containing recombinant baculovirus. A part of this solution was again infected with Sf-9 cells, thereby increasing a recombinant baculovirus titer. The resulting solution was referred to as a stock solution of a recombinant baculovirus.

Preparation of Baculovirus Expressing VP2 Fused M1 Protein

A coding sequence of FLAG tag (SEQ ID No. 18) was added to the upstream of a codon encoding an amino terminus (N-terminus) of wt SV40 VP2 (SEQ ID No. 16; the nucleic acid sequence is shown in SEQ ID No. 17), and a BamHI site was introduced into the further upstream thereof. The stop codon of wt SV40 VP2 coding sequence was removed, and an EcoRI site was introduced. The obtained polynucleotide was inserted via the BamHI site of pFastBac1 plasmid and the EcoRI site to prepare a plasmid containing wt SV40 VP2 gene. A coding sequence of a GGGGSGGGGSGGGGS linker (SEQ ID No. 19; the nucleic acid sequence is shown in SEQ ID No. 20) was introduced into the upstream of a codon encoding an N-terminus of M1 protein, and an EcoRI site was introduced into the further upstream thereof. The stop codon was added to the downstream of M1 protein coding sequence, and a Sal I site was introduced into the further downstream thereof. The obtained polynucleotide was introduced via the EcoRI site of the plasmid containing wt SV40 VP2 gene and the Sal I site to prepare a plasmid holding a gene fused with the M1 coding sequence in the downstream of the VP2 coding sequence.

*Escherichia coli* DH10bac (invitrogen) holding a baculovirus genome was transformed with this plasmid to prepare a recombinant baculovirus genome expressing protein VP2-M1 in which M1 was fused with wt SV40 VP2 (SEQ ID No. 21; the nucleic acid sequence is shown in SEQ ID No. 22). These recombinant baculovirus genomes were transfected to Sf-9 cells. After three days, the supernatant thereof was collected to obtain a solution containing recombinant baculovirus. A part of this solution obtained above was again infected with Sf-9 cells, thereby increasing a recombinant baculovirus titer. The resulting solution was referred to as a stock solution of a recombinant baculovirus.

Preparation of wt SV40 VP1 VLP Containing VP2-M1

A recombinant baculovirus with wt SV40 VP1 incorporated therein (M.O.I. (multiplicity of infection)=0.05 to 0.2) and a baculovirus with VP2-M1 incorporated therein (M.O.I.=0.015 to 0.06) were coinfected in a 15 cm culture dish in which $3\times10^7$ Sf-9 cells were inoculated (infection ratio of wt SV40 VP1:VP2-M1=1:0.3 (M.O.I. base)). A total of 10 dishes was prepared. Three days after infection, a total of $3\times10^8$ Sf-9 cells inoculated on these 10 dishes were collected, and washed with PBS(−). Thereafter, the cells were resuspended in 10 ml of a buffer for VP1 ultrasonic treatment (20 mM Tris-HCl (pH 7.9), 1% (w/vol) deoxycholic acid (Sigma)). In order to suppress endogenous protease activity, 2 mM phenylmethylsulfonyl fluoride (final concentration of 2 μM, Sigma), chymostatin (final concentration of 1 μg/ml, Sigma), aprotinin (final concentration of 1 μg/ml, Sigma), leupeptin (final concentration of 1 μg/ml, Sigma), antipain (final concentration of 1 μg/ml, Sigma) and pepstatin (final concentration of 1 μg/ml, Sigma) were added thereto, and the mixture was ultrasonically crushed. Thereafter, the crushed substance was centrifuged at 15,000 rpm, 4° C. for 5 minutes to separate into supernatant and pellet, and the supernatant was defined as a lysate solution.

Each 1.5 ml of a 20% CsCl solution (20 mM Tris-HCl (pH 7.9), 20% (w/vol) cesium chloride), a 30% CsCl solution (20 mM Tris-HCl (pH 7.9), 30% (w/vol) cesium chloride), a 40% CsCl solution (20 mM Tris-HCl (pH 7.9), 40% (w/vol) cesium chloride), and a 50% CsCl solution (20 mM Tris-HCl (pH 7.9), 50% (w/vol) cesium chloride) were superposed in an Ultra-Clear centrifugation tube (14×89 mm, Beckman coulter) in descending order of density, for density gradient centrifugation of cesium chloride. Further, 5 ml of the lysate solution containing wt SV40 VP1 containing VP2-M1 was superposed. The centrifugation tube was ultracentrifuged at 35,000 rpm, 4° C. for 3 hours (SW41Ti rotor, Beckman).

After ultracentrifugation, a white band appeared at the center was collected with 23 G, 1 ml of a Terumo syringe (0.60×32 mm, TERUMO). This fraction was mixed with a 37% CsCl solution (20 mM Tris-HCl (pH 7.9), 37% (w/vol) cesium chloride), and the mixture was transferred to an Ultra-Clear centrifugation tube (11×60 mm, Beckman coulter). Thereafter, the centrifugation tube was ultracentrifuged at 50,000 rpm, 4° C. for 20 hours (SW60Ti rotor, Beckman). After ultracentrifugation, a white band appeared at the center was collected with 23 G, 1 ml of a Terumo syringe (0.60×32 mm, TERUMO). This fraction was dialyzed (Slide-A-Lyzer (trademark) MINI Dialysis Units, 3500 MWCO, Thermo SCIENTIFIC) against a PBS(−) solvent. This fraction was centrifuged at 15,000 rpm, 4° C. for 5 minutes. The supernatant was collected and referred to as a wt SV40 VP1 VLP fraction containing purified VP2-M1.

Preparation of DE-FLAG VLP Containing VP2-M1 and DE-3xRGD VLP Containing VP2-M1

A recombinant baculovirus with DE-FLAG VP1 or DE-3xRGD VP1 incorporated therein (M.O.I. (multiplicity of infection)=0.05 to 0.2) and a baculovirus with VP2-M1 incorporated therein (M.O.I.=0.015 to 0.06) were coinfected in a 15 cm culture dish in which $3\times10^7$ Sf-9 cells were inoculated (infection ratio of DE-FLAG VP1 or DE-3xRGD VP1:VP2-M1=1:0.3 (M.O.I. base)). A total of 10 dishes was prepared. Three days after infection, a total of $3\times10^8$ Sf-9 cells inoculated on these 10 dishes were collected, and washed with PBS(−). Thereafter, the cells were resuspended in 10 ml of a buffer for VP1 ultrasonic treatment (20 mM Tris-HCl (pH 7.9), 1% (w/vol) deoxycholic acid (Sigma)). Thereafter, in order to suppress endogenous protease activity, 2 mM phenylmethylsulfonyl fluoride (final concentration of 2 μM, Sigma), chymostatin (final concentration of 1 μg/ml, Sigma), aprotinin (final concentration of 1 μg/ml, Sigma), leupeptin (final concentration of 1 μg/ml, Sigma), antipain (final concentration of 1 μg/ml, Sigma) and pepstatin (final concentration of 1 μg/ml, Sigma) were added thereto, and the mixture was ultrasonically crushed. Thereafter, the crushed substance was centrifuged at 15,000 rpm, 4° C. for 5 minutes to separate into supernatant and pellet, and the supernatant was referred to as a lysate solution.

Each 1.5 ml of a 20% CsCl solution (20 mM Tris-HCl (pH 7.9), 20% (w/vol) cesium chloride), a 30% CsCl solution (20 mM Tris-HCl (pH 7.9), 30% (w/vol) cesium chloride), a 40% CsCl solution (20 mM Tris-HCl (pH 7.9), 40% (w/vol) cesium chloride), and a 50% CsCl solution (20 mM Tris-HCl (pH 7.9), 50% (w/vol) cesium chloride) were superposed in an Ultra-Clear centrifugation tube (14×89 mm, Beckman coulter) in descending order of density, for density gradient centrifugation of cesium chloride. Further, 5 ml of the lysate solution containing wt SV40 VP1 containing VP2-M1 was superposed. The centrifugation tube was ultracentrifuged at 35,000 rpm, 4° C. for 3 hours (SW41Ti rotor, Beckman).

After ultracentrifugation, a white band appeared at the center was collected with 23 G, 1 ml of a Terumo syringe (0.60×32 mm, TERUMO). This fraction was mixed with a 37% CsCl solution (20 mM Tris-HCl (pH 7.9), 37% (w/vol) cesium chloride), and the mixture was transferred to an Ultra-Clear centrifugation tube (11×60 mm, Beckman coulter). Thereafter, the centrifugation tube was ultracentrifuged at 50,000 rpm, 4° C. for 20 hours (SW60Ti rotor, Beckman). After ultracentrifugation, a white band appeared at the center was collected with 23 G, 1 ml of a Terumo syringe (0.60×32 mm, TERUMO). This fraction was dialyzed (Slide-A-Lyzer (trademark) MINI Dialysis Units, 3500 MWCO, Thermo SCIENTIFIC) against a PBS(−) solvent. This fraction was centrifuged at 15,000 rpm, 4° C. for 5 minutes. The supernatant was collected and referred to as a DE-FLAG VP1 VLP fraction containing purified VP2-M1 and a DE-3xRGD VP1 VLP fraction containing purified VP2-M1.

Increase in Expression of CD86 Molecule by Stimulation of wt SV40 VP1 VLP Containing VP2-M1, DE-FLAG VLP Containing VP2-M1, and DE-3xRGD VLP Containing VP2-M1

A wt SV40 VP1 VLP solution containing VP2-M1 (500 μg/ml in PBS(−)), a DE-3xRGD VLP solution containing VP2-M1 (500 μg/ml in PBS(−)) and a DE-FLAG VLP solution containing VP2-M1 (500 μg/ml in PBS(−)) were added to a 96-well round-bottom plate at each 5 μl/well. Thereto were added $5\times10^5$ lymphocytes prepared from the spleen of non-immune HHD mouse. The R10 medium was added so as to be a total amount of 200 μl. Thereafter, the plate was incubated at an incubator at 37° C., 5% $CO_2$, for 24 hours.

After incubation, pretreatment of FACScan™ was performed as described in Example 2, and histogram analysis was performed with FACScan™ (Becton Dickinson). Cell Quest (Becton Dickinson) software was used for the analysis.

Figure 6C:
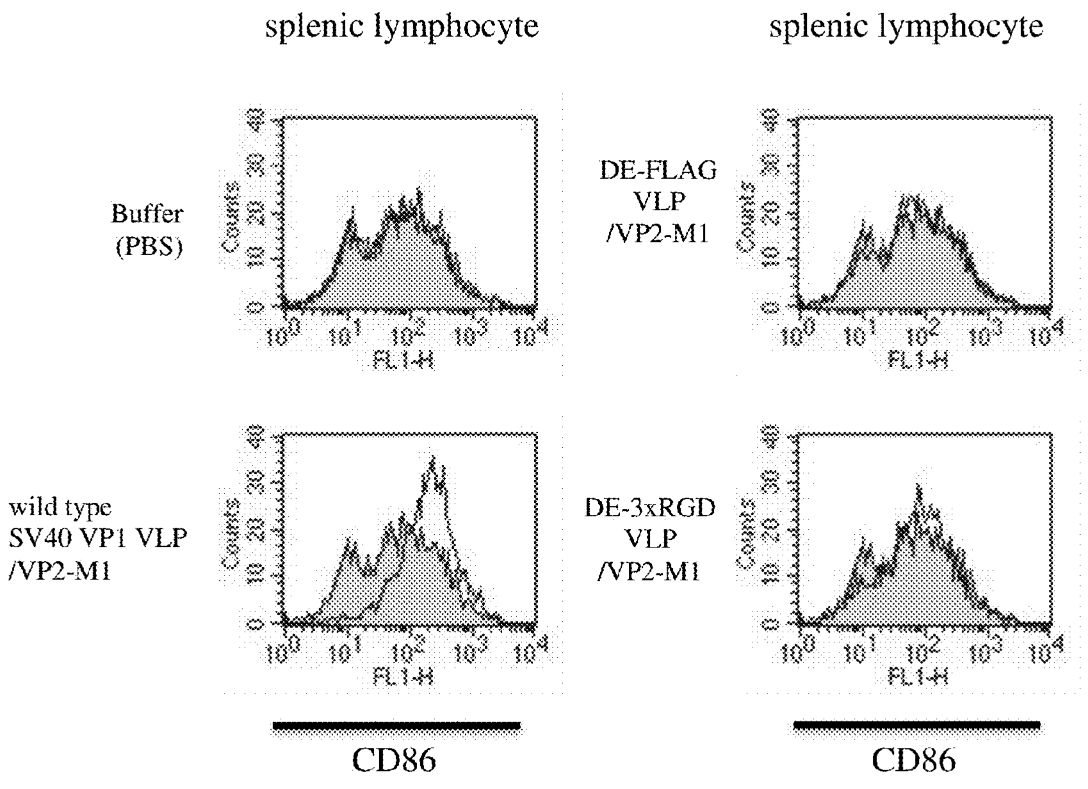
FIG. 6C is diagrams showing a FACScan™ analysis result showing an effect of GM 1 or GD1a treatment on CD86 expression induction in lymphocytes derived from a non-immune mouse stimulated with wt SV40 VP1 VLP including VP2-M1, DE-FLAG VLP including VP2-M1, or DE-3xRGD VLP including VP2-M1.

The results are shown in FIG. 6C. As shown in FIG. 6C, a shift of the outlined peak to the right side was observed in wt SV40 VP1 VLP containing VP2-M1 (lower left figure in FIG. 6C), and the CD86-inducing activity nearly the same as that of wt SV40 VP1 VLP was shown (FIG. 6A and FIG. 6C). Based on this result, it became clear that VLP comprising wt SV40 VP1, even when including VP2-M1, has high CD86 molecule expression-inducing ability as well as VLP comprising only wt SV40 VP1. On the other hand, expression induction of CD86 molecule was hardly observed in DE-FLAG VLP containing VP2-M1 and DE-3xRGD VLP containing VP2-M1 (upper right figure and lower right figure in FIG. 6C).

Based on the above result, it became clear that, when a heterologous peptide is inserted into a loop region of VP1, there may be cases where induction of CD86 molecule is not observed. Thus, it was suggested that wt SV40 VP1 VLP is effective for certainly inducing expression of CD86 molecule (activation of lymphocytes).

Example 4: Increase in Expression of Cell Surface CD69, CD81, CD83, CD86, CD196 and CD197 Molecules and Intracellular CD63 and CD68 Molecules by wt SV40 VP1 VLP Stimulation in Mouse Lymphocytes Preparation of Baculovirus Expressing Wild-Type (wt) Simian Virus 40 (SV40) VP1

A baculovirus expressing wt SV40 VP1 was prepared by the same method as described in Example 1.

Preparation of wt SV40 VP1 Virus-Like Particles (VLP)

wt SV40 VP1 VLP was prepared by the same method as described in Example 1.

Preparation of Lymphocytes from Spleen of Mouse

The lymphocytes were prepared from the spleen of mouse as described in Example 1, except for using the spleen of non-immune HHD mouse in place of that of the intraperitoneally immunized mouse.

Increase in Expression of CD69, CD81, CD83, CD86, CD196 and CD197 Molecules by wt SV40 VP1 VLP Stimulation To a 96-well round-bottom plate was added a wt SV40 VP1 VLP solution (500 μg/ml in PBS(−)) or PBS(−) alone at 5 μl/well. Thereto were added $5\times10^5$ lymphocytes prepared from the spleen of non-immune HHD mouse. The R10 medium was added so as to be a total amount of 200 μl. Thereafter, the plate was incubated at an incubator at 37° C., 5% $CO_2$, for 24 hours.

After incubation, the mixture was spun down at 4° C., 1,400 rpm to remove the supernatant, and the cells were loosened with a Vortex mixer. Thereafter, FACS buffer (2% FCS, 0.1% sodium azide, 1×PBS(−)) was added at 200 μl/well. The mixture was again spun down at 4° C., 1,400 rpm to remove the supernatant, and the cells were loosened. Thereafter, 100 μl of LEAF Purified Rat Anti-Mouse CD16/32 Clone: 93 (BioLegend) diluted to 20 μg/ml with FACS buffer was added thereto, and the mixture was incubated at 4° C. for 10 minutes. After incubation, washing operation with 200 μl of FACS buffer was carried out once. Thereafter, the cells were loosened and treated as follows.

(1) 50 μl of FITC American Hamster Anti-Mouse CD69 Clone: H1.2F3 (BD Pharmingen) diluted to 10 μg/ml with FACS buffer was added to the loosened cells, and the mixture was incubated in a dark place at 4° C. for 30 minutes.

(2) 50 μl of PE Armenian Hamster Anti-Mouse/Rat CD81 Clone: Eat-2 (BioLegend) diluted to 10 μg/ml with FACS buffer was added to the loosened cells, and the mixture was incubated in a dark place at 4° C. for 30 minutes.

(3) 50 μl of PE Rat Anti-Mouse CD83 Clone: Michel-19 (BioLegend) diluted to μg/ml with FACS buffer was added thereto, and the mixture was incubated in a dark place at 4° C. for 30 minutes.

(4) 50 μl of PE Rat Anti-Mouse CD86 Clone: GL-1 (BioLegend) diluted to 10 μg/ml with FACS buffer was added thereto, and the mixture was incubated in a dark place at 4° C. for 30 minutes.

(5) 50 μl of PE Armenian Hamster Anti-Mouse CD196 (CCR6) Clone: 29-2L17 (BioLegend) diluted to 10 μg/ml with FACS buffer was added to the loosened cells, and the mixture was incubated in a dark place at 4° C. for 30 minutes.

(6) 50 μl of PE Rat Anti-Mouse CD 197 (CCR7) Clone: 4B 12 (BioLegend) diluted to 10 μg/ml with FACS buffer was added thereto, and the mixture was incubated in a dark place at 4° C. for 30 minutes.

After incubation, washing operation with 200 μl of FACS buffer was carried out twice. Thereafter, FACS fixation buffer (1% formaldehyde, 1×FACS buffer) was added to the loosened cells at 100 μl/well. The mixture was incubated in a dark place at 4° C. overnight. Thereafter, 400 μl of FACS buffer was added to 5 ml of a polystyrene tube (BD Falcon®, 5 ml polystyrene round-bottom tube 12×75 mm style). Thereto was added a sample fixed with 100 μl of FACS fixation buffer. Thereafter, histogram analysis was performed with FACScan™ (Becton Dickinson). Cell Quest (Becton Dickinson) software was used for the analysis. The results are shown in FIG. 7A.

Figure 7A:
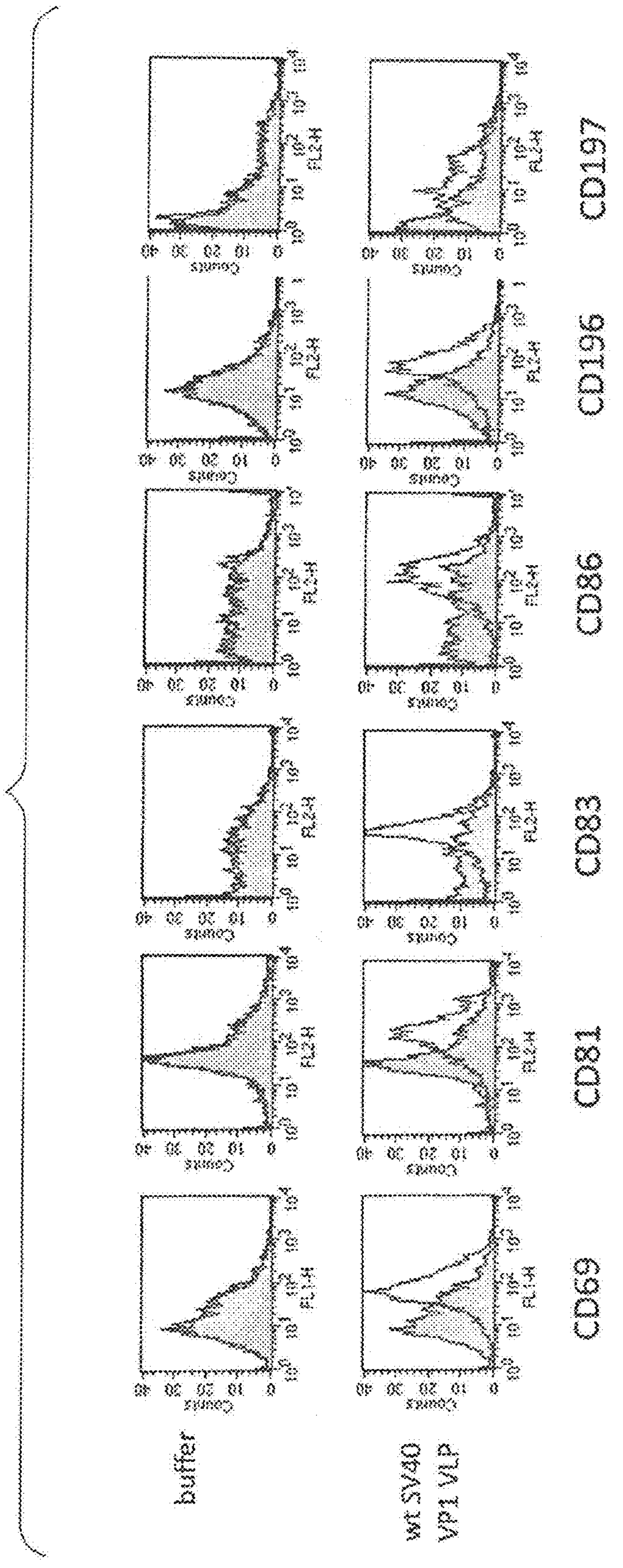
FIG. 7A is diagrams showing a FACScan™ analysis result showing expression of various CD molecules in lymphocytes derived from a non-immune mouse stimulated with wt SV40 VP1 VLP.

As shown in each figure in the upper row of FIG. 7A, the outlined peaks for the mouse lymphocytes stimulated with PBS(−) buffer alone nearly overlapped with the gray peaks for a sample incubated with only lymphocytes with no substance such as VLP and buffer added thereto and the R10 medium, stained with various fluorescent antibodies. On the other hand, the outlined peaks for the mouse lymphocytes stimulated with wt SV40 VP1 VLP shifted to the right side as compared with the gray peaks (each figure in the lower row of FIG. 7A). It shows that, when stimulated with wt SV40 VP1 VLP, cells highly expressing each of CD molecules increased. Based on the above, it became clear that wt SV40 VP1 VLP induces increase in expression of CD69, CD81, CD83, CD86, CD196 and CD197 molecules, in the mouse lymphocytes.

Increase in Expression of CD63 and CD68 Molecules by wt SV40 VP1 VLP Stimulation To a 96-well round-bottom plate was added a wt SV40 VP1 VLP solution (500 μg/ml in PBS(−)) at 5 μl/well. Thereto were added $5\times10^5$ lymphocytes prepared from the spleen of non-immune HHD mouse. The R10 medium was added so as to be a total amount of 200 μl. Thereafter, the plate was incubated at an incubator at 37° C., 5% $CO_2$, for 24 hours.

After incubation, the mixture was spun down at 4° C., 1,400 rpm to remove the supernatant, and the cells were loosened with a Vortex mixer. Thereafter, FACS buffer (2% FCS, 0.1% sodium azide, 1×PBS(−)) was added at 200 μl/well. The mixture was again spun down at 4° C., 1,400 rpm to remove the supernatant, and the cells were loosened. Thereafter, 100 μl of LEAF Purified Rat Anti-Mouse CD16/32 Clone: 93 (BioLegend) diluted to 20 μg/ml with FACS buffer was added thereto, and the mixture was incubated at 4° C. for 10 minutes. After incubation, washing operation with 200 μl of FACS buffer was carried out twice. Thereafter, BD Cytofix/Cytoperm (trademark) (BD Biosciences) was added to the loosened cells at 100 μl/well, and the mixture was incubated in a dark place at 4° C. for 20 minutes. After incubation, the same procedure was carried out twice as the washing operation using the FACS buffer, with 200 μl of 1×BD Perm/Wash (registered trademark) (BD biosciences). Thereafter, 2.5 μL of PE Rat anti-mouse CD63 antibody Clone: NVG-2 (BioLegend) or PE Rat anti-mouse CD68 antibody Clone: FA-11 (BioLegend) was added to 50 μl of 1×BD Perm/Wash (registered trademark). The mixture was added to the loosened cells, and this mixture liquid was added to each well. The mixture was incubated in a dark place at 4° C. for 30 minutes.

After incubation, the washing operation with 200 μl of 1×BD Perm/Wash (trademark) was carried out twice. Thereafter, FACS fixation buffer (1% formaldehyde, 1×FACS buffer) was added to the loosened cells at 100 μl per well, and the mixture was incubated in a dark place at 4° C. overnight. After incubation, 400 μl of FACS buffer was added to 5 ml of a polystyrene tube (BD Falcon®, 5 ml polystyrene round-bottom tube 12×75 mm style). Thereto was added a sample fixed with 100 μl of FACS fixation buffer. Thereafter, histogram analysis was performed with FACScan™ (Becton Dickinson). Cell Quest (Becton Dickinson) software was used for the analysis. The results are shown in FIG. 7B.

Figure 7B:
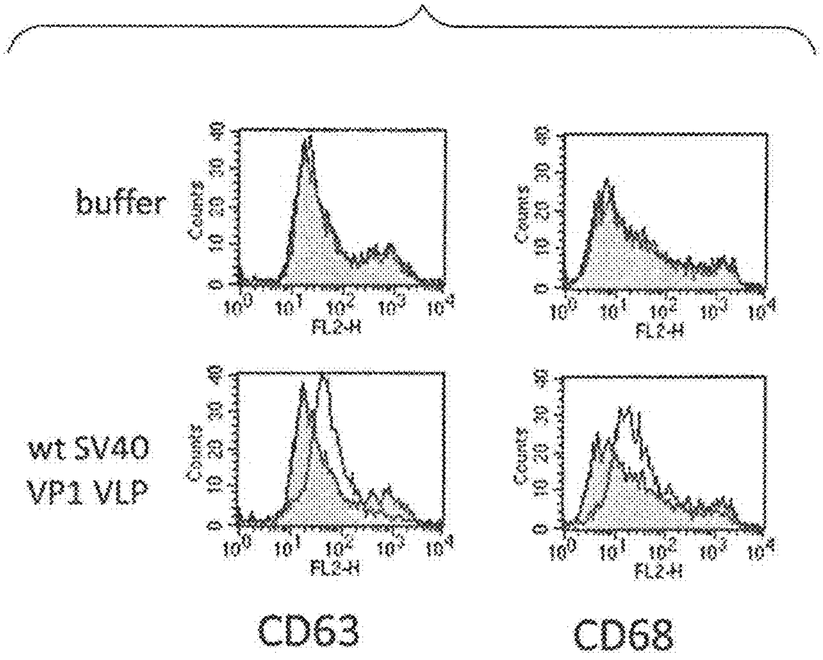
FIG. 7B is diagrams showing a FACScan™ analysis result showing expression of various CD molecules in lymphocytes derived from a non-immune mouse stimulated with wt SV40 VP1 VLP.

As shown in each figure in the upper row of FIG. 7B, the outlined peaks for the mouse lymphocytes stimulated with PBS(−) buffer alone nearly overlapped with the gray peaks for a sample incubated with only lymphocytes with no substance such as VLP and buffer added thereto and the R10 medium, stained with various fluorescent antibodies. On the other hand, the outlined peaks for the mouse lymphocytes stimulated with wt SV40 VP1 VLP shifted to the right side as compared with the gray peaks (each figure in the lower row of FIG. 7B). It shows that, when stimulated with wt SV40 VP1 VLP, cells highly expressing CD63 and CD68 molecules increased. Based on the above, it became clear that wt SV40 VP1 VLP induces increase in expression of CD63 and CD68 molecules, in the mouse lymphocytes.

Example 5: Induction of CD86 Molecule by wt SV40 VP1 VLP Stimulation in Mouse $CD4^+$T Cells, Mouse $CD8^+$T Cells and Mouse B Cells

Preparation of Baculovirus Expressing Wild-Type (wt) Simian Virus 40 (SV40) VP1

A baculovirus expressing wt SV40 VP1 was prepared by the same method as described in Example 1.

Preparation of wt SV40 VP1 Virus-Like Particles (VLP)

wt SV40 VP1 VLP was prepared by the same method as described in Example 1.

Preparation of Lymphocytes from Spleen of Mouse

The lymphocytes were prepared from the spleen of mouse as described in Example 1, except for using the spleen of non-immune HHD mouse in place of that of the intraperitoneally immunized mouse.

Analysis of Expression of $CD4^+$T, $CD8^+$T, and CD86 Molecule on B Cells by wt SV40 VP1 VLP Stimulation By positive selection from mouse spleen lymphocytes using magnetic beads, $CD4^+$T cells (mouse CD4 (L3T4) MicroBeads (Miltenyi Biotec Inc., 130-049-201)), $CD8^+$T cells (mouse CD8a (Ly-2) MicroBeads (Miltenyi Biotec Inc., 130-049-401)) and B cells (mouse CD19 MicroBeads (Miltenyi Biotec Inc., 130-052-201)) were prepared according to the method as described in the attached manual. The number of the prepared cells was counted, then the cells were used in the following experiment.

To a 96-well round-bottom plate was added a wt SV40 VP1 VLP solution (500 μg/ml in PBS(−)) at 5 μl/well. Thereto were each added $5\times10^5$ cells of $CD4^+$T, $CD8^+$T, and B cells. The R10 medium was added so as to be a total amount of 200 μl. Thereafter, the plate was incubated at an incubator at 37° C., 5% $CO_2$, for 24 hours. After incubation, pretreatment of FACScan™ was performed as described in Example 2, and histogram analysis was performed with FACScan™ (Becton Dickinson). Cell Quest (Becton Dickinson) software was used for the analysis. The result is shown in FIG. 8.

Figure 8:
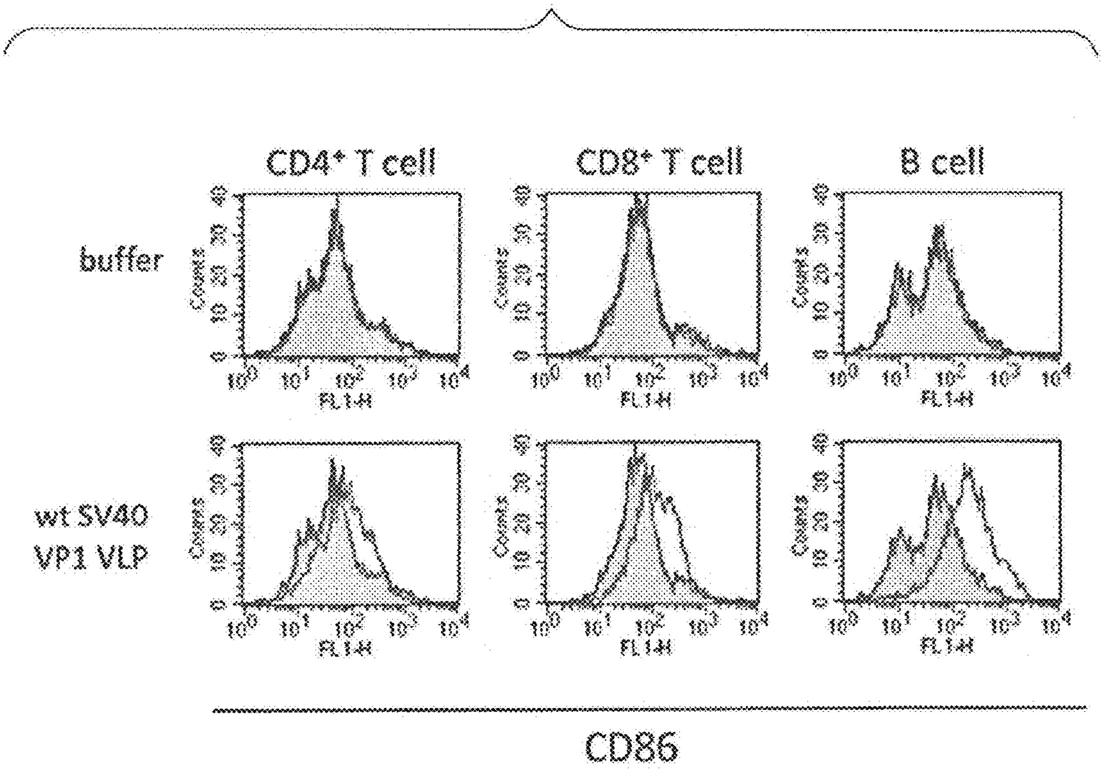
FIG. 8 is diagrams showing a FACScan™ analysis result showing expression of various CD molecules in $CD4^+$T cells, $CD8^+$T cells or B cells derived from a non-immune mouse stimulated with wt SV40 VP1 VLP.

As shown in each figure in the upper row of FIG. 8, the outlined peaks for the mouse lymphocytes stimulated with PBS(−) buffer alone nearly overlapped with the gray peaks for a sample incubated with only lymphocytes with no substance such as VLP and buffer added thereto and the R10 medium, stained with various fluorescent antibodies. On the other hand, the outlined peaks for the mouse lymphocytes stimulated with wt SV40 VP1 VLP shifted to the right side as compared with the gray peaks (each figure in the lower row of FIG. 8). It shows that, when stimulated with wt SV40 VP1 VLP, mouse $CD4^+$T cells, mouse $CD8^+$T cells and mouse B cells highly expressing CD86 molecule increased. Based on the above, it became clear that wt SV40 VP1 VLP induces increase in expression of CD86 molecule, in the mouse $CD4^+$T cells, mouse $CD8^+$T cells and mouse B cells.

Example 6: Induction of Secretion of CCL3 and CCL4 by wt SV40 VP1 VLP Stimulation in Mouse Lymphocytes Preparation of Baculovirus Expressing Wild-Type (wt) Simian Virus 40 (SV40) VP1

A baculovirus expressing wt SV40 VP1 was prepared by the same method as described in Example 1.

Preparation of wt SV40 VP1 Virus-Like Particles (VLP)

wt SV40 VP1 VLP was prepared by the same method as described in Example 1.

Preparation of Lymphocytes from Spleen of Mouse

The lymphocytes were prepared from the spleen of mouse as described in Example 1, except for using the spleen of non-immune HHD mouse in place of that of the intraperitoneally immunized mouse.

Preparation of Baculovirus Expressing M1 CTL Epitope-Inserted SV40 VP1

A baculovirus expressing M1 CTL epitope-inserted SV40 VP1 was prepared by the same method as described in Comparative Example 1.

Preparation of FMP-DE-VLP and FMP-HI-VLP

FMP-DE-VLP and FMP-HI-VLP were prepared by the same method as described in Comparative Example 1.

Induction of Secretion of Cytokines and Chemokines by wt SV40 VP1 VLP Stimulation A wt SV40 VP1 VLP solution (final concentration of 12.5 μg/ml), a FMP-DE-VLP solution (final concentration of 12.5 μg/ml), a FMP-HI-VLP solution (final concentration of 12.5 μg/ml), LPS (lipopolysaccharide, Sigma; final concentration of 1 μg/ml) and CT (cholera toxin, Sigma; final concentration of 12.5 μg/ml) were each added to a 96-well round-bottom plate. Thereto were added $5\times10^5$ lymphocytes prepared from the spleen of non-immune mouse. The R10 medium was added so as to be a total amount of 200 μl. Thereafter, the plate was incubated at an incubator at 37° C., 5% $CO_2$, for 24 hours.

Figure 9:
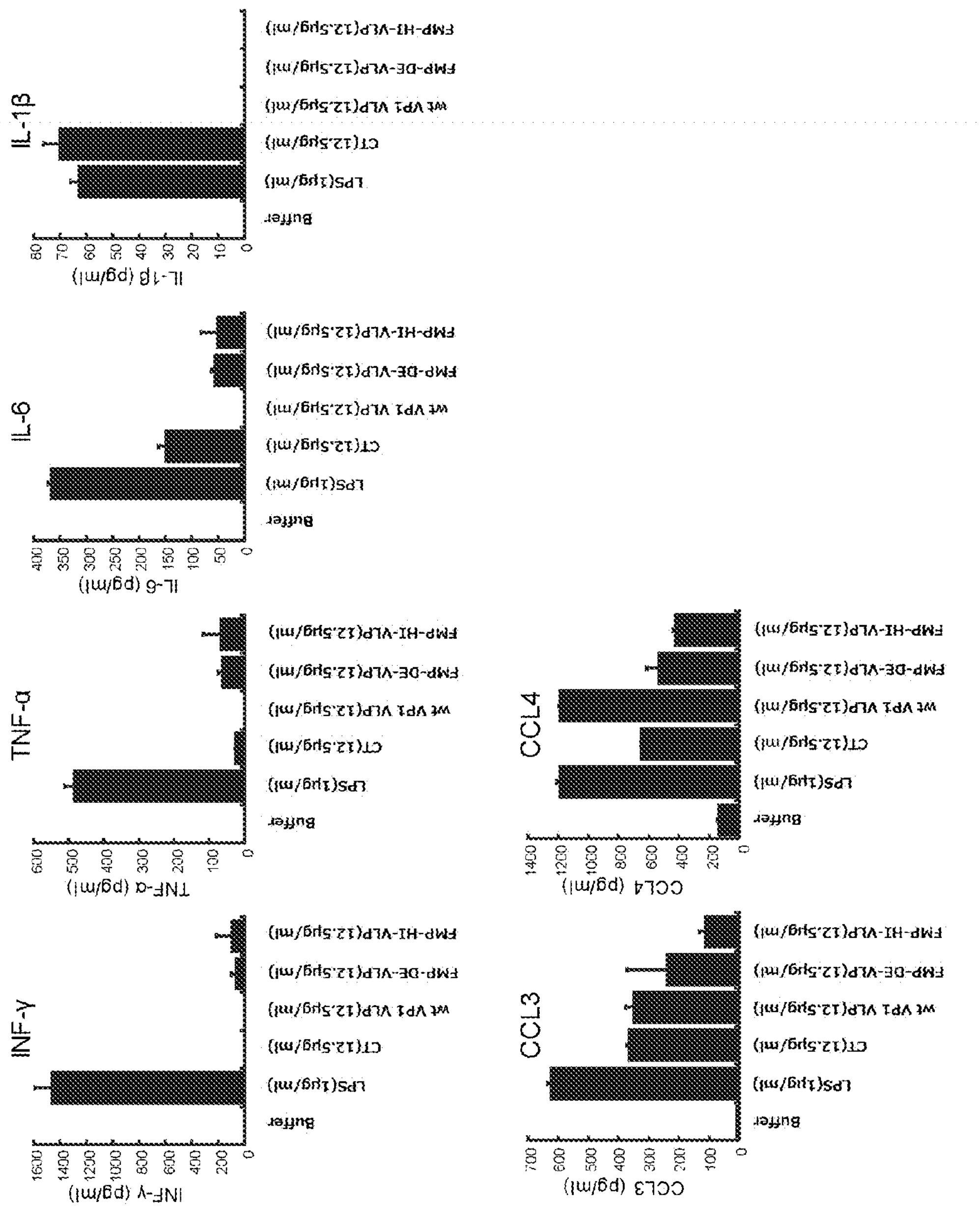
FIG. 9 is graphs showing production of various cytokines or chemokines in lymphocytes derived from a non-immune mouse stimulated with wt SV40 VP1 VLP.

After incubation, the cell supernatant was collected. The amounts of IFN-γ (DY485 Mouse IFN-gamma DuoSet, R&D SYSTEMS), TNF-α (DY410 Mouse TNF-alpha DuoSet, R&D SYSTEMS), IL-6 (DY406 Mouse IL-6 DuoSet, R&D SYSTEMS), IL-1β (DY401 Mouse IL-1 beta/IL-1F2 DuoSet, R&D SYSTEMS), CCL3 (DY450 Mouse CCL3/MPI-1α DuoSet, R&D SYSTEMS) and CCL4 (DY451 Mouse CCL4/MIP-1β DuoSet, R&D SYSTEMS) contained in the cell supernatant were detected by ELISA method. Detection was performed according to the manual of the kit. The result is shown in FIG. 9.

As a result, wt SV40 VP1 VLP did not induce secretion of IFN-γ, TNF-α, IL-6 and IL-1β (cytokines inducing systemic inflammation) and induced secretion of CCL3 and CCL4 (chemokines inducing local inflammation). On the other hand, CT induced secretion of IL-6 and IL-1β, in addition to CCL3 and CCL4, and LPS induced secretion of all cytokines and chemokines. Based on the above, it was suggested that wt SV40 VP1 VLP of the present example reduces systemic inflammation, as compared to CT and LPS that are known adjuvants.

FMP-DE-VLP and FMP-HI-VLP induced a little secretion of IFN-γ, TNF-α and IL-6, and also induced secretion of CCL3 and CCL4. However, the expression levels of CCL3 and CCL4 were lower than wt SV40 VP1 VLP of the present example. Based on the above, it was suggested that wt SV40 VP1 VLP of the present example reduces systemic inflammation, as compared to FMP-DE-VLP and FMP-HI-VLP, and can further induce local inflammation.

Comparative Example 2: Increase in Expression of CD86 Molecule by SV40 Virus Stimulation in Mouse Lymphocytes and Induction of Secretion of Various Cytokines Preparation of Simian Virus 40 (SV40) Virus Plasmid pUC-SV40 (SEQ ID No. 24) into which a gene encoding SV40 genome (SEQ ID No. 23) was inserted was treated with BamHI. T4 DNA Ligase (TaKaRa) was added to cyclize the SV40 genome. The cyclized SV40 genome was transfected to CV-1 cells using a transfection reagent (Effectene™, Qiagen). Three days after transfection, the medium was collected by the cells. Freezing and melting of the collected medium was repeated three times. Thereafter, the medium was again mixed with CV-1 cells to be infected. Three days after infection, the medium was collected by the cells. The virus titer of the SV40 virus contained in the medium was calculated by the plaque assay method.

Preparation of Lymphocytes from Spleen of Mouse

The lymphocytes were prepared from the spleen of mouse as described in Example 1, except for using the spleen of non-immune HHD mouse in place of that of the intraperitoneally immunized mouse.

Increase in Expression of CD86 Molecule by SV40 Virus Stimulation

The lymphocytes prepared from the spleen of non-immune mouse were added to a 96-well round-bottom plate at $5\times10^5$ cells/well. Thereto was added a SV40 virus solution at $1\times10^6$ to 1 plaque forming unit (pfu).

The R10 medium was added so as to be a total amount of 200 μl. Thereafter, the plate was incubated at an incubator at 37° C., 5% $CO_2$, for 24 hours.

After incubation, pretreatment of FACScan™ was performed as described in Example 2, and histogram analysis was performed with FACScan™ (Becton Dickinson). Cell Quest (Becton Dickinson) software was used for the analysis.

Figure 10A:
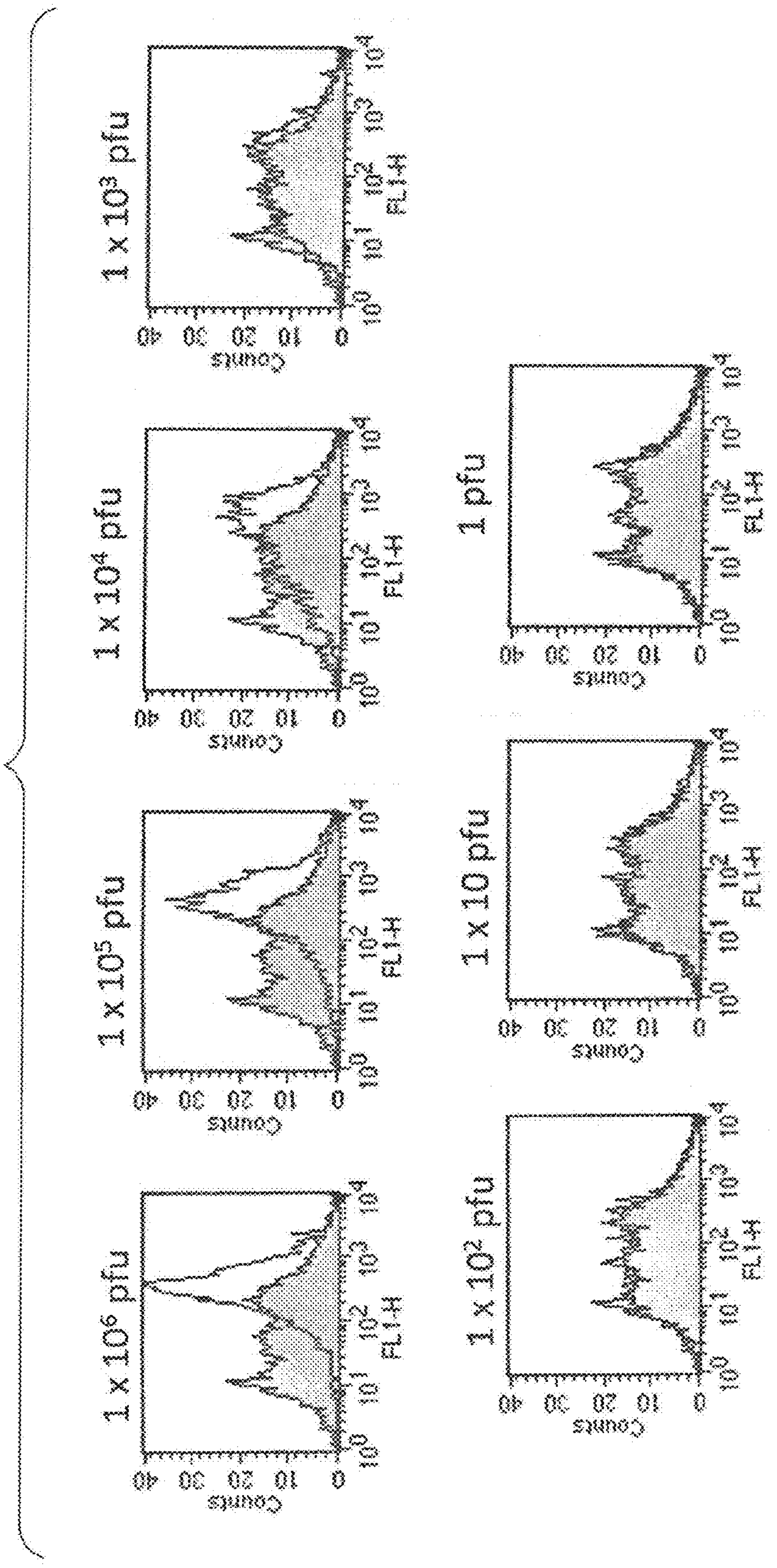
FIG. 10A is diagrams showing a FACScan™ analysis result showing expression of CD86 derived from a non-immune mouse stimulated with SV40.

The results are shown in FIG. 10A. In FIG. 10A, the gray histograms show the number of cells in each fluorescence intensity when incubated with R10 medium alone without adding a SV40 virus solution. The outlined histograms show the number of cells in each fluorescence intensity when incubated with R10 medium added with a SV40 virus solution. As a result of analysis, the outlined peaks for mouse lymphocytes stimulated with 1 to $1\times10^2$ pfu SV40 virus nearly overlapped with the gray peaks (each figure in the lower row of FIG. 10A).

On the other hand, the outlined peaks for the mouse lymphocytes stimulated with $1\times10^3$ to $1\times10^6$ pfu SV40 virus shifted to the right side as compared with the gray peaks (each figure in the upper row of FIG. 10A). Based on the above, it became clear that SV40 virus induces increase in expression of CD86 molecule, in the mouse lymphocytes.

Increase in Expression of SV40 Virus-Stimulated Cytokines and Chemokines

A SV40 virus solution ($1\times10^7$ plaque forming unit (pfu)/ml, $1\times10^6$ pfu/ml, $1\times10^5$ pfu/ml, $1\times10^4$ pfu/ml, $1\times10^3$ pfu/ml, $1\times10^2$ pfu/ml) was added to a 96-well round-bottom plate at 100 μl/well. Thereto were added $5\times10^5$ lymphocytes prepared from the spleen of naive mouse. The R10 medium was added so as to be a total amount of 200 μl. Thereafter, the plate was incubated at an incubator at 37° C., 5% $CO_2$, for 24 hours.

After incubation, the cell supernatant was collected. The amounts of IFN-γ (DY485 Mouse IFN-gamma DuoSet, R&D SYSTEMS), TNF-α (DY410 Mouse TNF-alpha DuoSet, R&D SYSTEMS), IL-6 (DY406 Mouse IL-6 DuoSet, R&D SYSTEMS), IL-1β (DY401 Mouse IL-1 beta/IL-1F2 DuoSet, R&D SYSTEMS), CCL3 (DY450 Mouse CCL3/MPI-1α DuoSet, R&D SYSTEMS) and CCL4 (DY451 Mouse CCL4/MIP-1β DuoSet, R&D SYSTEMS) contained in the cell supernatant were detected by ELISA method. Detection was performed according to the manual of the kit. The results are shown in FIG. 10B.

Figure 10B:
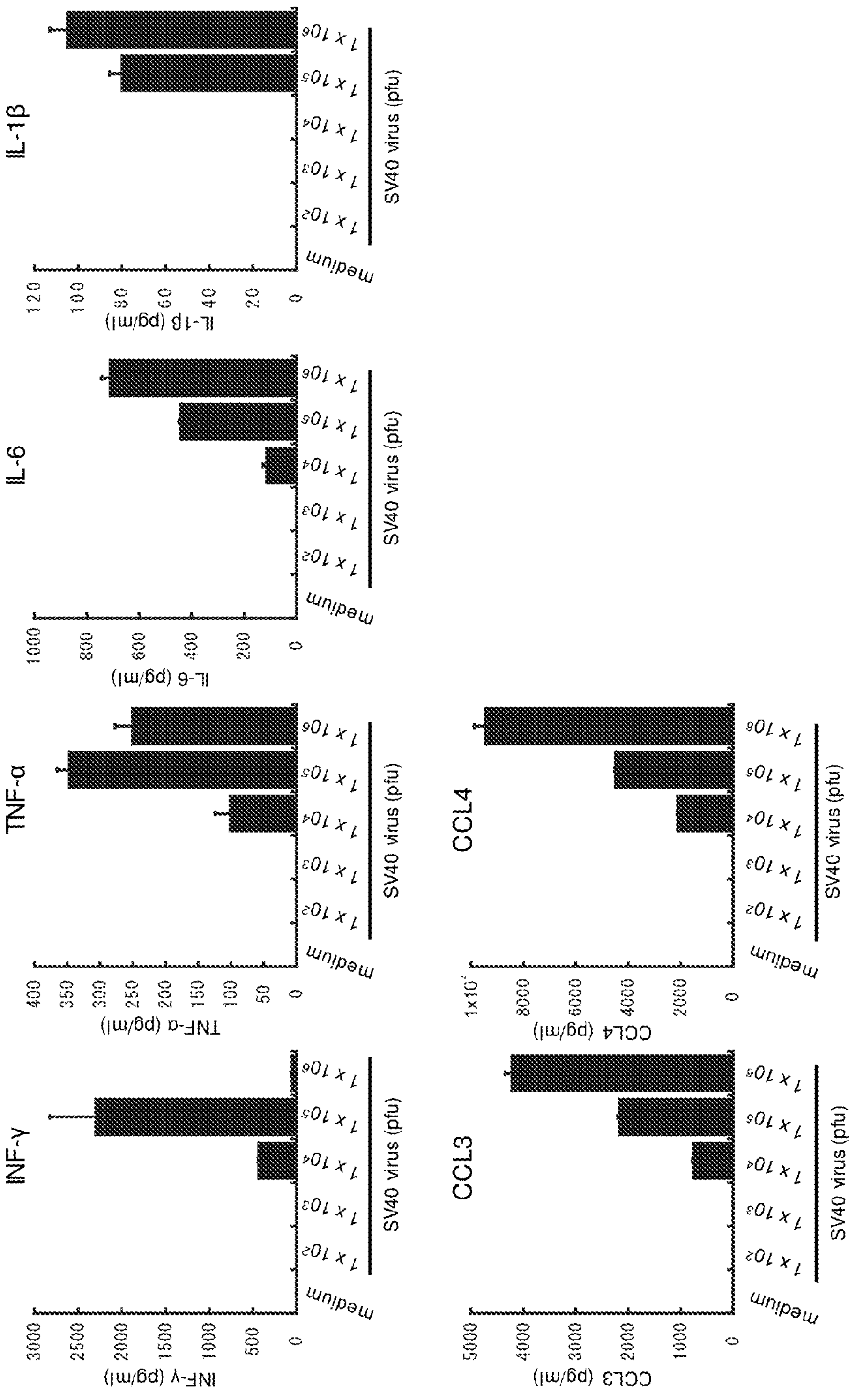
FIG. 10B is graphs showing production of various cytokines or chemokines in lymphocytes derived from a non-immune mouse stimulated with SV40.

As a result, the SV40 virus induced secretion of all analyzed cytokines (IFN-γ, TNF-α, IL-6 and IL-1β) and chemokines (CCL3 and CCL4) (FIG. 10B). It is different from the pattern observed in Example 6 that wt SV40 VP1 VLP does not induce production of IFN-γ, TNF-α, IL-6 and IL-1β, and induces secretion of chemokines, CCL3 and CCL4. Based on the above, a possibility that a factor other than outer coat (capsid) of SV40 virus also involves in the activation of mouse lymphocytes by SV40 virus was suggested.

Example 7: Preparation of Baculovirus Expressing Phosphorylated Wild-Type (wt) Simian Virus 40 (SV40) VP1 of Erk1/2, JNK and p38MAPK by wt SV40 VP1 VLP Stimulation in Mouse Lymphocytes A baculovirus expressing wt SV40 VP1 was prepared as described in Example 1.

Preparation of wt SV40 VP1 Virus-Like Particles (VLP)

wt SV40 VP1 VLP was prepared as described in Example 1.

Preparation of Lymphocytes from Spleen of Mouse

The lymphocytes were prepared from the spleen of mouse as described in Example 1, except for using the spleen of non-immune HHD mouse in place of that of the intraperitoneally immunized mouse.

Analysis of Phosphorylation of Erk1/2, JNK and p38-MAPK Molecule by wt SV40 VP1 VLP Stimulation To a 96-well round-bottom plate was added 5 μl of a wt SV40 VP1 VLP solution (500 μg/ml in PBS(−)) or PBS(−) alone. Thereto were added $5\times10^5$ lymphocytes prepared from the spleen of non-immune mouse.

The R10 medium was added so as to be a total amount of 200 μl. Thereafter, the plate was incubated at an incubator at 37° C., 5% $CO_2$, for 10 minutes, 30 minutes, and 1 hour.

After incubation, the mixture was spun down at 4° C., 1,400 rpm to remove the supernatant, and the cells were loosened with a Vortex mixer. Thereafter, FACS buffer (2% FCS, 0.1% sodium azide, 1×PBS(−)) was added at 200 μl/well. The mixture was again spun down at 4° C., 1,400 rpm to remove the supernatant, and the cells were loosened. Thereafter, 100 μl of LEAF Purified Rat Anti-Mouse CD16/32 Clone: 93 (BioLegend) diluted to 20 μg/ml with FACS buffer was added thereto, and the mixture was incubated at 4° C. for 10 minutes. After incubation, washing operation with 200 μl of FACS buffer was carried out twice. Thereafter, BD Cytofix/Cytoperm (registered trademark) (BD Biosciences) was added to the loosened cells at 100 μl/well, and the mixture was incubated in a dark place at 4° C. for 20 minutes. After incubation, the same procedure was carried out twice as the washing operation using the FACS buffer, with 200 μl of 1×BD Perm/Wash (trademark) (BD biosciences). Thereafter, the cells were loosened and treated as follows.

(1) 1 μL of Phospho-p44/42 MAPK (Erk1/2) (Thr202/Tyr204) (D13.14.4E) XP (trademark) Rabbit mAb (PE conjugate) (Cell Signaling TECHNOLOGY, #5682) was added to 50 μl of 1×BD Perm/Wash (registered trademark). This mixture liquid was added to each well, and the resulting mixture was incubated in a dark place at 4° C. for 30 minutes.

(2) 1 μL of Phospho-SAPK/JNK (Thr183/Tyr185) (G9) Mouse mAb (PE Conjugate) (Cell Signaling TECHNOLOGY, #5755) was added to 50 μl of 1×BD Perm/Wash (registered trademark). This mixture liquid was added to each well, and the resulting mixture was incubated in a dark place at 4° C. for 30 minutes.

(3) 1 μL of Phospho-p38 MAPK (Thr180/Tyr182) (3D7) Rabbit mAb (PE Conjugate) (Cell Signaling TECHNOLOGY, #6908) was added to 50 μl of 1×BD Perm/Wash (trademark). This mixture liquid was added to each well, and the resulting mixture was incubated in a dark place at 4° C. for 30 minutes.

After incubation, the washing operation with 200 μl of 1×BD Perm/Wash (trademark) was carried out twice. Thereafter, FACS fixation buffer (1% formaldehyde, 1×FACS buffer) was added to the loosened cells at 100 μl/well. The mixture was incubated in a dark place at 4° C. overnight.

After incubation, 400 μl of FACS buffer was added to 5 ml of a polystyrene tube (BD Falcon®, 5 ml polystyrene round-bottom tube 12×75 mm style). Thereto was added a sample fixed with 100 μl of FACS fixation buffer. Thereafter, histogram analysis was performed with FACScan™ (Becton Dickinson). Cell Quest (Becton Dickinson) software was used for the analysis. The results are shown in FIGS. 11A to 11C.

Figure 11A:
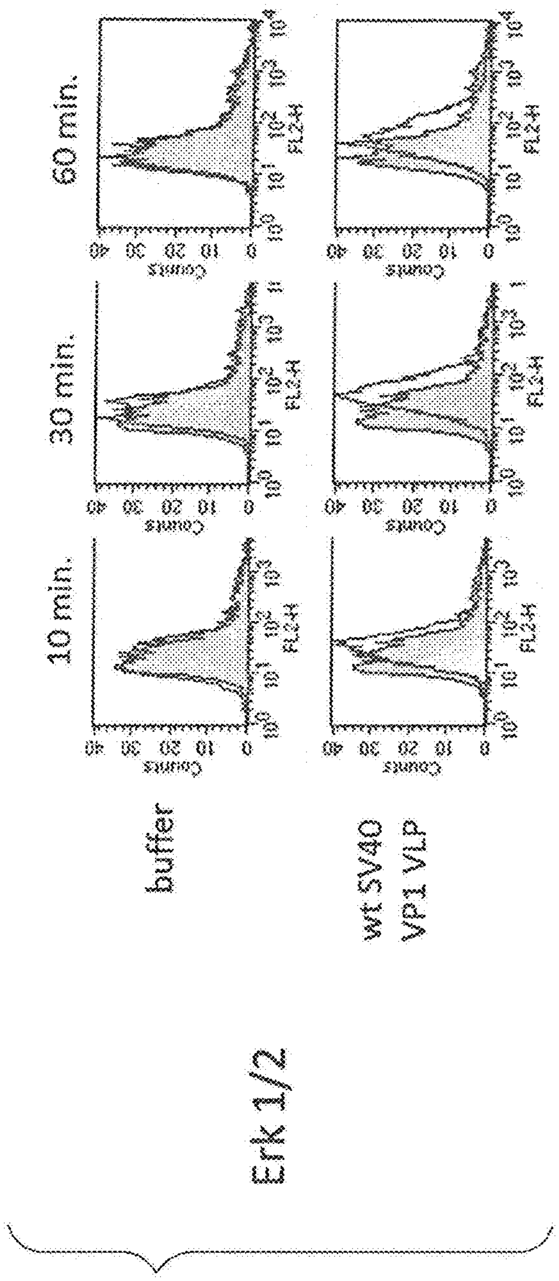
FIG. 11A is diagrams showing a FACScan™ analysis result showing phosphorylation of Erk1/2 by lymphocytes derived from a non-immune mouse stimulated with wt SV40 VP1 VLP.
Figure 11B:
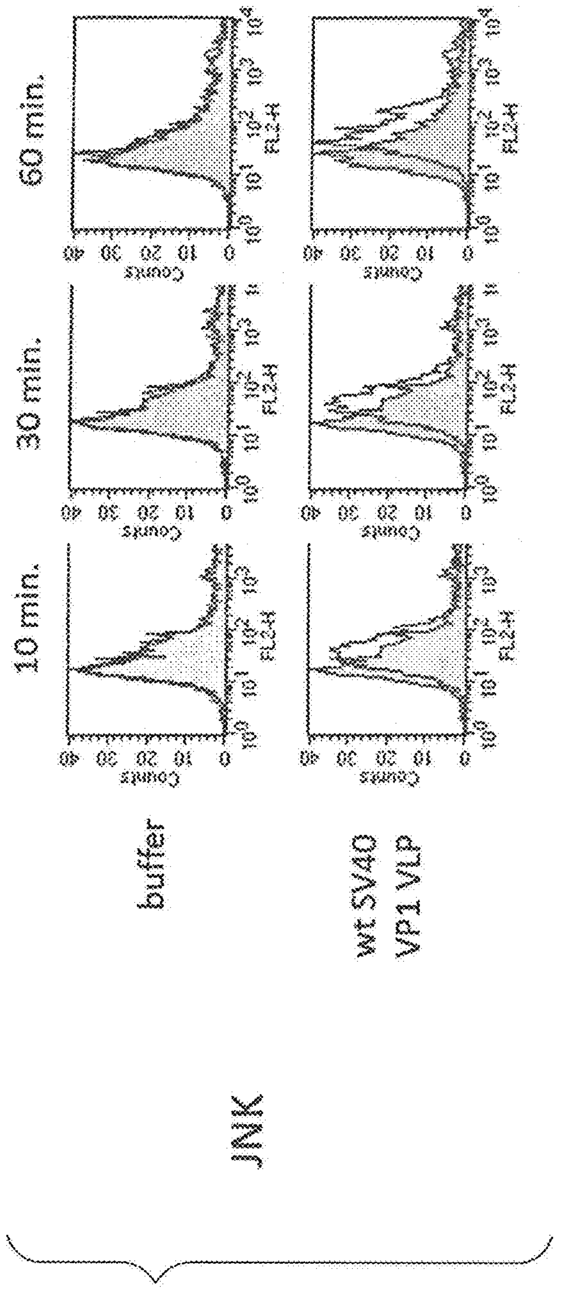
FIG. 11B is diagrams showing a FACScan™ analysis result showing phosphorylation of JNK by lymphocytes derived from a non-immune mouse stimulated with wt SV40 VP1 VLP.
Figure 11C:
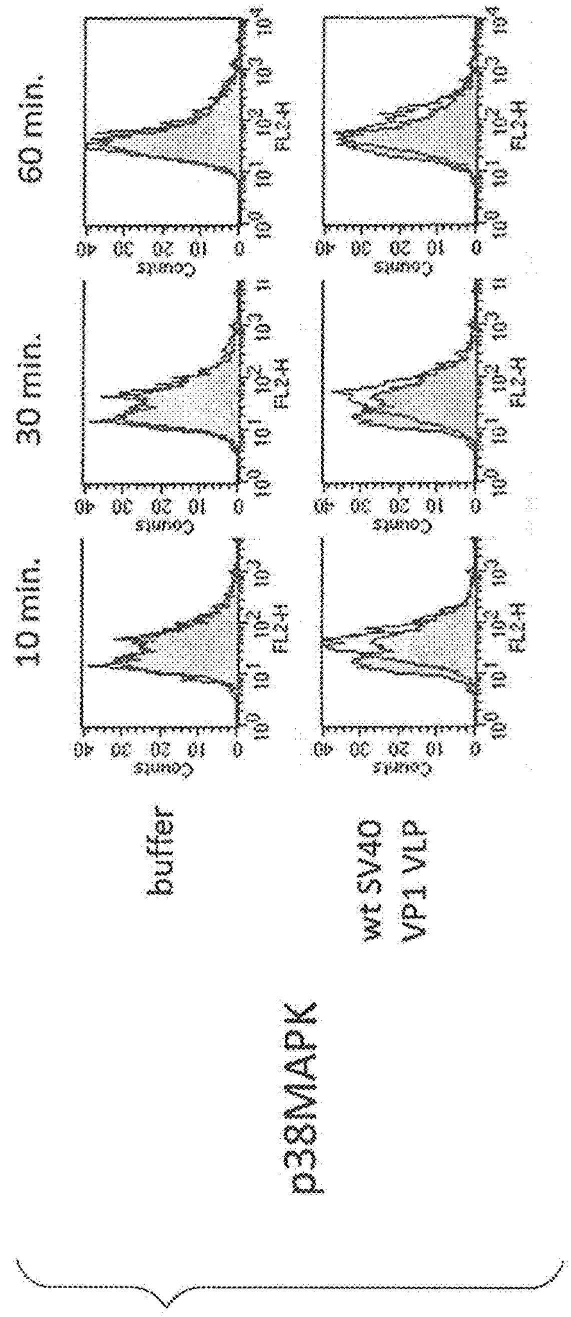
FIG. 11C is diagrams showing a FACScan™ analysis result showing phosphorylation of p38MAPK by lymphocytes derived from a non-immune mouse stimulated with wt SV40 VP1 VLP.

In FIGS. 11A to 11C, outlines represent a fluorescence intensity of various anti-phospho antibodies on Erk1/2, JNK or p38MAPK of a mouse lymphocyte sample incubated with wt SV40 VP1 VLP (wt SV40 VP1 VLP, in FIGS. 11A to 11C) or PBS(−) buffer alone (buffer, in FIGS. 11A to 11C) and stained with various anti-phospho antibodies. Gray lines represent a fluorescence intensity of an antibody on various anti-phospho antibodies of a mouse lymphocyte sample incubated with wt SV40 VP1 VLP or R10 medium alone without containing PBS(−) buffer and stained with various anti-phospho antibodies.

As shown in each figure in the upper row of FIGS. 11A to 11C, the outlined peaks for mouse lymphocytes stimulated with PBS(−) buffer alone nearly overlapped with the gray peaks. On the other hand, the outlined peaks for the mouse lymphocytes stimulated with wt SV40 VP1 VLP shifted to the right side as compared with the gray peaks (each figure in the lower row of FIGS. 11A to 11C). Based on the above results, it was found that wt SV40 VP1 VLP induces phosphorylation of mouse Erk1/2, JNK and p38MAPK, in the mouse lymphocytes.

The cells respond to stimulation of adjuvant or the like and activate, and these molecules are phosphorylated. Phosphorylation of these molecules in lymphocytes suggests that the lymphocytes were activated by wt SV40 VP1 VLP of the present example.

What is claimed is:

1. A method for potentiating an immune effect of a living body, comprising administering an adjuvant and a vaccine comprising an exogenous antigen to a living body and inducing production of CD86+ lymphocytes in the living body, the adjuvant comprising a pharmacologically effective amount of virus-like particles, wherein the virus-like particles comprise an outer coat protein comprising the amino acid sequence of SEQ ID NO: 1;

wherein the outer coat protein constitutes an outer coat of the virus-like particles;

wherein the virus-like particles do not substantially comprise a genome DNA of SV40; and wherein the virus-like particles do not substantially comprise the exogenous antigen.

2. The method according to claim 1, wherein the virus-like particles do not substantially comprise VP2, VP3, or both of them.

3. The method according to claim 1, wherein the administrating step is conducted by oral administration, transmucosal administration, parenteral administration, or transdermal administration.

4. A method for potentiating an immune effect of a living body, comprising administering an adjuvant and a vaccine comprising an exogenous antigen to a living body, the adjuvant comprising a pharmacologically effective amount of virus-like particles;

wherein the virus-like particles comprise an outer coat protein comprising the amino acid sequence of SEQ ID NO: 1;

wherein the virus-like particles do not substantially comprise a genome DNA of SV40; and wherein the virus-like particles do not substantially comprise the exogenous antigen.

* * * * *